US012673057B2

(12) United States Patent
Yang

(10) Patent No.: US 12,673,057 B2
(45) Date of Patent: Jul. 7, 2026

(54) RIPK2 INHIBITION FOR THE TREATMENT OF CANCER

(71) Applicant: CEDARS-SINAI MEDICAL CENTER, Los Angeles, CA (US)

(72) Inventor: Wei Yang, Studio City, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 721 days.

(21) Appl. No.: 17/913,760

(22) PCT Filed: Mar. 29, 2021

(86) PCT No.: PCT/US2021/024740
§ 371 (c)(1),
(2) Date: Sep. 22, 2022

(87) PCT Pub. No.: WO2021/202428
PCT Pub. Date: Oct. 7, 2021

(65) Prior Publication Data
US 2023/0139516 A1 May 4, 2023

Related U.S. Application Data

(60) Provisional application No. 63/001,951, filed on Mar. 30, 2020.

(51) Int. Cl.
*A61K 31/5025* (2006.01)
*A61P 35/02* (2006.01)
*C12Q 1/6886* (2018.01)

(52) U.S. Cl.
CPC .......... *A61K 31/5025* (2013.01); *A61P 35/02* (2018.01); *C12Q 1/6886* (2013.01)

(58) Field of Classification Search
CPC .................................................. A61K 31/5025
See application file for complete search history.

(56) References Cited

U.S. PATENT DOCUMENTS 9,340,830 B2 5/2016 Lipson et al.
2016/0045607 A1 * 2/2016 Crew .................... A61K 47/55
514/369

FOREIGN PATENT DOCUMENTS

WO 2012088067 A1 6/2012
WO 2017200826 A1 11/2017
WO WO2017200826 * 11/2017 ........... A61K 31/395
WO 2021202428 A1 10/2021

OTHER PUBLICATIONS

Canning et al., Chem & Bio. (2015) vol (22(9) pp. 1174-1184.*
Yan et al., Cancer Research (2018) vol. 78(13) pp. 1-4.*
McMahon et al. (2000).*
Pinedo et al (2000).*
International Search Report and Written Opinion for PCT/US2021/024740 dated Jul. 9, 2021, 12 pages.
Canning et al., Inflammatory Signaling by NOD-RIPK2 is Inhibited by Clinically Relevant Type II Kinase Inhibitors, Chemistry and Biology, 2015, vol. 22(9), pp. 1174-1184.
Yan et al., Abstract 2694: Receptor-interacting protein kinase 2 promotes prostate cancer progression by activating the MAX:MYC pathway, Cancer Research, 2018, vol. 78(13), pp. 1-4.
Yan et al. RIPK2 Stabilizes c-Myc and is an Actionable Target for Inhibiting Prostate Cancer Metastasis, bioRxiv, 2020, pp. 1-21.
Yan et al., Receptor-interacting protein kinase 2 promotes prostate cancer progression by activating the MAX:MYC pathway, American Association for Cancer Research Annual Meeting, Apr. 2018.
Mertins et al., "Proteogenomics connects somatic mutations to signalling in breast cancer." Nature 534.7605 (2016): 55-62.
Ross-Adams et al., "Integration of copy number and transcriptomics provides risk stratification in prostate cancer: a discovery and validation cohort study." EBioMedicine 2.9 (2015): 1133-1144.
Supplementary European Search Report in European Patent Application No. EP21782056, Mailed Jul. 8, 2025 (13 pages).

* cited by examiner

*Primary Examiner* — Paul V Ward

(74) *Attorney, Agent, or Firm* — Linda B. Huber; Nixon Peabody LLP

(57) ABSTRACT

Described herein are treatments and patient selection methods for cancers such as prostate cancer, breast cancer, liver cancer, bladder cancer, and melanoma. The treatment involves administering a RIPK2 inhibitor to a subject. The patient selection involves selecting a patient who has increased copy numbers or expression of both RIPK2 and MYC.

8 Claims, 32 Drawing Sheets
Specification includes a Sequence Listing.

DMSO       GSK583

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: synthetic construct

<400> SEQUENCE: 1
ccaaaaaaga aaagaaaagt t                                                            21

<210> SEQ ID NO 2
<211> LENGTH: 27
<212> TYPE: DNA
<213> ORGANISM: Artificial Sequence
<220> FEATURE:
<223> OTHER INFORMATION: synthetic construct

<400> SEQUENCE: 2
ctaccgccgc tggaaagact gactctg                                                     27
```

RIPK2 INHIBITION FOR THE TREATMENT OF CANCER

CROSS-REFERENCE TO RELATED APPLICATIONS

This application is a National Phase of International Application No. PCT/US2021/024740, filed Mar. 29, 2021 which designated the U.S. and that International Application was published under PCT Article 21 (2) in English, which claims priority to and benefit of U.S. Provisional Patent Application No. 63/001,951, filed Mar. 30, 2020, the entirety of which is hereby incorporated by reference.

STATEMENT REGARDING FEDERALLY SPONSORED RESEARCH OR DEVELOPMENT

This invention was made with government support under Grant No. W81XWH-18-1-0476 awarded by Department of Defense. The government has certain rights in the invention.

FIELD OF INVENTION

This invention relates to the treatment of cancer, including metastatic prostate cancer, breast cancer, liver cancer, bladder cancer, and melanoma, the diagnosis of cancer, and personalized medicine by the selection of patients who will benefit from the cancer treatment of the present invention.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Each year, prostate cancer kills about 350,000 men around the globe, including about 33,000 men in the United States. Prostate cancer is a very heterogeneous disease. When prostate cancer cells spread to distant organs, they can be treated by androgen deprivation therapies but almost invariably become resistant to treatment. Many attempts have been made to prolong the lives and/or improve the quality of life of prostate cancer patients. In the past, a number of drugs have been approved by the FDA to treat lethal prostate cancer. However, most of them only target the androgen receptor signaling pathway. In addition, even with the newly approved drugs, most patients with metastatic castration-resistant prostate cancer (mCRPC) can only live for 2-3 years after diagnosis. Therefore, there is an urgent need to identify and target novel drug targets whose pharmacological inhibition can benefit at least a significant subset of patients with lethal prostate cancer, as well as other cancers. This invention addresses this unmet clinical need.

SUMMARY OF THE INVENTION

The following embodiments and aspects thereof are described and illustrated in conjunction with compositions and methods which are meant to be exemplary and illustrative, not limiting in scope.

These objectives are achieved by various embodiments of the present invention.

Various embodiments of the present invention provide for a method of treating cancer or inhibiting metastasis in a subject in need thereof, comprising: administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

In various embodiments, the RIPK2 inhibitor can be ponatinib, and the cancer is not chronic myeloid leukemia (CML), or Philadelphia chromosome-positive (PH+) acute lymphoblastic leukemia (ALL).

In various embodiments, the RIPK2 inhibitor can be ponatinib, GSK-583, ODS-101, or a combination thereof. In various embodiments, the RIPK2 inhibitor can be GSK2983559, regorafenib, sorafenib, or a combination thereof.

In various embodiments, the cancer can be prostate cancer. In various embodiments, the cancer can be advance prostate cancer. In various embodiments, the cancer can be breast cancer or melanoma. In various embodiments, the cancer can be breast cancer, liver cancer, bladder cancer, or melanoma.

In various embodiments, the subject has been determined to have an increased expression of RIPK2 in cancer cells, as compared to non-cancerous cells. In various embodiments, the subject has been determined to have a RIPK2 copy number gain, a MYC copy number gain, or a RIPK2/MYC copy number co-gain in cancer cells as compared to non-cancerous cells. In various embodiments, the subject has been determined to have a RIPK2 copy number amplification, a MYC copy number amplification, or a RIPK2/MYC copy number co-amplification in cancer cells as compared to non-cancerous cells.

In various embodiments, the cancer can be uveal melanoma, liver hepatocellular carcinoma, colorectal adenocarcinoma, breast invasive carcinoma, prostate adenocarcinoma, lung adenocarcinoma, sarcoma, head and neck squamous cell carcinoma, diffuse large B-Cell lymphoma, bladder urothelial carcinoma, cholangiocarcinoma, kidney chromophobe, lung squamous cell carcinoma, esophageal adenocarcinoma, stomach adenocarcinoma, ovarian serous cystadenocarcinoma, cervical squamous cell carcinoma, skin cutaneous melanoma, testicular germ cell tumor, mesothelioma, kidney renal clear cell carcinoma, uterine carcinosarcoma, acute myeloid leukemia, uterine corpus endometrial carcinoma, kidney renal papillary cell carcinoma, glioblastoma multiforme, brain lower grade glioma, adrenocortical carcinoma, thymoma, thyroid carcinoma, pheochromocytoma and paraganglioma, or pancreatic adenocarcinoma.

In various embodiments, the method comprises treating the cancer. In various embodiments, the method comprises inhibiting metastasis.

Various embodiments of the present invention provide for a method of selecting a subject for treatment with a receptor-interacting protein kinase 2 (RIPK2) inhibitor, comprising: obtaining a biological sample from the subject; detecting, in the biological sample, a copy number gain, a copy number amplification or increased expression in RIPK2, MYC or both; selecting the RIPK2 inhibitor for treating the subject, wherein if the RIPK2 inhibitor is ponatinib, the subject does not have chronic myeloid leukemia (CML), or Philadelphia chromosome-positive (PH+) acute lymphoblastic leukemia (ALL).

In various embodiments, the subject has been determined to have a RIPK2 copy number gain, a MYC copy number gain, or a RIPK2/MYC copy number co-gain. In various embodiments, the subject has been determined to have a RIPK2 copy number amplification, a MYC copy number amplification, or a RIPK2/MYC copy number co-amplification. In various embodiments, the subject has been determined to have increased expression in RIPK2, MYC, or both.

In various embodiments, the method can further comprise administering the RIPK2 inhibitor to the subject.

In various embodiments, the RIPK2 inhibitor can be ponatinib, GSK-583, ODS-101, or a combination thereof. In various embodiments, the RIPK2 inhibitor can be GSK2983559, regorafenib, sorafenib, or a combination thereof.

In various embodiments, the subject can have cancer. In various embodiments, the cancer can be prostate cancer. In various embodiments, the cancer can be advanced prostate cancer. In various embodiments, the cancer can be breast cancer or melanoma. In various embodiments, the cancer can be breast cancer, liver cancer, bladder cancer, or melanoma. In various embodiments, the cancer can be uveal melanoma, liver hepatocellular carcinoma, colorectal adenocarcinoma, breast invasive carcinoma, prostate adenocarcinoma, lung adenocarcinoma, sarcoma, head and neck squamous cell carcinoma, diffuse large B-Cell lymphoma, bladder urothelial carcinoma, cholangiocarcinoma, kidney chromophobe, lung squamous cell carcinoma, esophageal adenocarcinoma, stomach adenocarcinoma, ovarian serous cystadenocarcinoma, cervical squamous cell carcinoma, skin cutaneous melanoma, testicular germ cell tumor, mesothelioma, kidney renal clear cell carcinoma, uterine carcinosarcoma, acute myeloid leukemia, uterine corpus endometrial carcinoma, kidney renal papillary cell carcinoma, glioblastoma multiforme, brain lower grade glioma, adrenocortical carcinoma, thymoma, thyroid carcinoma, pheochromocytoma and paraganglioma, or pancreatic adenocarcinoma.

In various embodiments, the biological sample can comprise cancer cells.

Other features and advantages of the invention will become apparent from the following detailed description, taken in conjunction with the accompanying drawings, which illustrate, by way of example, various features of embodiments of the invention.

BRIEF DESCRIPTION OF THE FIGURES

Exemplary embodiments are illustrated in referenced figures. It is intended that the embodiments and figures disclosed herein are to be considered illustrative rather than restrictive.

Figure 14:
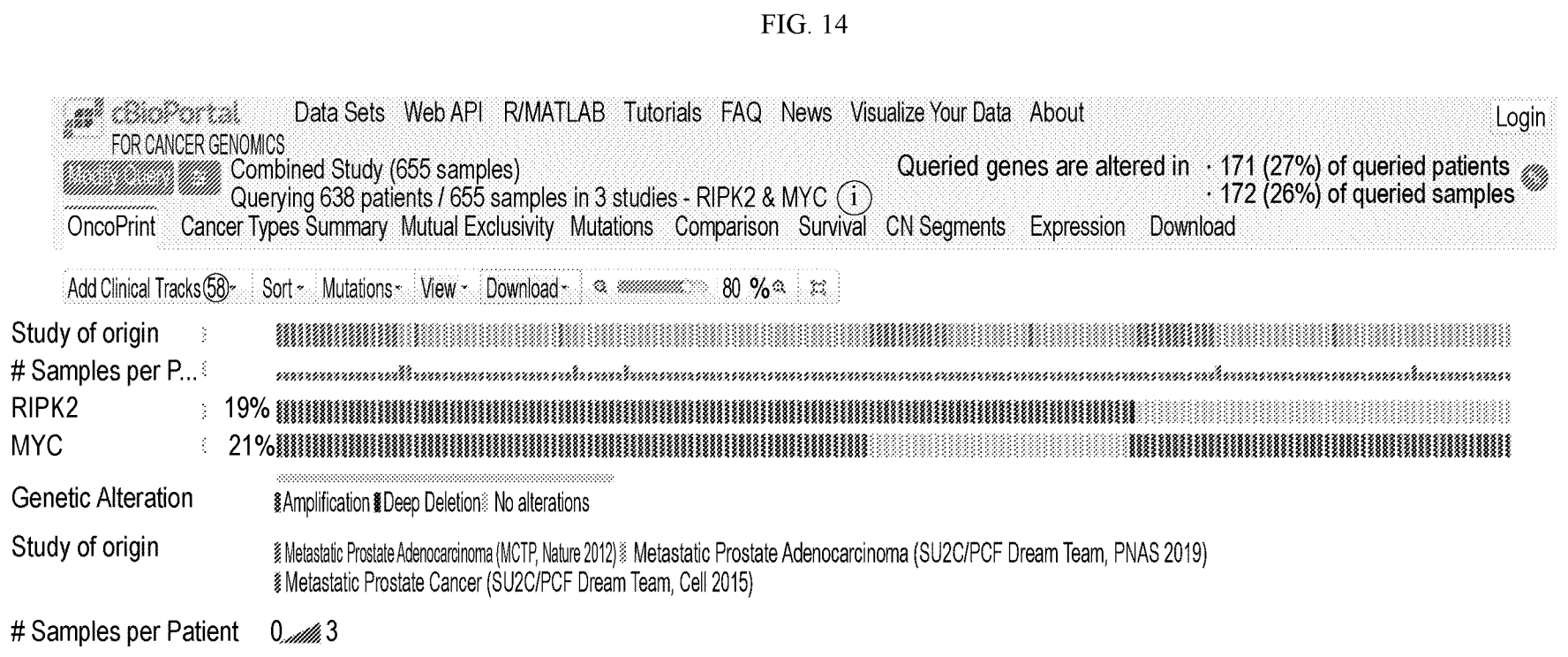

FIG. 14 shows a frequent co-amplification of the RIPK2 and MYC genes in metastatic castration-resistant prostate cancer tissue specimens (n=655). RIPK2 was amplified in 19% of mCPRC, MYC in 21% of mCPRC, and both in 13% of mCRPC.

FIG. 18 (panels A-O) shows that RIPK2 is a Potent Activator and Stabilizer of c-Myc. (A) Venn diagrams of protein groups that are upregulated (upper) or downregulated (lower) in the three RIPK2-KO PC3 single-cell clones (#4, #12, and #16), compared with control cells. (B) Heatmap of the 652 overlapping differentially expressed protein groups in the control or RIPK2-KO PC3 clones (n=6 per group). (C) Scatter plot of putative regulators upstream of the 652 differentially expressed proteins. The activation Z scores and p values were computed by Ingenuity Pathway Analysis. (D) Bar plot of the relative MYC luciferase reporter activity in PC3 cells under the indicated conditions. (E) Scatter plots of RIPK2-induced activity Z scores against Hallmark_MYC_Targets_V1 gene set activity Z scores in the PCTA (upper) and TCGA (lower) cohorts. (F) Venn diagram of the genes contained in the RIPK2-induced protein signature (i.e., the 243 protein groups downregulated by RIPK2-KO) and those in the Hallmark_MYC_Targets_V1 gene set. (G) Representative immunoblots of the indicated proteins of total lysates from control or RIPK2-KO (by gRNA3 or gRNA10) PC cells. (H) Representative immunoblots of the indicated proteins of total lysates from RIPK2-KO PC3 cells transiently transfected with the indicated amounts of the RIPK2m4 plasmid. (I) Representative immunoblots of the indicated proteins of total lysates from parental cells transiently co-transfected with vector or RIPK2 (2 μg plasmid per cell line except 0.5 μg for HEK293T) and MYC (1 μg per cell line except 0.5 μg for HEK293T) plasmids. (J) Pie chart of the percentages of mCRPC tissue specimens (n=655) with RIPK2 and MYC gene co-amplification/gain. (K) Representative immunoblots of the indicated proteins of total lysates from RIPK2-KO DU145 cells transiently transfected with RIPK2 (0.5 μg) and/or MYC (0.5 μg) plasmids. (L) Representative immunoblots of the indicated proteins of total lysates from RIPK2-KO HEK293T cells transiently co-transfected with the indicated amounts of RIPK2 plasmid and 0.5 μg MYC plasmid. (M) RIPK2-KO HEK293T cells were transiently co-transfected with the indicated amounts of RIPK2 plasmid and 0.5 μg MYC plasmid. MYC mRNA levels were measured by quantitative PCR (n=9), while c-Myc (n=3) and p-c-Myc-Ser62 (n=3) protein levels were measured by IB analyses as shown in (L). (N) c-Myc was immunoprecipitated from control or RIPK2-KO cells (clones #4 and #12). Immunoprecipitation product and total lysates were analyzed by IB for the indicated proteins. (0) Bar graph of the half-lives of the c-Myc protein in control and RIPK2-KO PC3 cells (n=4). P values were determined by unpaired two-tailed Student's t-test (D and O) or using a t-distribution with n−2 degrees of freedom (E) (*P<0.05, P<0.01, and *P<0.001). Data are shown as Mean±SEM. Numbers in parentheses represent numbers of biological replicates.

Figure 19:
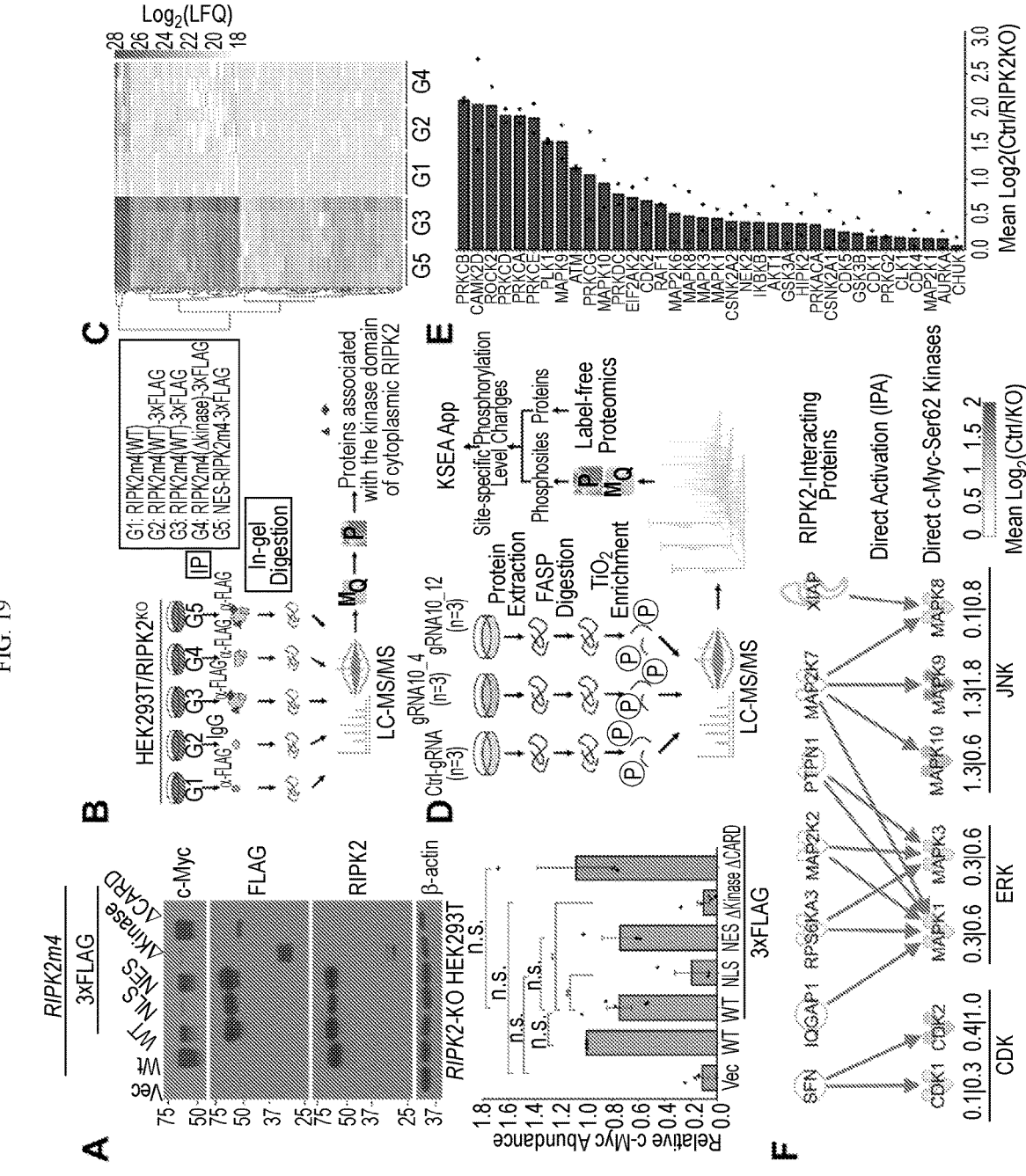

FIG. 19 (panels A-F) depicts Integrative Proteomics Analysis Identifies Candidate Kinase Pathways Mediating RIPK2 Phosphorylation of c-Myc-Ser62. (A) Representative immunoblots (upper) and quantification (lower) of c-Myc in RIPK2-KO HEK293T cells transiently transfected with the indicated plasmids. (B) Schematic of the IP-MS-based interactome analysis. RIPK2-KO HEK293T cells were transiently transfected with the indicated forms of plasmids (in box). Protein complexes were immunoprecipitated using an anti-FLAG antibody or an IgG control. Immunoprecipitated protein complexes were analyzed by in-gel digestion followed by mass spectrometric analysis. Raw files were analyzed by MaxQuant and Perseus to identify proteins associated with the kinase domain of cytoplasmic RIPK2. (C) Heatmap of the 219 protein candidates specifically associated with the kinase domain of cytoplasmic RIPK2. Gray indicates zero label-free quantification (LFQ) intensities. (D) Schematic of the label-free phosphoproteomics analysis. Proteins were extracted from control and RIPK2-KO PC3 cells and digested into tryptic peptides using FASP (filter-aided sample preparation). Phosphopeptides were enriched by titanium dioxide (TiO2) and analyzed by LC-MS/MS. Raw files were analyzed by Max-Quant (MQ) to identify phosphopeptides, by Perseus to identify significantly differentially phosphorylated peptides, and by kinase-substrate enrichment analysis (KSEA) to identify differentially activated kinases. (E) Bar plot of the inferred activity changes of candidate kinases activated by RIPK2. For each kinase, the two dots represent Log 2Ratios in control PC3 cells relative to those in RIPK2-KO PC3 clones (#4 and #12), respectively. (F) Activation network connecting RIPK2-interacting protein candidates (identified by the interactome profiling) with direct c-Myc-Ser62 kinases downstream of RIPK2 (identified by the phosphoproteomics analysis). The numbers indicate kinase activities in control PC3 cells relative to those in RIPK2-KO PC3 clone #4 (left) or clone #12 (right).

Figure 20:
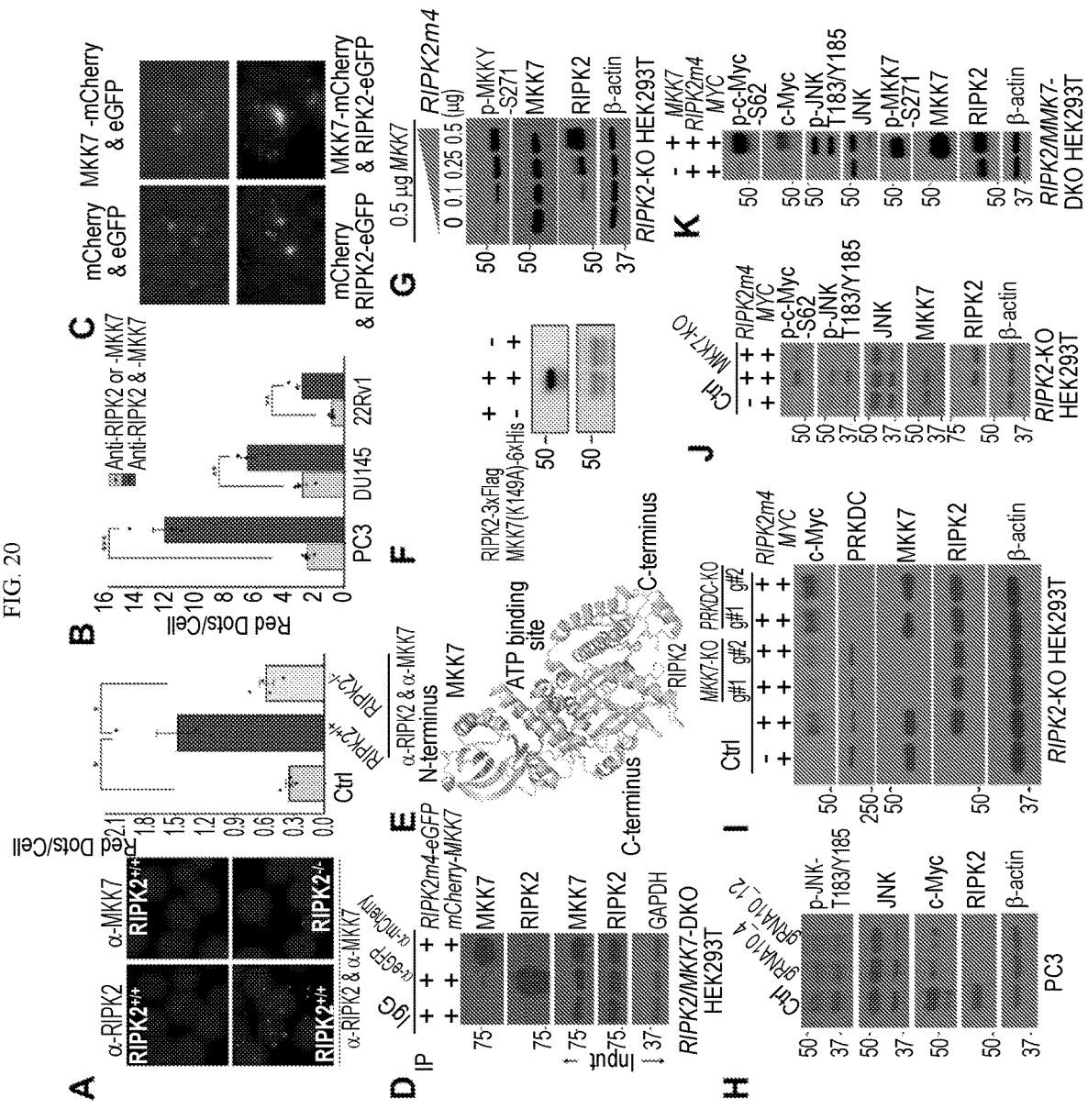

FIG. 20 (panels A-K) shows that MKK7 is a Major Mediator of RIPK2 Phosphorylation of c-Myc-Ser62. (A) Representative images (left) and quantification (right) of PLA detecting the association of endogenous RIPK2 and MKK7 in HEK293T cells (n=4 per group). (B) Bar plot of PLA detecting the association of endogenous RIPK2 and MKK7 in parental PC cells (n=4 per group). (C) Representative images of fluorescence colocalization of RIPK2 and MKK7 ectopically expressed in RIPK2/MKK7-DKO HEK293T cells. (D) Representative images of Co-IP analysis detecting the association of RIPK2 and MKK7 ectopically expressed in RIPK2- and MKK7-KO HEK293T cells. (E) Three-dimensional structural model of direct RIPK2 and MKK7 association in ribbon representation. (F) Representative images of radioactive in vitro RIPK2 kinase assay detecting RIPK2 phosphorylation of MKK7, using kinase-dead MKK7 as substrate (n=3). The upper and lower panels show representative autoradiography and Coomassie blue-stained gel images, respectively. (G) Representative immunoblots of the indicated proteins in total lysates of RIPK2-KO HEK293T cells transiently transfected with the indicated amounts of RIPK2m4 plasmid. 0.5 μg MKK7 was co-transfected to enable the detection of p-MKK7. (H) Representative immunoblots of the indicated proteins in total lysates of control and RIPK2-KO PC3 cells. (I) Representative immunoblots of the indicated proteins in total lysates of RIPK2-KO HEK293T cells under the indicated conditions. The g #1 and g #2 represent two independent gRNAs for gene knockout. (J) Representative immunoblots of the indicated proteins in total lysates of RIPK2-KO HEK293T cells under the indicated conditions. (K) Representative immunoblots of the indicated proteins in total lysates of RIPK2/MKO-DKO HEK293T cells under the indicated conditions. P values were determined by unpaired two-tailed Student's t-test (A and B) (*P<0.05, P<0.01, and *P<0.001). Data are shown as Mean±SEM.

Figure 21:
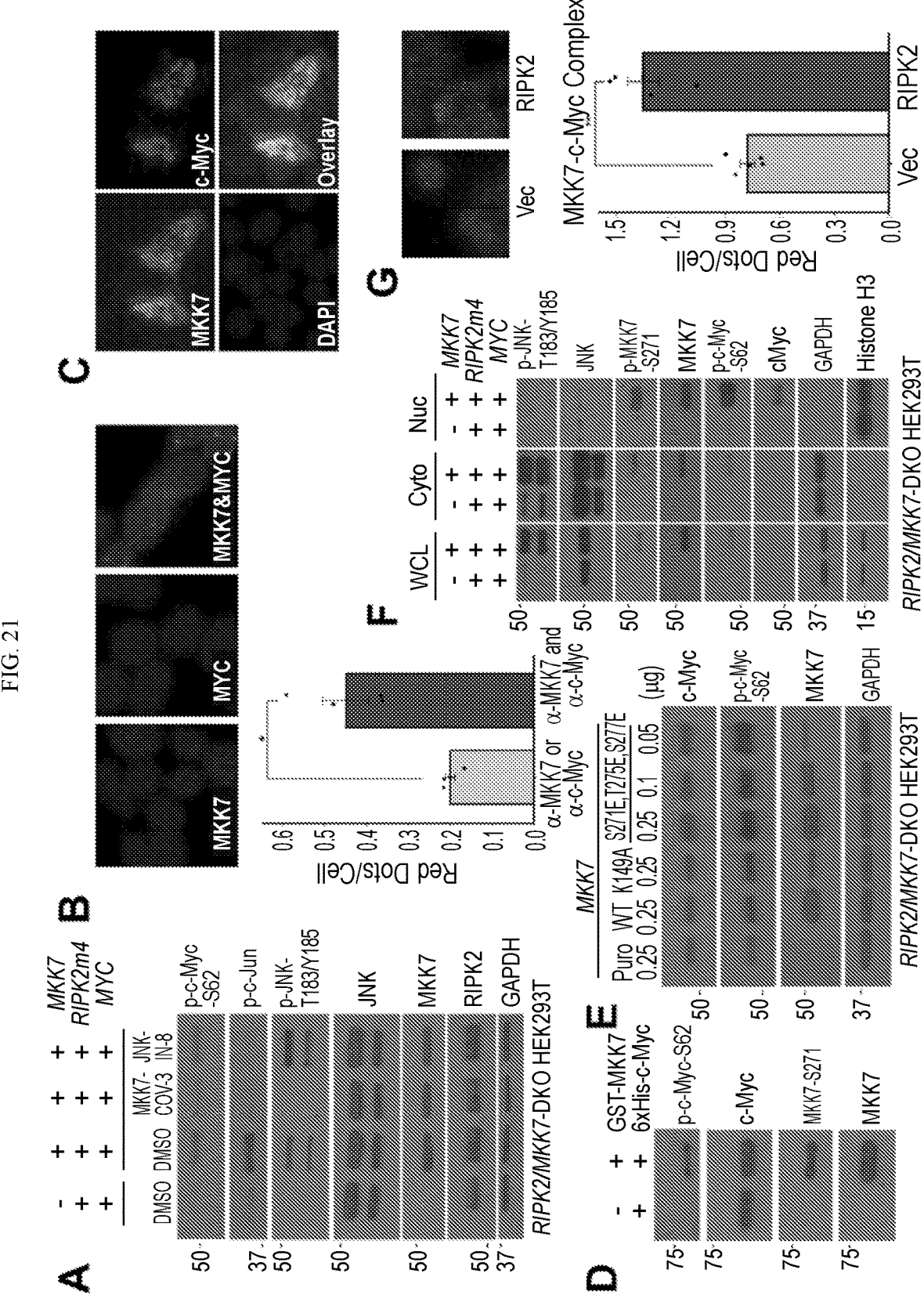

FIG. 21 (panels A-G) shows that MKK7 is a Direct c-Myc-Ser62 Kinase. (A) Representative immunoblots of the indicated proteins in total lysates of HEK293T cells with RIPK2- and MKK7-double knockout, which were transiently co-transfected with 0.5 μg MYC, 0.5 μg RIPK2m4, and 0.1 μg MAP2K7 or vector plasmids and then treated with vehicle control, MKK7-COV-3 (25 μM), or JNK-IN-8 (1 μM) in 10% FBS-containing medium for 2 h. (B) Representative images (upper) and quantification (lower) of PLA detecting the association of endogenous MKK7 and c-Myc in HEK293T cells (n=4 per group). (C) Representative images of immunofluorescence colocalization of MKK7 and c-Myc in RIPK2/MKK7-DKO HEK293T cells, which were transiently co-transfected with RIPK2m4, MKK7-His, and MYC plasmids. (D) Representative immunoblots of the indicated proteins after in vitro kinase reactions. (E) Representative immunoblots of the indicated proteins in total lysates of RIPK2/MKK7-DKO HEK293T cells, which were transiently transfected with the indicated forms of MKK7 plasmids or vector control. (F) Representative immunoblots of the indicated proteins in total lysates, cytoplasmic fraction, and nuclear fraction of RIPK2/MKK7-DKO HEK293T cells, which were transiently co-transfected with RIPK2m4, MYC, and MKK7 or vector control. (G) Representative images (upper) and quantification (lower) of PLA detecting the MKK7-c-Myc complex in RIPK2-KO HEK293T cells, which were transiently transfected with MYC and RIPK2m4 or vector control (n=5 per group). P values were determined by unpaired two-tailed Student's t-test (B and G) (*p<0.05, **p<0.01). Data are Mean±SEM.

Figure 22:
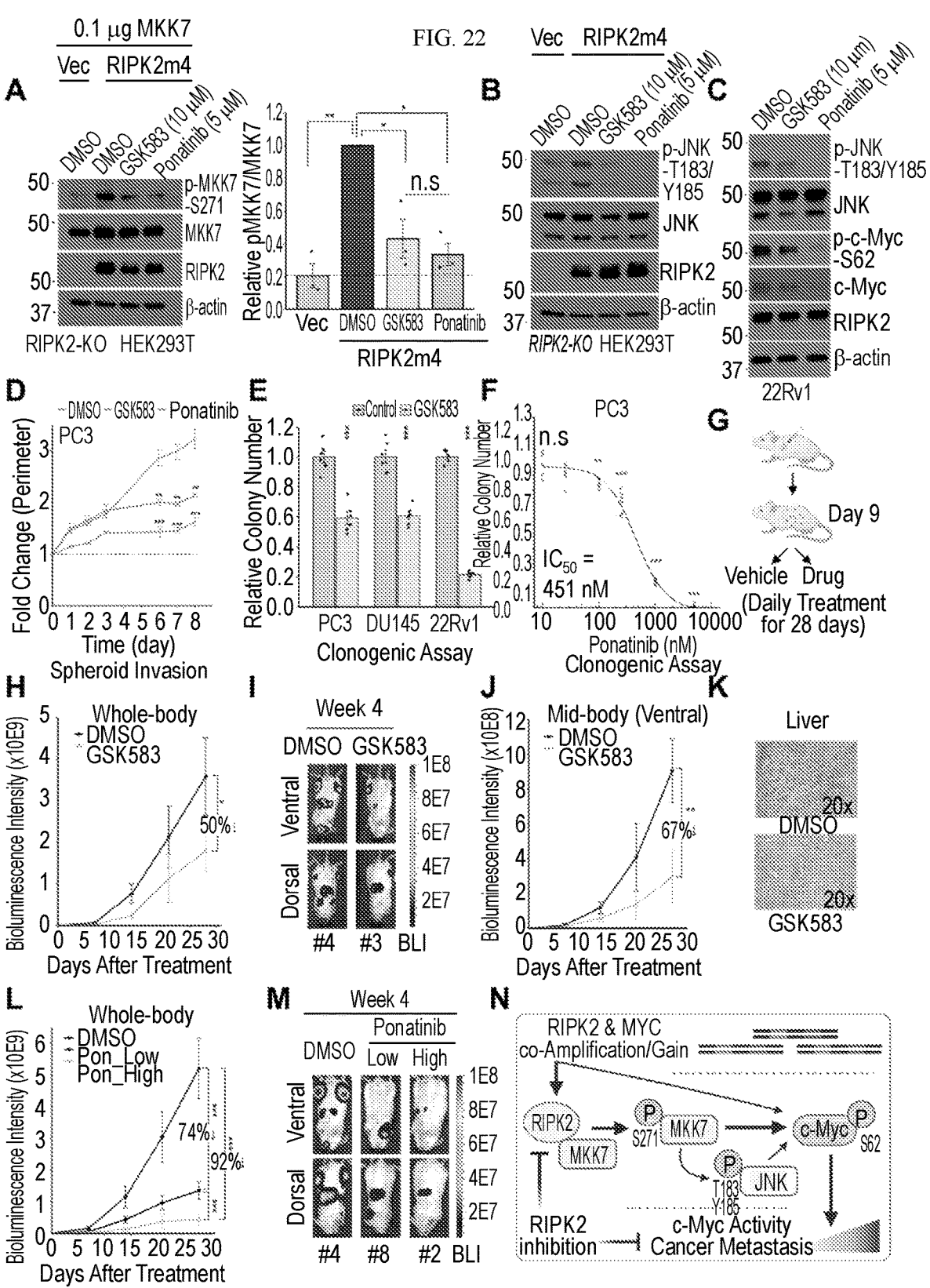

FIG. 22 (panels A-N) shows that Pharmacological Inhibition of RIPK2 Attenuates RIPK2/MKK7/c-Myc Signaling and Suppresses PC Metastasis. (A) Representative immunoblots (left) and quantification (right) of p-MKK7-5271 in total lysates of RIPK2-KO HEK293T cells under the indicated conditions. Cells were treated with vehicle, 10 μM GSK583, or 5 μM Ponatinib in 10% FBS-containing medium for 2 h. (B) Representative immunoblots of the indicated proteins in total lysates of RIPK2-KO HEK293T cells under the indicated conditions. Cells were treated with vehicle control, 10 μM GSK583, or 5 μM Ponatinib in 10% FBS-containing medium for 2 h. (C) Representative immunoblots of the indicated proteins in total lysates of 22Rv1 cells treated with vehicle control, 10 μM GSK583, or 5 μM Ponatinib in serum-free medium for 2 h. (D) Quantification of 3D spheroid invasion assays of PC3 cells treated with vehicle control, 10 μM GSK583, or 5 μM Ponatinib (n=6 per group). (E) Bar plot of anchorage-dependent colony formation of PC3, DU145, and 22Rv1 cells treated with vehicle control or 10 μM GSK583 (n=6 per group). (F) Drug response curve of anchorage-dependent colony formation of PC3 cells treated with vehicle control or the indicated concentrations of Ponatinib (n=6 per group). (G) Schematic diagram of drug treatment for the inhibition of PC metastasis in vivo. Mice were intracardially injected with luciferase-tagged 22Rv1 cells. On day 9, metastases were imaged by BLI and mice were separated into two or three groups, which were daily treated with vehicle control or a RIPK2 inhibitor for four weeks. (H) Effect of GSK583 treatment (10 mg/kg/day) on total BLI intensities in mice (vehicle, n=5; GSK583, n=7), starting on day 9 following the intracardiac injection. (I) Representative BLI images of the ventral (upper) and dorsal (lower) sides of mice treated with vehicle control or GSK583 for 4 weeks. (J) Effect of GSK583 treatment (10 mg/kg/day) on BLI intensities in the liver region (ventral-side mid-body) of mice (vehicle, n=5; GSK583, n=7), starting on day 9 following the intracardiac injection. (K) Representative H&E images of livers in mice treated with vehicle control (upper) or GSK583 (lower). (L) Effect of low-dose (6 mg/kg/day) or high-dose (30 mg/kg/day for 10 days followed by 15 mg/kg/day for 18 days) Ponatinib treatment on total BLI intensities in mice (vehicle, n=6; low-dose Ponatinib, n=8; high-dose Ponatinib, n=7), starting on day 9 following the intracardiac injection. (M) Representative BLI images of the ventral (upper) and dorsal (lower) sides of mice treated with vehicle control, low-dose Ponatinib, or high-dose Ponatinib for 4 weeks. (N) Simplified schematic illustration of the druggable RIPK2/MKK7 (/JNK)/c-Myc signaling pathway, which is frequently altered in PC tumors and required for PC metastasis. P values were determined by unpaired two-tailed Student's t-test (A, D, E, and F) or two-way ANOVA (H, J, and L) (n.s.: not significant, *p<0.05, p<0.01, *p<0.001). Data are Mean±SEM.

Figure 23:
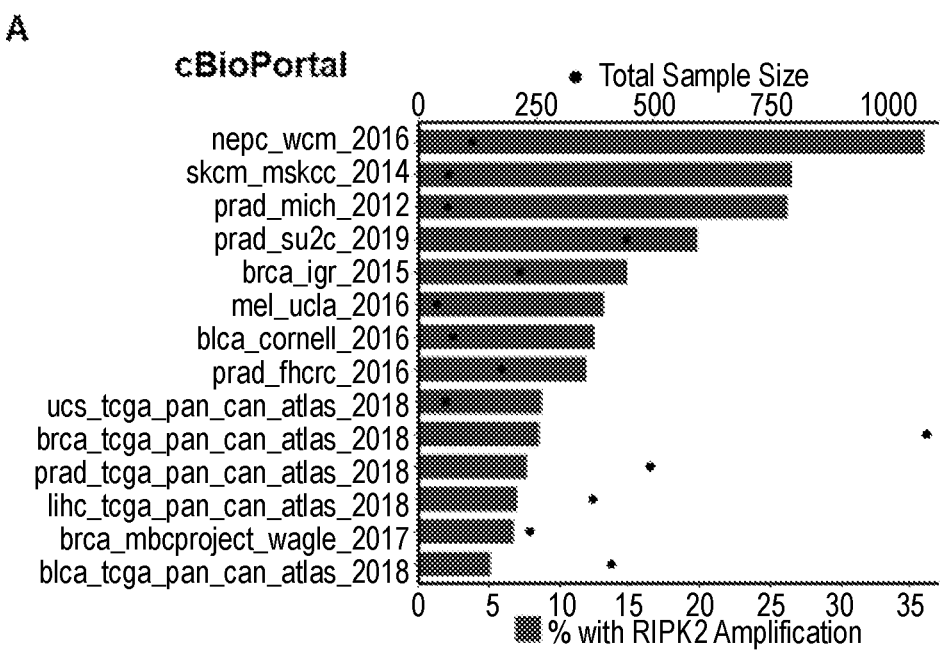
Figure 23:
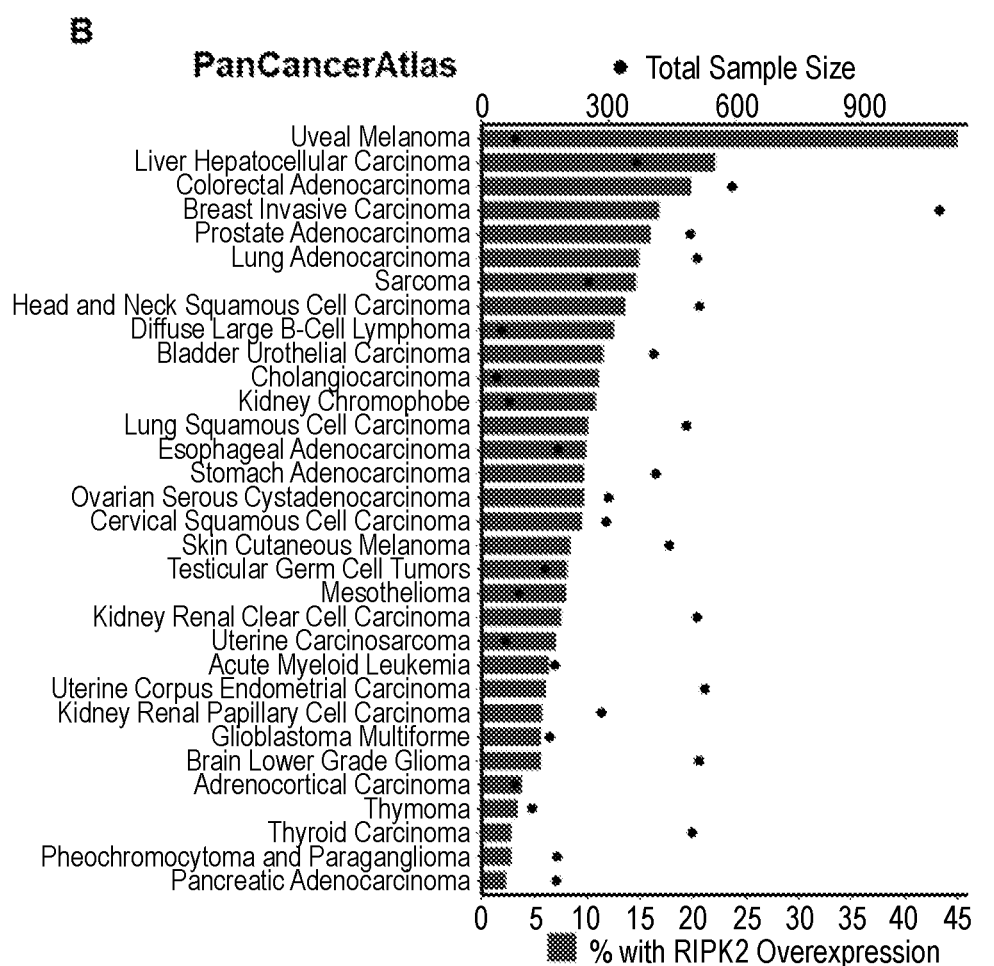

FIG. 23 (panels A-B) shows that RIPK2 is Frequently Amplified or Overexpressed in Multiple Cancer Types. (A) Bar plot of the percentages of tumors with RIPK2 gene amplification in different cancer genomics studies (retrieved from the cBioPortal). The "total sample size", shown in black dots, represents the number of tissue specimens with copy number data. Bar lengths correspond to the percentages of tumors with RIPK2 amplification. (B) Bar plot of the percentages of tumors with RIPK2 mRNA overexpression (Z>2, relative to diploid samples) in the 32 TCGA PanCancer Atlas studies. The "total sample size", shown in black dots, represents the number of tissue specimens with mRNA expression data. Bar lengths correspond to the percentages of tumors with RIPK2 Mrna overexpression (Z>2).

Figure 24:
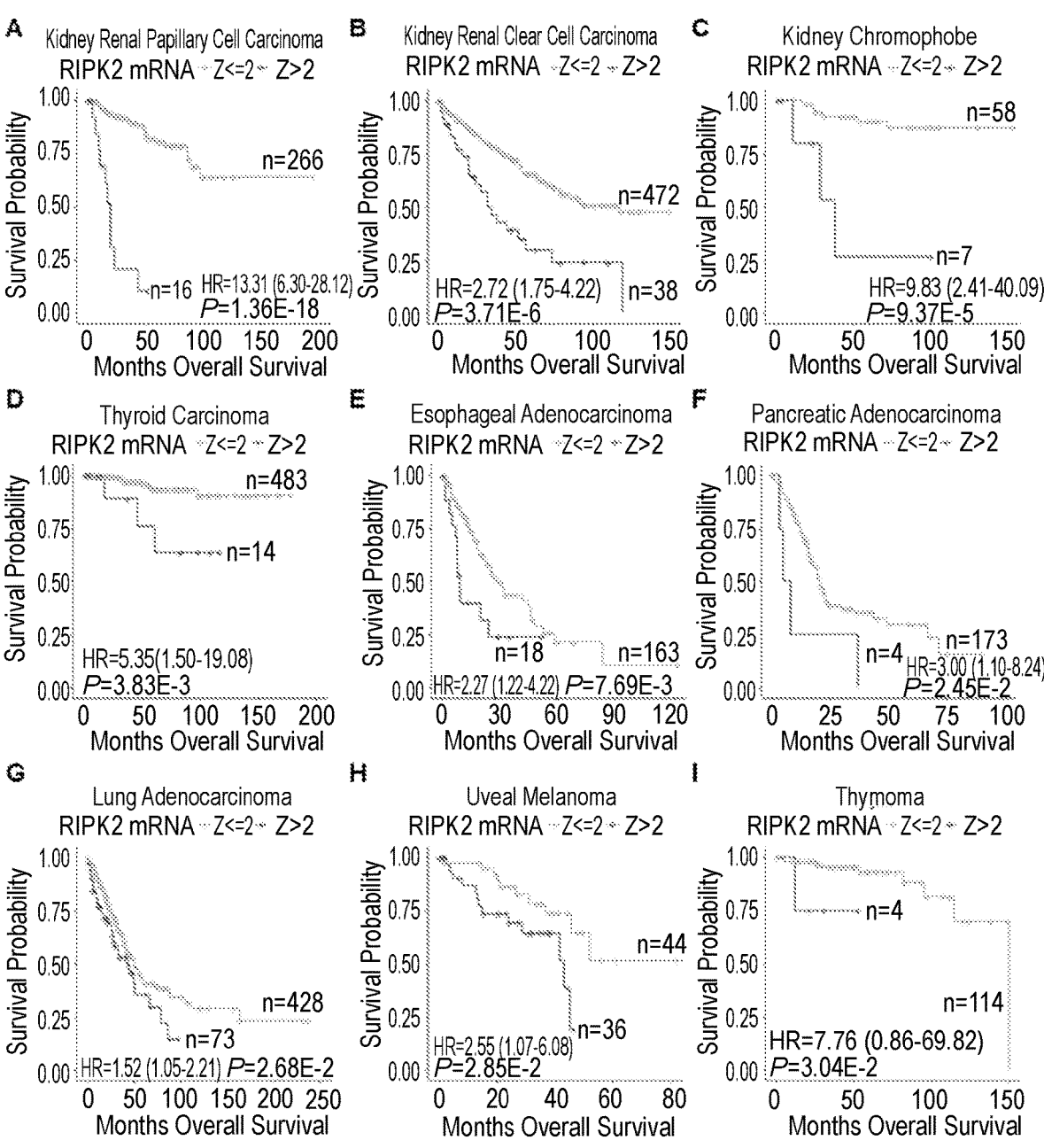

FIG. 24 (panels A-I) shows that RIPK2 Overexpression is Associated with Significantly Shorter Overall Survival in Nine Cancer Types in the TCGA PanCancer Atlas. (A) Kaplan-Meier overall survival analysis of kidney papillary cell carcinoma (n=282). (B) Kaplan-Meier overall survival analysis of kidney clear cell carcinoma (n=510). (C) Kaplan-Meier overall survival analysis of kidney chromophobe (n=65). (D) Kaplan-Meier overall survival analysis of thyroid carcinoma (n=497). (E) Kaplan-Meier overall survival analysis of esophageal adenocarcinoma (n=181). (F) Kaplan-Meier overall survival analysis of pancreatic adenocarcinoma (n=177). (G) Kaplan-Meier overall survival analysis of lung adenocarcinoma (n=501). (H) Kaplan-Meier overall survival analysis of uveal melanoma (n=80). (I) Kaplan-Meier overall survival analysis of thymoma (n=118). Patients were stratified based on whether RIPK2 is significantly (Z>2, normalized against diploid samples) overexpressed. P values were determined by two-sided log-rank test. HR, hazard ratio (95% confidence interval).

Figure 25:
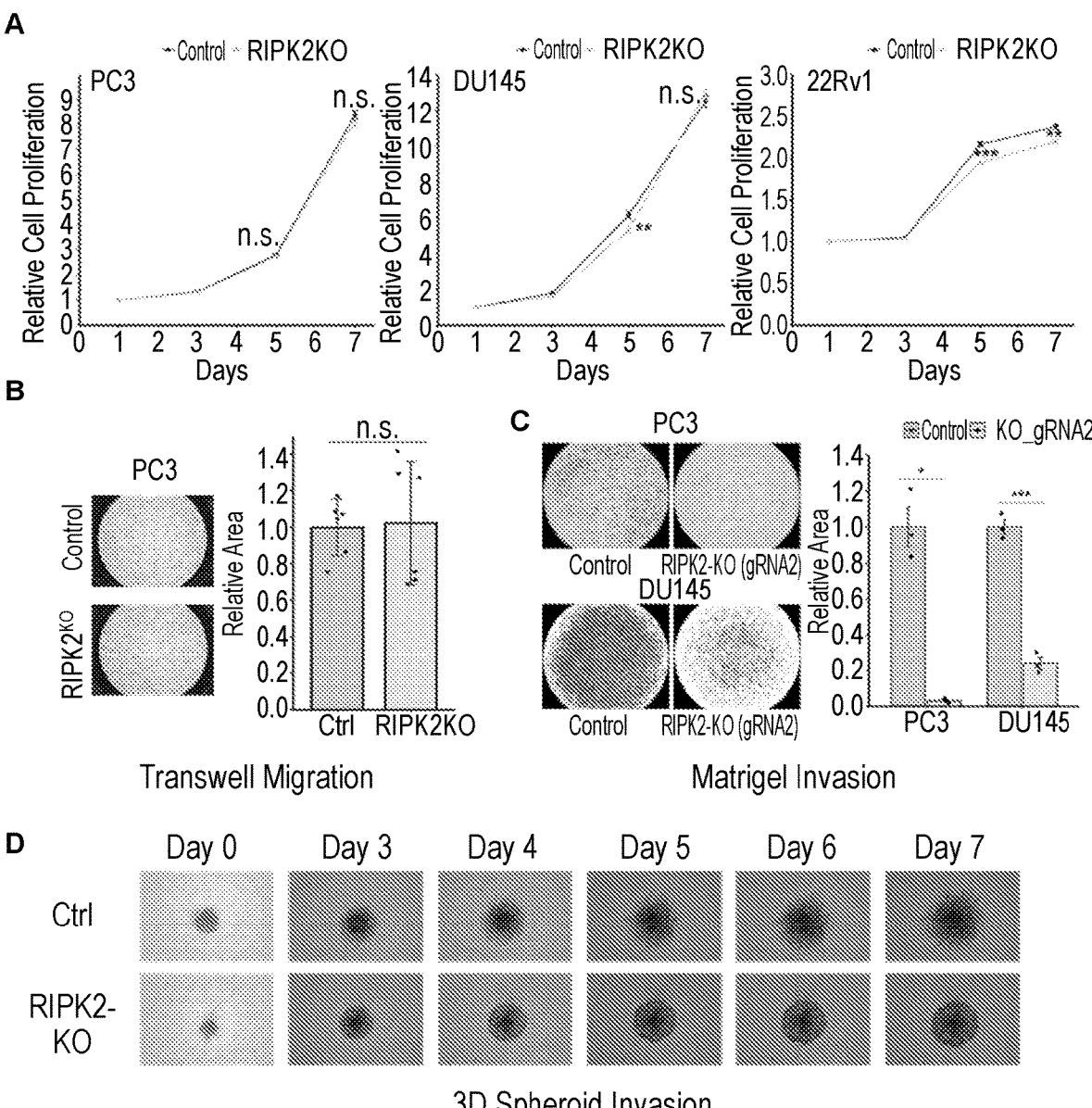

FIG. 25 (panels A-D) RIPK2 Knockout Has a Negligible Effect on PC Cell Proliferation and Migration but Inhibits Invasion In Vitro. (A) Growth curves of control and RIPK2-KO PC3 (left), DU145 (middle), and 22Rv1 (right) cells (n=10 per group). (B) Representative images (left) and quantification (right) of Transwell migration assay of control or RIPK2-KO PC3 cells (n=6 per group). (C) Representative images (left) and quantification (right) of Matrigel invasion assay of control PC cells and cells with RIPK2 knockout by CRISPR/Cas9 using gRNA2 (n=3 per group). (D) Representative images of 3D spheroid invasion assay of control or RIPK2-KO PC3 cells (n=6 per group). P values were determined by Mann-Whitney U test (panel A) or unpaired two-tailed Student's t-test (B and C) (n.s.: not significant, *p<0.05, p<0.01, *p<0.001). Data are Mean±standard deviation (SD).

Figure 26:
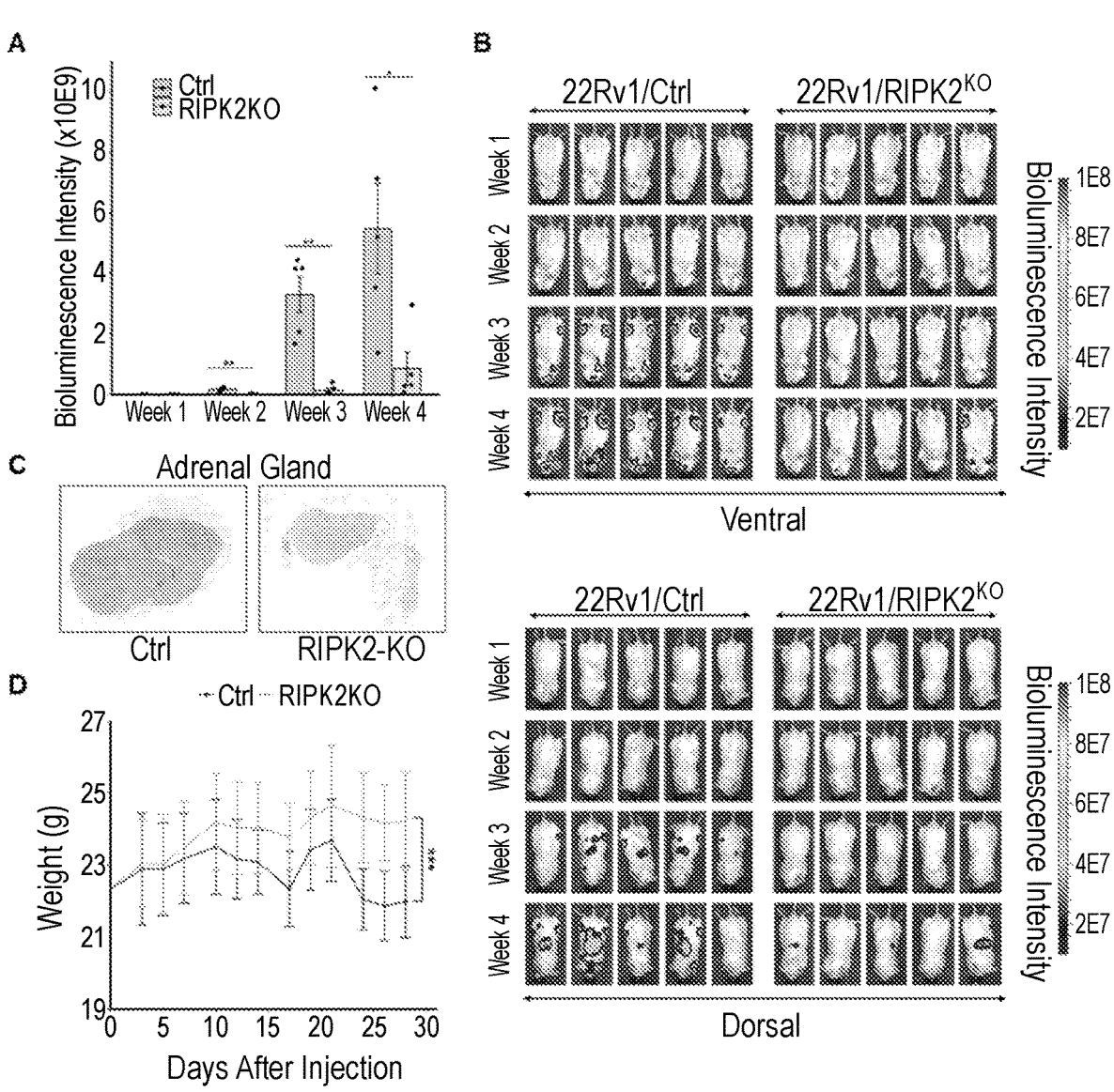

FIG. 26 (panels A-D) shows that RIPK2 Knockout Suppresses PC Metastasis In Vivo. (A) Bar plot of the total bioluminescence intensities at different weeks after the intracardiac injection of luciferase-tagged control or RIPK2-KO 22Rv1 cells. (B) Bioluminescence images of mice from the ventral (upper) and dorsal (lower) sides at different weeks after the intracardiac injection. (C) Representative images of H&E staining of adrenal glands from mice bearing control or RIPK2-KO 22Rv1 cells. (D) Changes in mouse weights following the intracardiac injection. P values were determined by Mann-Whitney U test (A) or two-way ANOVA test (D) (*p<0.05 and **p<0.01). Data are Mean±SEM (n=5) (A and D).

Figure 27:
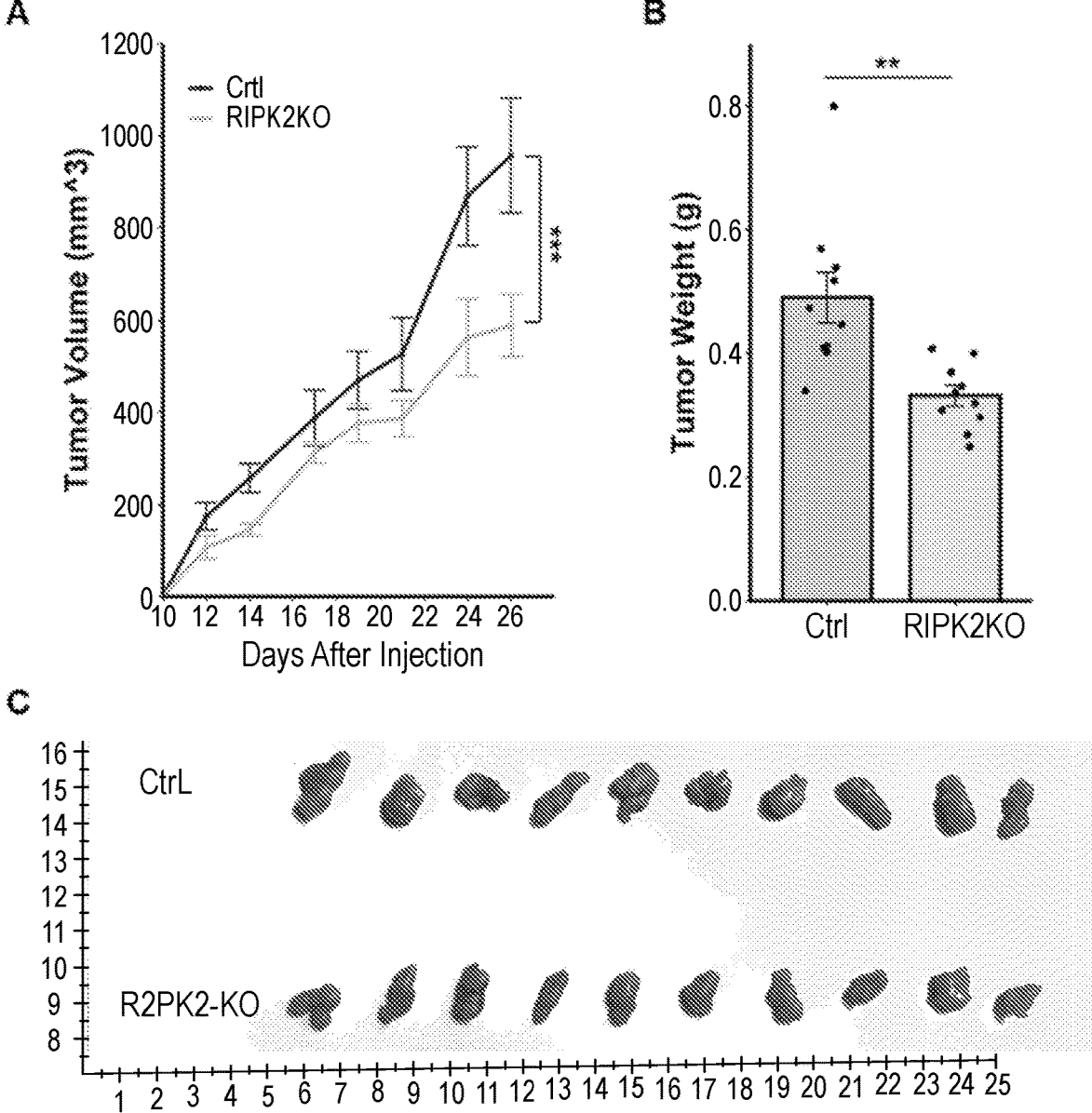

FIG. 27 (panels A-C) shows that RIPK2 Knockout Reduces Tumor Size and Weight. (A) Effect of RIPK2 knockout on 22Rv1 xenograft tumor growth following subcutaneous injection of control or RIPK2-KO 22Rv1 cells into male SCID/beige mice (tumor n=10). (B) Bar plot of the weights of 22Rv1 control or RIPK2-KO tumors on day 26 after subcutaneous injection (n=10). (C) Images of xenograft tumors derived from control (upper) or RIPK2-KO (lower) 22Rv1 cells. Tumors were harvested 26 days after subcutaneous injection. P values were determined by two-way ANOVA (A) or unpaired two-tailed Student's t-test (p<0.01 and *p<0.001). Data are Mean±SEM (n=10) (A and B).

Figure 28:
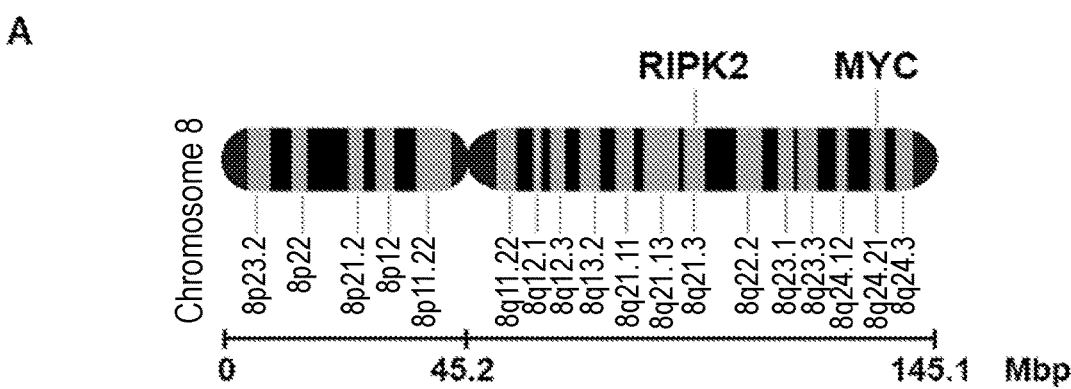
Figure 28:
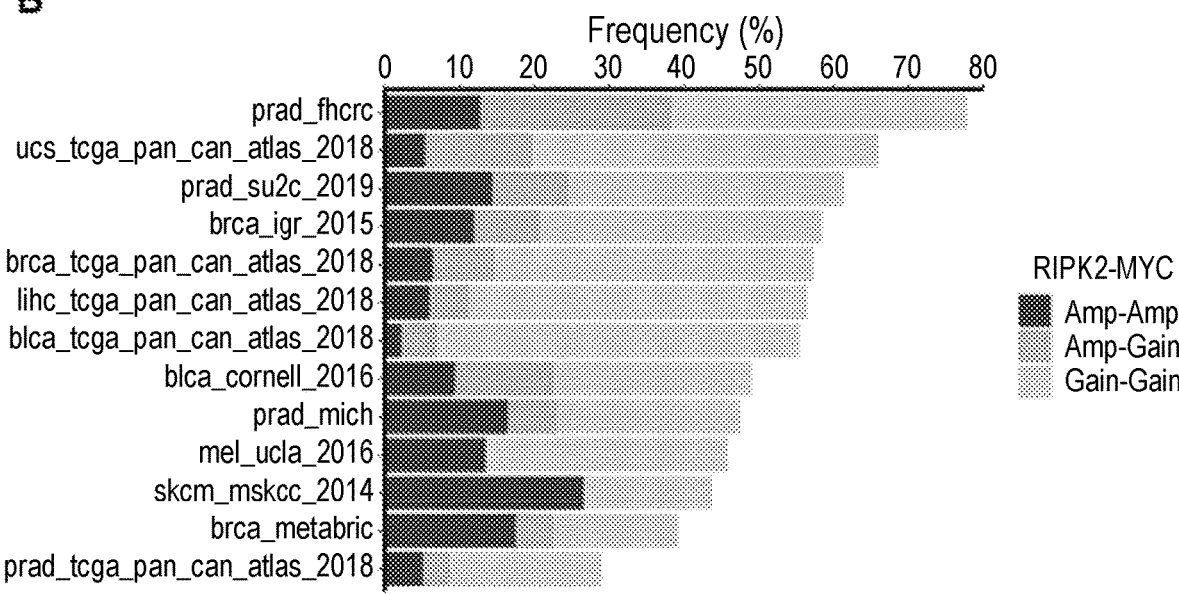
Figure 28:
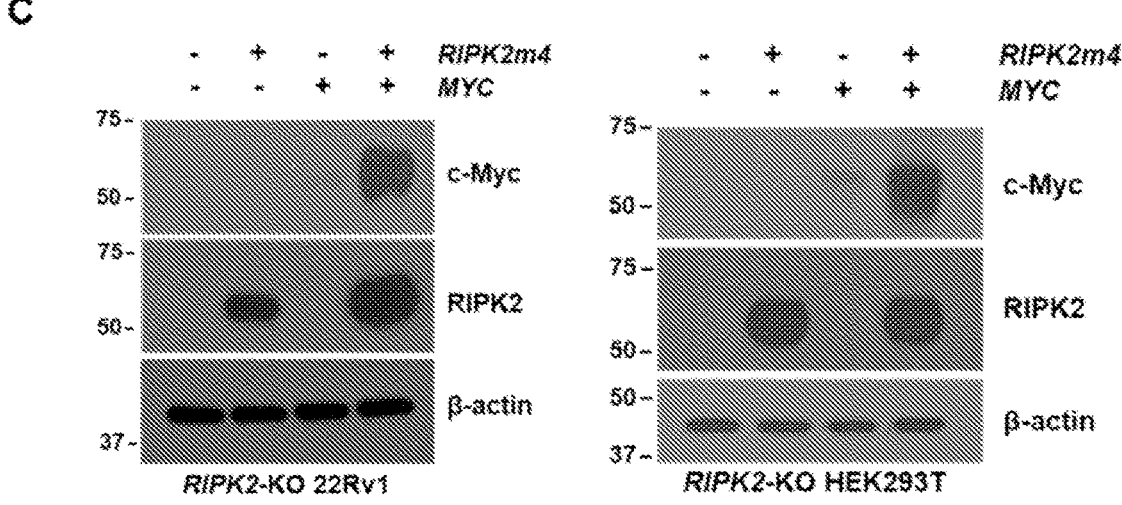

FIG. 28 (panels A-C) shows that the Co-amplification/gain of RIPK2 and MYC Genes is a Frequent Event in Multiple Cancer Types and Synergistically Contributes to c-Myc Protein Abundance. (A) Schematic of RIPK2 and MYC locations on human chromosome 8. (B) Bar plot of the percentages of tumors with RIPK2 and MYC gene co-amplification/gain in different cancer genomics studies (retrieved from the cBioPortal). Different colors show the percentages of tumors with RIPK2-amplification and MYC-amplification (red), with RIPK2-amplification and MYC-gain or RIPK2-gain and MYC-amplification (orange), or with RIPK2-gain and MYC-gain (pink). (C) Representative immunoblots of total lysates of RIPK2-KO 22Rv1 (left) and HEK293T (right) cells under the indicated conditions. 22Rv1 cells were transfected with 1.0 µg RIPK2m4 and/or 1.0 µg MYC plasmids; HEK293T cells were transfected with 0.5 µg RIPK2m4 and/or 0.5 µg MYC plasmids. β-actin was used as a loading control.

Figure 29:
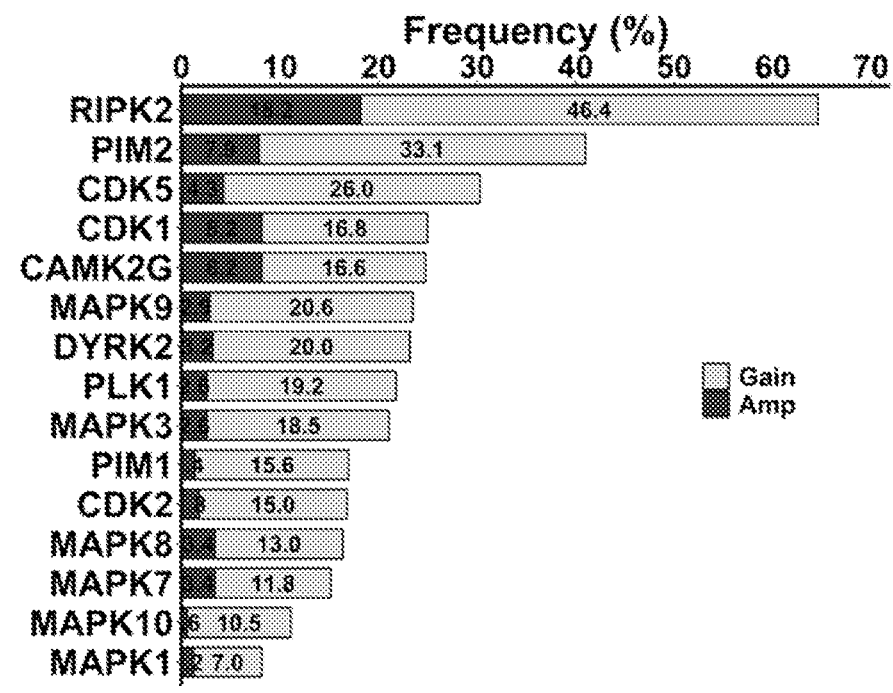
Figure 29:
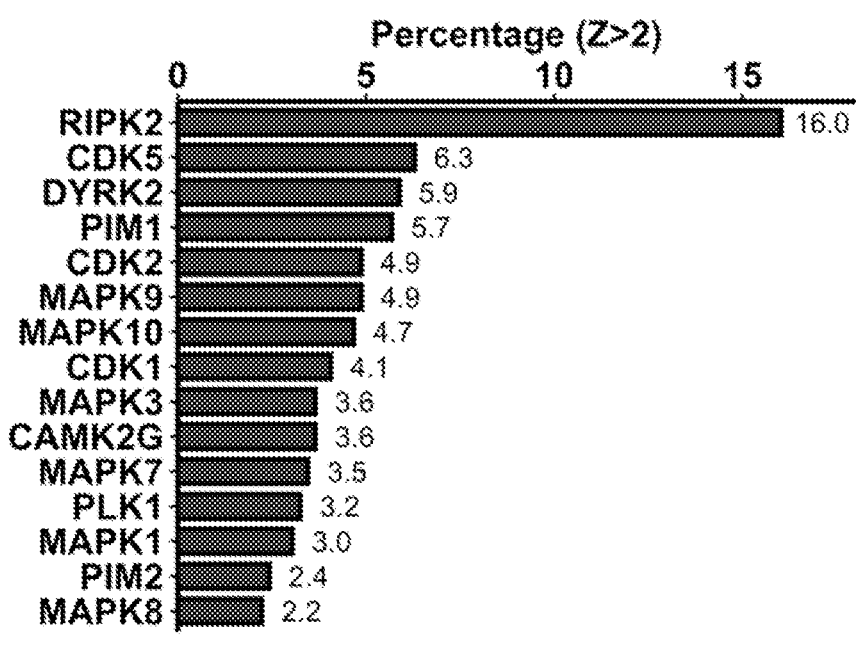

FIG. 29 (panels A-B) shows that the Genetic Alteration of RIPK2 is More Frequent Than That of Any Known Direct c-Myc-Ser62 Kinases in PC Tissue Specimens. (A) Bar plot of the percentages of mCRPC tumors with gene amplification/gain (n=655 in total). Numbers in bars indicate the percentages. (B) Bar plot of the frequency of gene overexpression (Z>2 relative to diploid samples) in the TCGA PanCancer Atlas primary PC cohort (n=493). Numbers to the right of bars indicate the percentages.

Figure 30:
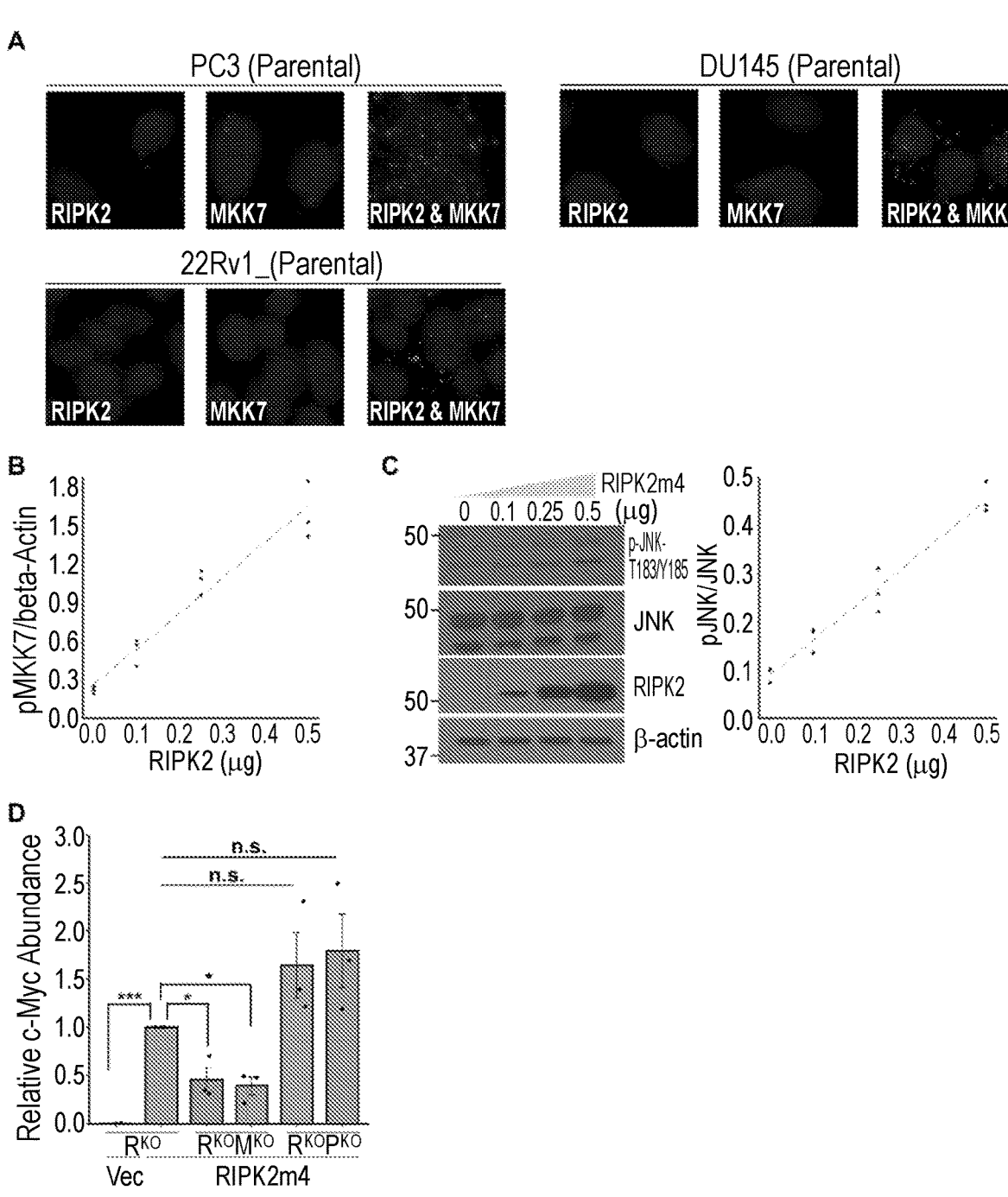

FIG. 30 (panels A-C) shows that RIPK2 Binds to and Activates MKK7, a Major Mediator of RIPK2 Regulation of c-Myc. (A) Representative PLA images of endogenous RIPK2 and MKK7 proteins in parental PC cells. (B) Scatter plot of the pMKK7-S271 levels in RIPK2-KO HEK293T cells transiently transfected with different doses of the RIPK2m4 plasmid (n=3). (C) Representative immunoblots (left) and scatter plot (right) of the pJNK-T183/Y185 levels in RIPK2-KO HEK293T cells transiently transfected with different doses of the RIPK2m4 plasmid (n=3). (D) Bar plot of the relative c-Myc protein abundance in HEK293T cells under the indicated conditions. Unpaired two-tailed Student's t-test (*p<0.05, ***p<0.001). Data are mean±SEM (n=3).

Figure 31:
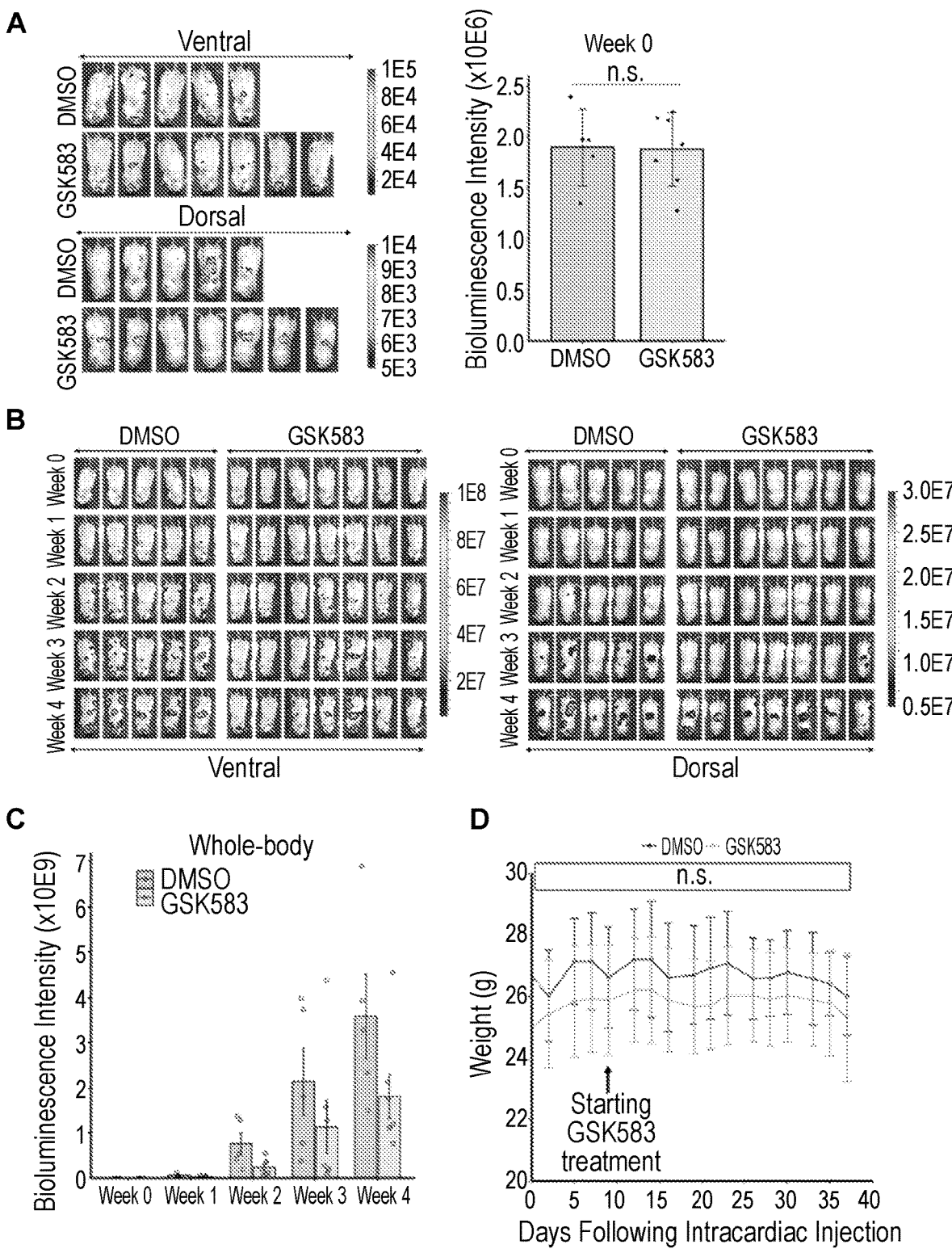

FIG. 31 (panels A-D) shows that GSK583 Inhibits PC Metastasis In Vivo. (A) BLI images (left) and bar plot of the total BLI intensities (right) of mice that were randomized for GSK583 treatment on day 9 after the intracardiac injection of luciferase-tagged control 22Rv1 cells (i.e., week 0 for drug treatment). Mann-Whitney U test (n.s.: not significant). Data are Mean±SEM (n=5 for DMSO control and 7 for GSK583). (B) BLI images of GSK583-treated mice over four weeks. (C) Bar plot of the total BLI intensities of GSK583-treated mice at different weeks. Data are Mean±SEM. (D) Changes of mouse weights following the intracardiac injection of control 22Rv1 cells. Mann-Whitney U test (n.s.: not significant). Data are Mean±SD.

Figure 32:
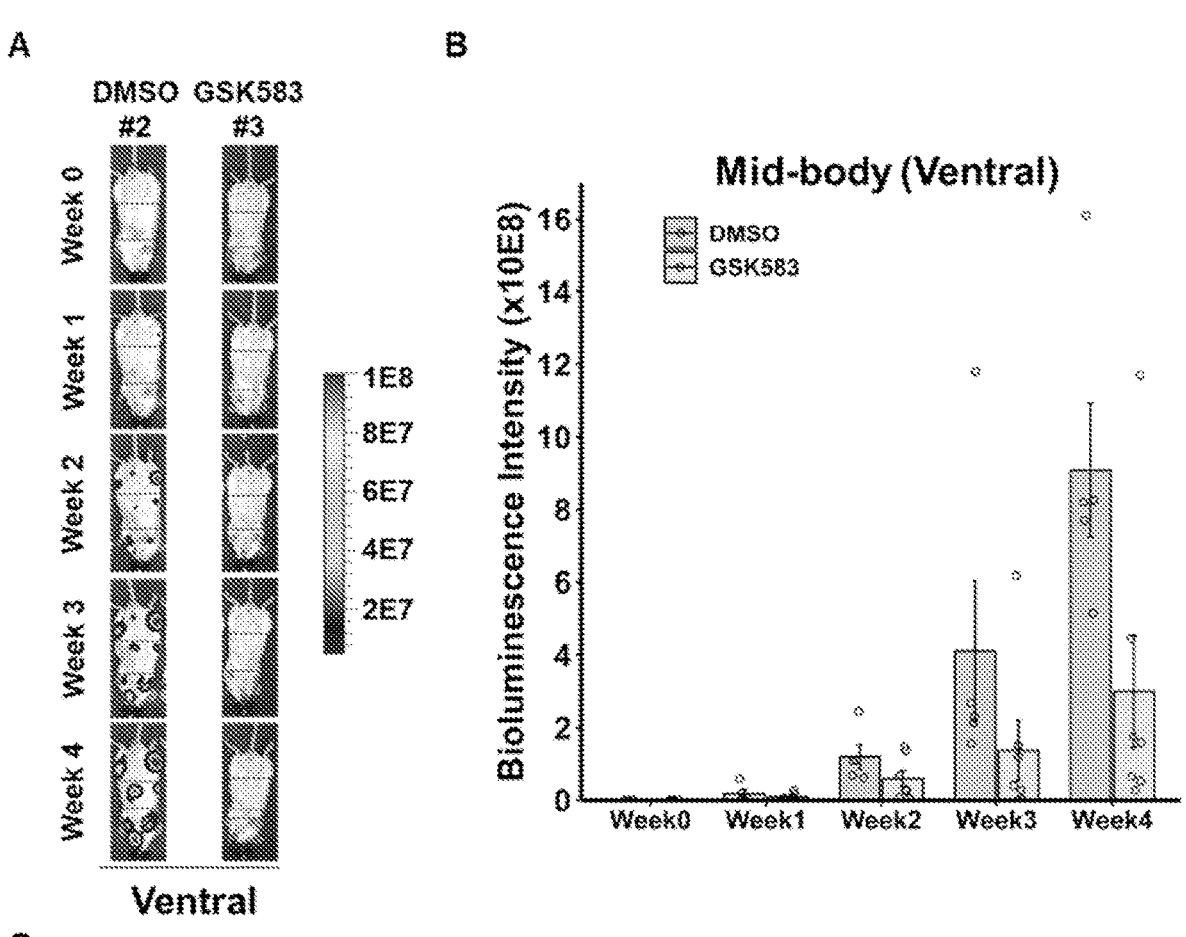
Figure 32:
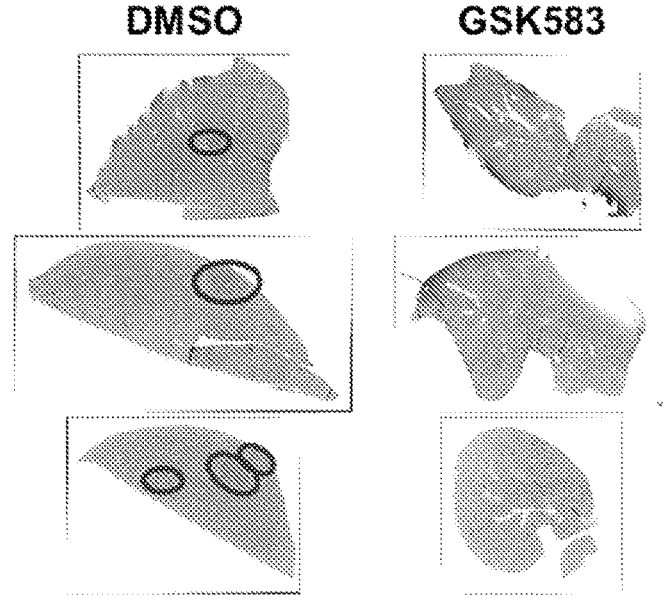

FIG. 32 (panels A-C) shows that GSK583 Inhibits PC Liver Metastasis In Vivo. (A) Representative BLI images of the mid-body sections (in red boxes) of mice at different weeks. Mice were intracardially injected with luciferase-tagged control 22Rv1 cells and monitored by BLI once a week. (B) Bar plot of the ventral side BLI intensities of the mid-body sections of metastasis-bearing mice. Data are Mean±SEM (n=5 for DMSO and 7 for GSK583). (C) Representative H&E-stained images of livers from control and GSK583-treated mice. Liver metastases are shown in red ovals.

Figure 33:
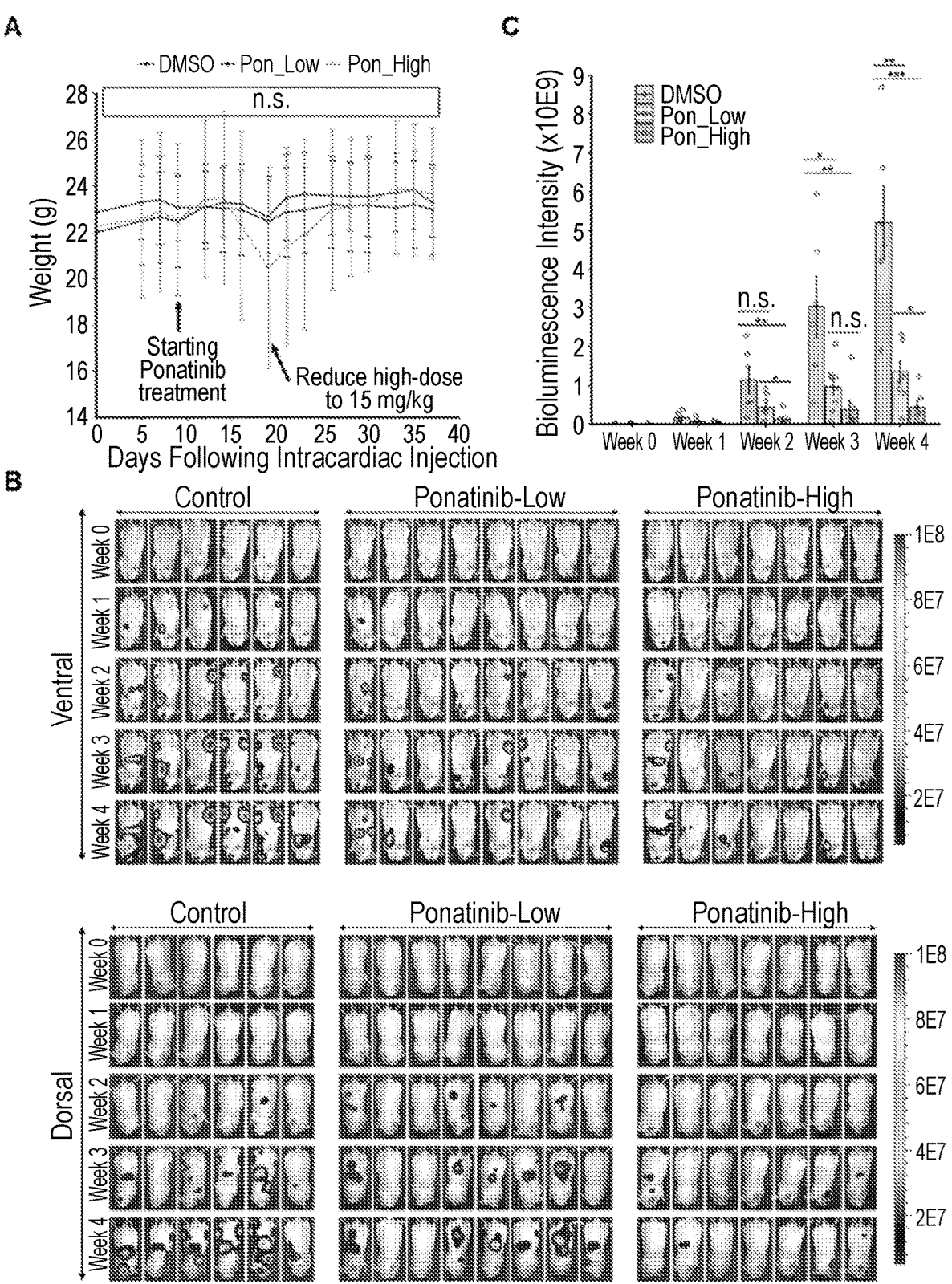

FIG. 33 (panels A-C) shows that Ponatinib Inhibits PC Metastasis in a Dose-dependent Fashion. (A) Line plot of mouse weights after the intracardiac injection of luciferase-tagged 22Rv1 cells. Mann-Whitney U test (n.s.: not significant). Data are Mean±SD. (B) BLI images of Ponatinib-treated mice over four weeks, from the ventral (upper) and dorsal (lower) sides. (C) Bar plot of the total BLI intensities of GSK583-treated mice at different weeks. Mann-Whitney U test (n.s.: not significant, *p<0.05, p<0.01, *p<0.001). Data are Mean±SEM.

DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein the term "about" when used in connection with a referenced numeric indication means the referenced numeric indication plus or minus up to 5% of that referenced numeric indication, unless otherwise specifically provided for herein. For example, the language "about 50%" covers the range of 45% to 55%. In various embodiments, the term "about" when used in connection with a referenced numeric indication can mean the referenced numeric indication plus or minus up to 4%, 3%, 2%, 1%, 0.5%, or 0.25% of that referenced numeric indication, if specifically provided for in the claims.

"Copy number gain" as used herein refers to a low-level copy number increase. In normal cells, the copy number of a gene is generally 2. In cells such as cancer cells, if the copy number is 3-5, it is generally referred to a copy number gain.

"Copy number co-gain" as used herein refers to two or more genes having a copy number gain. For instance, for a specific cancer cell line or tumor specimen, if both RIPK2 and MYC have copy numbers of 3-5, then we refer to the sample as having a RIPK2/MYC co-gain.

"Copy number amplification" as used herein refers to a copy number of more than 5.

"Copy number co-amplification" as used herein refers to two or more genes having a copy amplification. For instance, for a specific cancer cell line or tumor specimen, if both RIPK2 and MYC have copy numbers of greater than 5, then we refer to the sample has having a RIPK2/MYC co-amplification.

Through a multi-omics approach, this invention identified RIPK2 as a novel drug target in lethal prostate cancer and showed that pharmacological inhibition of RIPK2 suppresses prostate cancer metastasis in vitro and in intact animals. This invention provides an innovative drug target RIPK2 and a companion biomarker for pre-selecting patients for precision treatment. Notably, RIPK2 can be inhibited by an FDA approved drug Ponatinib and a drug (GSK2983559) in phase I clinical trial for inflammatory bowel disease. In addition, a novel class of drugs called PROTACs (proteolysis targeting chimeras) are under active development to degrade RIPK2 in cells, and thus can be used.

Metastasis is the major culprit behind cancer morbidity and mortality. When cancer cells metastasize to distant organs and grow into overt metastases, even if they initially respond to therapies, they almost invariably develop therapeutic resistance. Thus, preventing or delaying metastasis has increasingly been appreciated as an effective strategy to improve the quality of life and prolong the survival time of cancer patients.

Described herein, via integrating multi-omics and functional analyses, we discovered and established RIPK2 as a clinically actionable target for inhibiting PC metastasis. Phenotypically, both genetic and pharmacological inhibition of RIPK2 suppressed PC cell invasion and colony formation in vitro and metastasis in vivo. Mechanistically, RIPK2 phosphorylates, stabilizes, and activates c-Myc, largely by activating the MKK7/c-Myc and MKK7/JNK/c-Myc phosphorylation cascades. Of note, phosphorylation cascade is a highly effective strategy for signal amplification, which may explain why RIPK2 and MYC activity scores are strongly correlated in PC and many other cancer types. We believe that these findings described herein represent the first establishment of the functional relationship between three well-studied proteins—the proinflammatory kinase RIPK2, the MAPK kinase MKK7, and the oncoprotein c-Myc. Moreover, these mechanistic findings are clinically relevant because 1) RIPK2 and MYC are frequently co-amplified/gained in lethal PC and several other cancer types and 2) RIPK2 and MYC activity scores are strongly correlated in clinical tissue specimens of 32 cancer types. Of great importance is that Ponatinib is known to be well tolerated and appears to be well suited for such a metastasis-inhibition strategy. Conversely, directly targeting c-Myc in human patients remains elusive. So far, at least 14 kinases have been identified as direct c-Myc-Ser62 kinases, and some of them have been or are being pursued as therapeutic targets for cancer treatment. In comparison, RIPK2 is much more frequently amplified/gained and overexpressed than any of these direct c-Myc-Ser62 kinases in PC tumors, suggesting that targeting RIPK2 may potentially benefit a much larger population of PC patients in comparison to any direct c-Myc-Ser62 kinase.

Although RIPK2 has been studied for over two decades, its direct substrate proteins remain poorly defined. Our interactome and phosphoproteomics datasets provide a rich source for discovering direct RIPK2 substrates. In particular, our comprehensive interactome analysis identified a large number (>200) of RIPK2-interacting proteins, of which the vast majority are novel. Many RIPK2-associated proteins in the canonical RIPK2 pathway, such as NOD1/2, TAB2/3, and IKK, were not identified by our interactome analysis. This is probably because our in vitro cell culture system does not contain bacteria-released ligands (e.g., muramyl dipeptide), which are required for the activation of the canonical pathway. In addition, according to the Cancer Cell Line Encyclopedia (CCLE) database, the expression levels of NOD1 and NOD2 in PC cell lines are generally very low. Thus, the canonical NOD/RIPK2 pathway is probably not important in PC development and progression. In this study, we discovered that RIPK2 associates with six protein kinases: MKK7 (MAP2K7), DNA-PKcs (PRKDC), RSK2 (RPS6KA3), MST4 (STK26), MEK2 (MAP2K2), and CSK (CSK). We confirmed that RIPK2 binds to MKK7 and DNA-PKcs and that RIPK2 directly activates MKK7. Previous studies showed that DNA-PKcs is highly activated in metastatic PC and its inhibition suppresses PC metastasis in vivo, RSK2-targeting suppresses lung cancer metastasis, MST4 promotes gastric cancer metastasis, and MEK2 promotes colorectal cancer metastasis. Delineating the hierarchy between these kinases and RIPK2 will provide further insights into RIPK2 functions in cancer metastasis.

In summary, we identified RIPK2 as a novel, actionable drug target for inhibiting PC metastasis, operating largely via the noncanonical RIPK2/MKK7(/JNK)/c-Myc signaling axis discovered in this study. Targeting RIPK2 by genetic knockout or small-molecule inhibitors effectively blocks the pathway, leading to the destabilization of the c-Myc oncoprotein and the inhibition of PC metastasis (FIG. 22N). RIPK2 binds to MKK7 and activates the MKK7(/JNK)/c-Myc phosphorylation cascades, thereby stabilizing the c-Myc oncoprotein and enhancing c-Myc activity, which is required for PC metastasis. The non-canonical RIPK2/MKK7/c-Myc signaling pathways can be blocked by genetic or pharmacological inhibition of RIPK2, resulting in the proteasomal degradation of c-Myc and the inhibition of c-Myc activity and PC metastasis. Of clinical relevance, RIPK2 and MYC are frequently co-amplified/gained in PC and several other cancer types, and their activity scores are strongly correlated across many cancers. Besides PC, RIPK2 is frequently genetically altered in several other cancers, its overexpression is associated with shorter overall survival in nine cancer types, and its activity scores are highly correlated with MYC activity scores across 32 cancer types. Thus, clinical trials targeting RIPK2—either alone or in combination with established or emerging therapies—are warranted for personalized anti-metastatic therapy towards substantially improving clinical outcomes.

Accordingly, various embodiments of the present invention are based, in part, on these finding.

Treatments

Various embodiments of the present invention provide for a method of treating cancer in a subject in need thereof, comprising: administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments of the present invention provide for a method of inhibiting metastasis of a cancer in a subject in need thereof, comprising: administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments of the present invention provide for a method of inhibiting the growth of cancer in a subject in need thereof, comprising: administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

In various embodiments, the RIPK2 inhibitor is ponatinib, and the cancer is not chronic myeloid leukemia (CML), or Philadelphia chromosome-positive (PH+) acute lymphoblastic leukemia (ALL). In various embodiments, the RIPK2 inhibitor is GSK2983559 and the subject does not have inflammatory bowel disease. In various embodiments, the RIPK2 inhibitor is ponatinib, GSK-583, ODS-101, or a combination thereof. In various embodiments, the RIPK2 inhibitor is GSK2983559, regorafenib, sorafenib, or a combination thereof.

In various embodiments, about 30, 40, 45, 50, 55, 60, 65, 70, 75, 80, 85 or 90 mg of the RIPK2 inhibitor is administered.

In various embodiments, the RIPK2 inhibitor is ponatinib. In various embodiments, about 30 mg of ponatinib is administered. In various embodiments, about 5, 10, 15, 20, 25, 30, 40, 45, 50, 55, 60, 65, 70, 75, 80, 85 or 90 mg of ponatinib is administered. In various embodiments, about 0.05, 0.1, 0.15, 0.2, 0.25, 0.3, 0.35, 0.4, 0.45, 0.5, 0.55, 0.6, 0.065, 0.7, 0.75, 0.8, 0.85, 0.9, 0.95, or 1.0 mg/kg of ponatinib is administered.

In various embodiments, the cancer is prostate cancer. In various embodiments, the cancer is advance prostate cancer. In various embodiments, the cancer is breast cancer, liver cancer, bladder cancer, or melanoma.

In various embodiments, the cancer is uveal melanoma, liver hepatocellular carcinoma, colorectal adenocarcinoma, breast invasive carcinoma, prostate adenocarcinoma, lung adenocarcinoma, sarcoma, head and neck squamous cell carcinoma, diffuse large B-Cell lymphoma, bladder urothelial carcinoma, cholangiocarcinoma, kidney chromophobe, lung squamous cell carcinoma, esophageal adenocarcinoma, stomach adenocarcinoma, ovarian serous cystadenocarcinoma, cervical squamous cell carcinoma, skin cutaneous melanoma, testicular germ cell tumor, mesothelioma, kidney renal clear cell carcinoma, uterine carcinosarcoma, acute myeloid leukemia, uterine corpus endometrial carcinoma, kidney renal papillary cell carcinoma, glioblastoma multiforme, brain lower grade glioma, adrenocortical carcinoma, thymoma, thyroid carcinoma, pheochromocytoma and paraganglioma, or pancreatic adenocarcinoma.

In various embodiments, the subject has been determined to have an increased expression of RIPK2 in cancer cells, as compared to non-cancerous cells. In various embodiments, the subject has been determined to have a RIPK2 copy number gain in cancer cells as compared to non-cancerous cells. In various embodiments, the subject has been determined to have a MYC copy number gain in cancer cells as compared to non-cancerous cells. In various embodiments, the subject has been determined to have a RIPK2/MYC copy number co-gain in cancer cells as compared to non-cancerous cells. In various embodiments, the subject has been determined to have a RIPK2 copy number amplification, a MYC copy number amplification, or a RIPK2/MYC copy number co-amplification in cancer cells as compared to non-cancerous cells.

In various embodiments, the cancer is not chronic myeloid leukemia (CML), or Philadelphia chromosome-positive (PH+) acute lymphoblastic leukemia (ALL). In various embodiments, the subject does not have inflammatory bowel disease.

Detection and Diagnosis

Various embodiments of the present invention provide for a method of selecting a subject for treatment with a receptor-interacting protein kinase 2 (RIPK2) inhibitor, comprising: obtaining a biological sample from the subject; detecting, in the biological sample, an increased expression in RIPK2, MYC or both as compared to noncancerous cells; selecting the RIPK2 inhibitor for treating the subject, wherein if the RIPK2 inhibitor is ponatinib, the subject does not have chronic myeloid leukemia (CML), or Philadelphia chromosome-positive (PH+) acute lymphoblastic leukemia (ALL).

Various embodiments of the present invention provide for a method of selecting a subject for treatment with a receptor-interacting protein kinase 2 (RIPK2) inhibitor, comprising: obtaining a biological sample from the subject; detecting, in the biological sample, a copy number gain in RIPK2, MYC or both, as compared to noncancerous cells; selecting the RIPK2 inhibitor for treating the subject, wherein if the RIPK2 inhibitor is ponatinib, the subject does not have chronic myeloid leukemia (CML), or Philadelphia chromosome-positive (PH+) acute lymphoblastic leukemia (ALL).

Various embodiments of the present invention provide for a method of selecting a subject for treatment with a receptor-interacting protein kinase 2 (RIPK2) inhibitor, comprising: obtaining a biological sample from the subject; detecting, in the biological sample, a copy number amplification in RIPK2, MYC or both, as compared to noncancerous cells; selecting the RIPK2 inhibitor for treating the subject, wherein if the RIPK2 inhibitor is ponatinib, the subject does not have chronic myeloid leukemia (CML), or Philadelphia chromosome-positive (PH+) acute lymphoblastic leukemia (ALL).

In various embodiments, the method further comprises administering the RIPK2 inhibitor to the subject.

In various embodiments, the RIPK2 inhibitor is ponatinib, GSK-583, ODS-101, or a combination thereof. In various embodiments, the RIPK2 inhibitor is GSK2983559, regorafenib, sorafenib, or a combination thereof.

In various embodiments, about 30, 40, 45, 50, 55, 60, 65, 70, 75, 80, 85 or 90 mg of the RIPK2 inhibitor is administered.

In various embodiments, the RIPK2 inhibitor is ponatinib. In various embodiments, about 30 mg of ponatinib is administered. In various embodiments, about 5, 10, 15, 20, 25, 30, 40, 45, 50, 55, 60, 65, 70, 75, 80, 85 or 90 mg of ponatinib is administered. In various embodiments, about 0.05, 0.1, 0.15, 0.2, 0.25, 0.3, 0.35, 0.4, 0.45, 0.5, 0.55, 0.6, 0.065, 0.7, 0.75, 0.8, 0.85, 0.9, 0.95, or 1.0 mg/kg of ponatinib is administered.

In various embodiments, the subject has cancer. In various embodiments, the cancer is prostate cancer. In various embodiments, the cancer is advanced prostate cancer. In various embodiments, the cancer is breast cancer, liver cancer, bladder, cancer, or melanoma.

In various embodiments, the cancer is uveal melanoma, liver hepatocellular carcinoma, colorectal adenocarcinoma, breast invasive carcinoma, prostate adenocarcinoma, lung adenocarcinoma, sarcoma, head and neck squamous cell carcinoma, diffuse large B-Cell lymphoma, bladder urothelial carcinoma, cholangiocarcinoma, kidney chromophobe, lung squamous cell carcinoma, esophageal adenocarcinoma, stomach adenocarcinoma, ovarian serous cystadenocarcinoma, cervical squamous cell carcinoma, skin cutaneous melanoma, testicular germ cell tumor, mesothelioma, kidney renal clear cell carcinoma, uterine carcinosarcoma, acute myeloid leukemia, uterine corpus endometrial carcinoma, kidney renal papillary cell carcinoma, glioblastoma multiforme, brain lower grade glioma, adrenocortical carcinoma, thymoma, thyroid carcinoma, pheochromocytoma and paraganglioma, or pancreatic adenocarcinoma.

In various embodiments, the biological sample comprises cancer cells.

In various embodiments, the RIPK2 inhibitor is ponatinib, and the cancer is not chronic myeloid leukemia (CML), or Philadelphia chromosome-positive (PH+) acute lymphoblastic leukemia (ALL). In various embodiments, the RIPK2 inhibitor is GSK2983559 and the subject does not have inflammatory bowel disease.

In various embodiments, the cancer is not chronic myeloid leukemia (CML), or Philadelphia chromosome-positive (PH+) acute lymphoblastic leukemia (ALL). In various embodiments, the subject does not have inflammatory bowel disease.

Detection and/or Administrations

Various embodiments provide for a method for treating cancer in a subject in need thereof, comprising: detecting, in the biological sample, an increased expression in RIPK2, MYC or both as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of inhibiting the growth of cancer in a subject in need thereof, comprising: detecting, in the biological sample, an increased expression in RIPK2, MYC or both as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of inhibiting metastasis of a cancer in a subject in need thereof, comprising: detecting, in the biological sample, an increased expression in RIPK2, MYC or both as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method for treating cancer in a subject in need thereof, comprising: detecting, in the biological sample, a copy number gain in RIPK2, MYC or both, as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of inhibiting the growth of cancer in a subject in need thereof, comprising: detecting, in the biological sample, a copy number gain in RIPK2, MYC or both, as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of inhibiting metastasis of a cancer in a subject in need thereof, comprising: detecting, in the biological sample, a copy number gain in RIPK2, MYC or both, as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of treating cancer in a subject in need thereof, comprising: obtaining or requesting the results of an analysis for an increased expression in RIPK2, MYC or both, or a copy number gain in RIPK2, MYC or both, or a copy number amplification in RIPK2, MYC or both, as compared to noncancerous cells, in a biological sample obtained from the subject, as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of inhibiting the growth of cancer, comprising: obtaining or requesting the results of an analysis for an increased expression in RIPK2, MYC or both, or a copy number gain in RIPK2, MYC or both, or a copy number amplification in RIPK2, MYC or both, as compared to noncancerous cells, in a biological sample obtained from the subject, as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of inhibiting metastasis in a subject in need thereof, comprising: obtaining or requesting the results of an analysis for an increased expression in RIPK2, MYC or both, or a copy number gain in RIPK2, MYC or both, or a copy number amplification in RIPK2, MYC or both, as compared to noncancerous cells, in a biological sample obtained from the subject, as compared to noncancerous cells; and administering a receptor-interacting protein kinase 2 (RIPK2) inhibitor to the subject, wherein if the RIPK2 inhibitor is ponatinib, the cancer is not chronic myeloid leukemia (CML), or Philadelphia chromosome-positive (PH+) acute lymphoblastic leukemia (ALL).

Various embodiments of the present invention provide for a method of treating cancer in a subject in need thereof, comprising: administering a receptor-interacting protein kinase 2 (RIPK2) inhibitor to the subject, wherein the subject has been determined to have an increased expression in RIPK2, MYC or both, or a copy number gain in RIPK2, MYC or both, or a copy number amplification in RIPK2, MYC or both, as compared to noncancerous cells, in a biological sample obtained from the subject, as compared to noncancerous cells, and wherein if the RIPK2 inhibitor is ponatinib, the cancer is not chronic myeloid leukemia (CML), or Philadelphia chromosome-positive (PH+) acute lymphoblastic leukemia (ALL).

Various embodiments provide for a method of detecting an increased expression in RIPK2, MYC or both, or a copy number gain in RIPK2, MYC or both, or a copy number amplification in RIPK2, MYC or both, as compared to noncancerous cells, in a biological sample obtained from a subject, as compared to noncancerous cells in a subject, comprising: assaying a biological sample obtained from the subject, wherein the subject desires a determination regarding cancer; and detecting an increased expression in RIPK2, MYC or both, or a copy number gain in RIPK2, MYC or both, or a copy number amplification in RIPK2, MYC or both, as compared to noncancerous cells, in a biological sample obtained from the subject, as compared to noncancerous cells.

Various embodiments of the present invention provide for a method of detecting an increased expression in RIPK2, MYC or both, or a copy number gain in RIPK2, MYC or both, or a copy number amplification in RIPK2, MYC or both, as compared to noncancerous cells, in a biological sample obtained from a subject, comprising: assaying a biological sample obtained from the subject, wherein the subject exhibits a symptom of cancer; and detecting an increased expression in RIPK2, MYC or both, or a copy number gain in RIPK2, MYC or both, or a copy number amplification in RIPK2, MYC or both, as compared to noncancerous cells, in a biological sample obtained from a subject.

In various embodiments, the RIPK2 inhibitor is ponatinib, GSK-583, ODS-101, or a combination thereof. In various embodiments, the RIPK2 inhibitor is GSK2983559, regorafenib, sorafenib, or a combination thereof.

In various embodiments, about 30, 40, 45, 50, 55, 60, 65, 70, 75, 80, 85 or 90 mg of the RIPK2 inhibitor is administered.

In various embodiments, the RIPK2 inhibitor is ponatinib. In various embodiments, about 30 mg of ponatinib is administered. In various embodiments, about 5, 10, 15, 20, 25, 30, 40, 45, 50, 55, 60, 65, 70, 75, 80, 85 or 90 mg of ponatinib is administered. In various embodiments, about 0.05, 0.1, 0.15, 0.2, 0.25, 0.3, 0.35, 0.4, 0.45, 0.5, 0.55, 0.6, 0.065, 0.7, 0.75, 0.8, 0.85, 0.9, 0.95, or 1.0 mg/kg of ponatinib is administered.

In various embodiments, the subject has cancer. In various embodiments, the cancer is prostate cancer. In various embodiments, the cancer is advanced prostate cancer. In various embodiments, the cancer is breast cancer, liver cancer, bladder, cancer, or melanoma.

In various embodiments, the cancer is uveal melanoma, liver hepatocellular carcinoma, colorectal adenocarcinoma, breast invasive carcinoma, prostate adenocarcinoma, lung adenocarcinoma, sarcoma, head and neck squamous cell carcinoma, diffuse large B-Cell lymphoma, bladder urothelial carcinoma, cholangiocarcinoma, kidney chromophobe, lung squamous cell carcinoma, esophageal adenocarcinoma, stomach adenocarcinoma, ovarian serous cystadenocarcinoma, cervical squamous cell carcinoma, skin cutaneous melanoma, testicular germ cell tumor, mesothelioma, kidney renal clear cell carcinoma, uterine carcinosarcoma, acute myeloid leukemia, uterine corpus endometrial carcinoma, kidney renal papillary cell carcinoma, glioblastoma multiforme, brain lower grade glioma, adrenocortical carcinoma, thymoma, thyroid carcinoma, pheochromocytoma and paraganglioma, or pancreatic adenocarcinoma.

In various embodiments, the biological sample comprises cancer cells.

In various embodiments, the RIPK2 inhibitor is ponatinib, and the cancer is not chronic myeloid leukemia (CML), or Philadelphia chromosome-positive (PH+) acute lympho-blastic leukemia (ALL). In various embodiments, the RIPK2 inhibitor is GSK2983559 and the subject does not have inflammatory bowel disease.

In various embodiments, the cancer is not chronic myeloid leukemia (CML), or Philadelphia chromosome-positive (PH+) acute lymphoblastic leukemia (ALL). In various embodiments, the subject does not have inflammatory bowel disease.

In various embodiments, the present invention provides pharmaceutical compositions including a pharmaceutically acceptable excipient along with a therapeutically effective amount of the RIPK2 inhibitor. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prod-rugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a rea-sonable benefit/risk ratio, and effective for their intended use of the compounds of the invention. The term "salts" refers to the relatively non-toxic, inorganic and organic acid addi-tion salts of compounds of the present invention. These salts can be prepared in situ during the final isolation and puri-fication of the compounds or by separately reacting the purified compound in its free base form with a suitable organic or inorganic acid and isolating the salt thus formed. These may include cations based on the alkali and alkaline earth metals such as sodium, lithium, potassium, calcium, magnesium and the like, as well as nontoxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like.

The term "pharmaceutically acceptable esters" refers to the relatively nontoxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active one or more peptides as disclosed herein or a mutant, variant, analog or derivative thereof. A thorough discussion is pro-vided in T. Higachi and V. Stella, "Pro-drugs as Novel Delivery Systems," Vol. 14 of the A. C. S. Symposium Series, and in Bioreversible Carriers in: Drug Design, ed. Edward B. Roche, American Pharmaceutical Association and Pergamon Press, 1987, both of which are hereby incor-porated by reference. As used herein, a prodrug is a com-pound that, upon in vivo administration, is metabolized or otherwise converted to the biologically, pharmaceutically or therapeutically active form of the compound. A prodrug of the one or more peptides as disclosed herein or a mutant, variant, analog or derivative thereof can be designed to alter the metabolic stability or the transport characteristics of one or more peptides as disclosed herein or a mutant, variant, analog or derivative thereof, to mask side effects or toxicity, to improve the flavor of a compound or to alter other characteristics or properties of a compound. By virtue of knowledge of pharmacodynamic processes and drug metabolism in vivo, once a pharmaceutically active form of the one or more peptides as disclosed herein or a mutant, variant, analog or derivative thereof, those of skill in the pharmaceutical art generally can design prodrugs of the compound (see, e.g., Nogrady (1985) Medicinal Chemistry A Biochemical Approach, Oxford University Press, N. Y., pages 388-392). Conventional procedures for the selection and preparation of suitable prodrugs are described, for example, in "Design of Prodrugs," ed. H. Bundgaard, Else-vier, 1985. Suitable examples of prodrugs include methyl, ethyl and glycerol esters of the corresponding acid.

In various embodiments, the pharmaceutical composi-tions according to the invention may be formulated for delivery via any route of administration. "Route of admin-istration" may refer to any administration pathway known in the art, including but not limited to aerosol, nasal, oral, transmucosal, transdermal or parenteral. "Transdermal" administration may be accomplished using a topical cream or ointment or by means of a transdermal patch. "Parenteral" refers to a route of administration that is generally associated with injection, including intraorbital, infusion, intraarterial, intracapsular, intracardiac, intradermal, intramuscular, intra-peritoneal, intrapulmonary, intraspinal, intrasternal, intrath-ecal, intrauterine, intravenous, subarachnoid, subcapsular, subcutaneous, transmucosal, or transtracheal. Via the par-enteral route, the compositions may be in the form of solutions or suspensions for infusion or for injection, or as lyophilized powders. Via the enteral route, the pharmaceu-tical compositions can be in the form of tablets, gel capsules, sugar-coated tablets, syrups, suspensions, solutions, pow-ders, granules, emulsions, microspheres or nanospheres or lipid vesicles or polymer vesicles allowing controlled release. Via the parenteral route, the compositions may be in the form of solutions or suspensions for infusion or for injection. Via the topical route, the pharmaceutical compo-sitions based on compounds according to the invention may be formulated for treating the skin and mucous membranes and are in the form of ointments, creams, milks, salves, powders, impregnated pads, solutions, gels, sprays, lotions or suspensions. They can also be in the form of microspheres or nanospheres or lipid vesicles or polymer vesicles or polymer patches and hydrogels allowing controlled release. These topical-route compositions can be either in anhydrous form or in aqueous form depending on the clinical indica-tion. Via the ocular route, they may be in the form of eye drops.

The pharmaceutical compositions according to the inven-tion can also contain any pharmaceutically acceptable car-rier. "Pharmaceutically acceptable carrier" as used herein refers to a pharmaceutically acceptable material, composi-tion, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

In some embodiments of the invention, the therapeutically effective amounts of the RIPK2 inhibitor can be in the range of about 1-5 µg/day, 5-10 µg/day, 10-15 µg/day, 15-20 µg/day, 10-20 µg/day, 20-30 µg/day, 30-40 µg/day, 40-50 µg/day, 50-60 µg/day, 60-70 µg/day, 70-80 µg/day, 80-90 µg/day, 90-100 µg/day, 100-110 µg/day, 110-120 µg/day, 120-130 µg/day, 130-140 µg/day, 140-150 µg/day, 150-160 µg/day, 160-170 µg/day, 170-180 µg/day, 180-190 µg/day, 190-200 µg/day, 200-210 µg/day, 210-220 µg/day, 220-230 µg/day, 230-240 µg/day, 240-250 µg/day, 250-260 µg/day, 260-270 µg/day, 270-280 µg/day, 280-290 µg/day or 290-300 µg/day.

In some embodiments of the invention, the therapeutically effective amounts of the RIPK2 inhibitor can be in the range of about 10-50 µg/day, 50-100 µg/day, 100-150 µg/day, 150-200 µg/day, 100-200 µg/day, 200-300 µg/day, 300-400 µg/day, 400-500 µg/day, 500-600 µg/day, 600-700 µg/day, 700-800 µg/day, 800-900 µg/day, 900-1000 µg/day, 1000-1100 µg/day, 1100-1200 µg/day, 1200-1300 µg/day, 1300-1400 µg/day, 1400-1500 µg/day, 1500-1600 µg/day, 1600-1700 µg/day, 1700-1800 µg/day, 1800-1900 µg/day, 1900-2000 µg/day, 2000-2100 µg/day, 2100-2200 µg/day, 2200-2300 µg/day, 2300-2400 µg/day, 2400-2500 µg/day, 2500-2600 µg/day, 2600-2700 µg/day, 2700-2800 µg/day, 2800-2900 µg/day or 2900-3000 µg/day.

In some embodiments of the invention, the therapeutically effective amounts of one or more RIPK2 inhibitor can be in the range of about 1-10 mg/day, 10-50 mg/day, 50-100 mg/day, 100-150 mg/day, 150-200 mg/day, 100-200 mg/day, 200-300 mg/day, 300-400 mg/day, 400-500 mg/day, 500-600 mg/day, 600-700 mg/day, 700-800 mg/day, 800-900 mg/day, or 900-1000 mg/day.

In various embodiments, the effective amount of RIPK2 inhibitor is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 µg/kg/day, or a combination thereof. In various embodiments, the effective amount of RIPK2 inhibitor is any one or more of about 0.001-0.01, 0.01-0.1, 0.1-0.5, 0.5-5, 5-10, 10-20, 20-50, 50-100, 100-200, 200-300, 300-400, 400-500, 500-600, 600-700, 700-800, 800-900, or 900-1000 mg/kg/day, or a combination thereof. In various embodiments, the effective amount of RIPK2 inhibitor is any one or more of about 0.05, 0.1, 0.15, 0.2, 0.25, 0.3, 0.35, 0.4, 0.45, 0.5, 0.55, 0.6, 0.065, 0.7, 0.75, 0.8, 0.85, 0.9, 0.95, or 1.0 mg/kg/day, or a combination thereof. Here, "µg/kg/day" or "mg/kg/day" refers to µg or mg agent per kg body weight of the subject per day.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Figure 1:
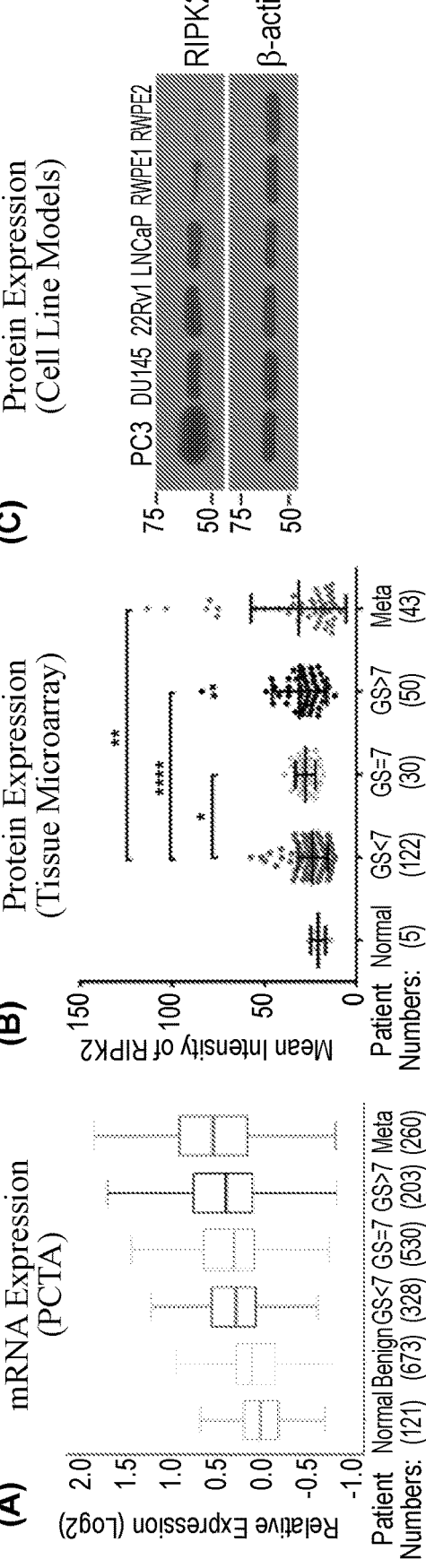
FIG. 1, panels (A)-(C), shows RIPK2 overexpression is positively associated with PCa aggressiveness. (A) The mRNA expression levels of RIPK2 is positively associated with PCa aggressiveness in clinical tissue specimens, according to our Prostate Cancer Transcriptome Atlas (PCTA). (B) The protein expression levels of RIPK2 are positively associated with PCa aggressiveness, according to our immunohistochemistry analysis of PCa tissue microarrays. (C) The protein expression levels of RIPK2 are positively associated with PCa aggressiveness in preclinical PCa cell line models.

RIPK2 is frequently amplified in mCRPC and overexpressed along with PCa progression. To identify novel druggable targets in mCRPC, we overlapped the genes that are frequently amplified in mCRPC with the druggable genome. The top five genes that have FDA-approved drugs (Tclin) or potent small molecule inhibitors (Tchem) are AR (54%), RIPK2 (32%), CA1 (32%), CA13 (32%), and KCNB2 (32%). Among these, RIPK2 is well characterized in inflammation and innate immunity, yet very little is known about its functions in PCa. Our further analysis showed that RIPK2 is rarely (4.2%) amplified in primary PCa. Moreover, RIPK2 mRNA and protein expression levels are positively associated with PCa aggressiveness in clinical tissue specimens and preclinical cell line models (FIG. 1), suggesting that RIPK2 is potentially an mCRPC driver.

Figure 2:
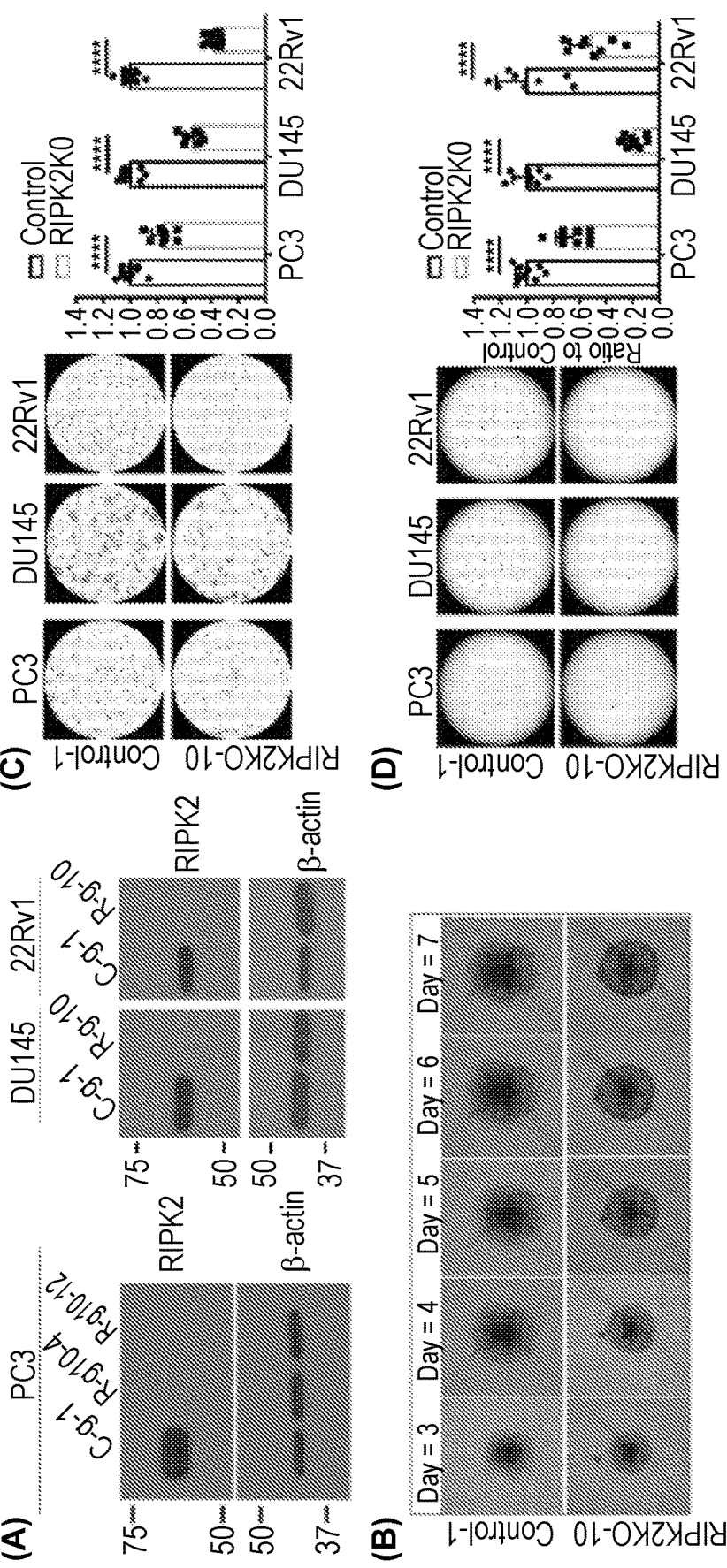
FIG. 2, panels (A)-(D), shows RIPK2 knockout (KO) significantly inhibits PCa cell invasion and colony formation. (A) Immunoblotting analysis confirms CRISPR/Cas9 knockout of RIPK2 in PC3, DU145, and 22Rv1 cell lines. (B) RIPK2-KO in PC3 cells inhibits cell invasion in 3D culture. (C) RIPK2-KO significantly inhibits anchorage-dependent colony formation of PC3, DU145, and 22Rv1 cell lines. (D) RIPK2-KO significantly inhibits anchorage independent colony formation of PC3, DU145, and 22Rv1 cell lines.

RIPK2 knockout (KO) inhibits PCa cell invasion and colony formation. We generated PCa cell lines with stable RIPK2 KO by CRISPR/Cas9. Functional assays suggested that RIPK2-KO significantly suppresses cell invasion as well as anchorage-dependent and -independent colony formations (FIG. 2). Together, these suggest that RIPK2 is functionally important in driving PCa progression.

Figure 3:
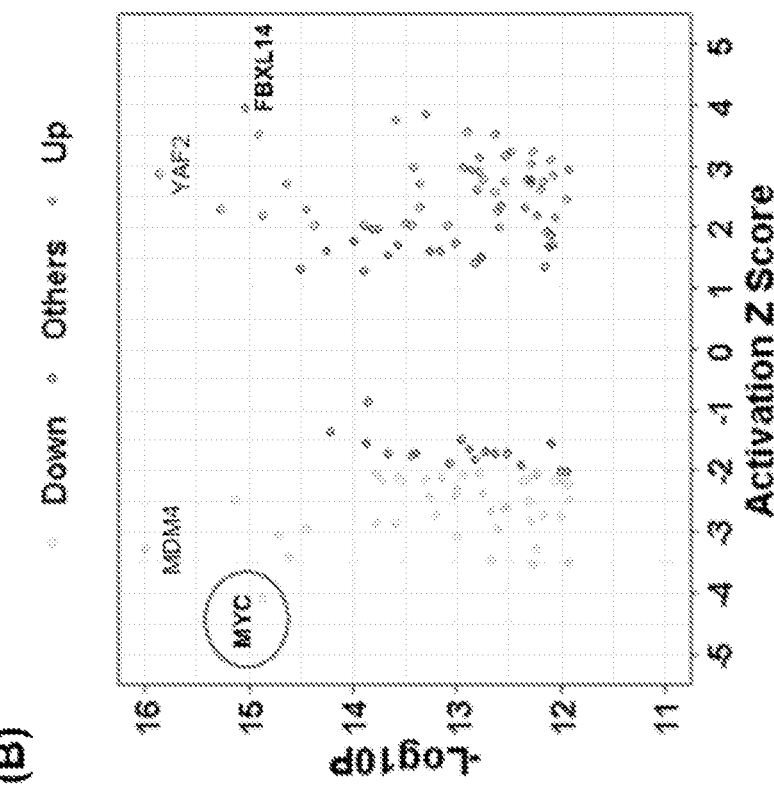
FIG. 3, panels (A)-(B), shows that label-free proteomics identifies c-Myc as a candidate key mediator of RIPK2 signaling in PC3 cells. (A) Heatmap of proteins differentially expressed after RIPK2 knockout in PC3 cells. A statistical analysis of the 4,960 quantified proteins identified 137 significantly downregulated and 260 significantly upregulated proteins. (B) Ingenuity Pathway analysis of the differentially expressed proteins identified c-Myc as the most dramatically inactivated master regulator downstream of RIPK2. The analysis was performed using the Causal Network Analysis algorithm.

Label-free proteomics identified c-Myc as a candidate key mediator of RIPK2 signaling. To identify the key mediators of RIPK2 signaling, we applied label-free proteomics to compare the proteomes of PC3 cells with vs. without RIPK2-KO. Ingenuity Pathway Analysis of the differentially expressed proteins identified c-Myc, a potent oncoprotein, as the most dramatically inactivated master regulator downstream of RIPK2 (FIG. 3).

RIPK2 regulates c-Myc protein abundance, activity, and stability. Our preliminary study suggested that RIPK2-KO dramatically decreased c-Myc protein abundance, activity, and stability in PC3 cells (FIG. 4A-C). It also showed that RIPK2 overexpression (OE) significantly increased c-Myc abundance and c-Myc$^{S62}$ phosphorylation in a dose-dependent fashion (FIG. 4D-E). Notably, pS62-c-Myc is generally considered as the stable form of c-Myc.

Figure 5:
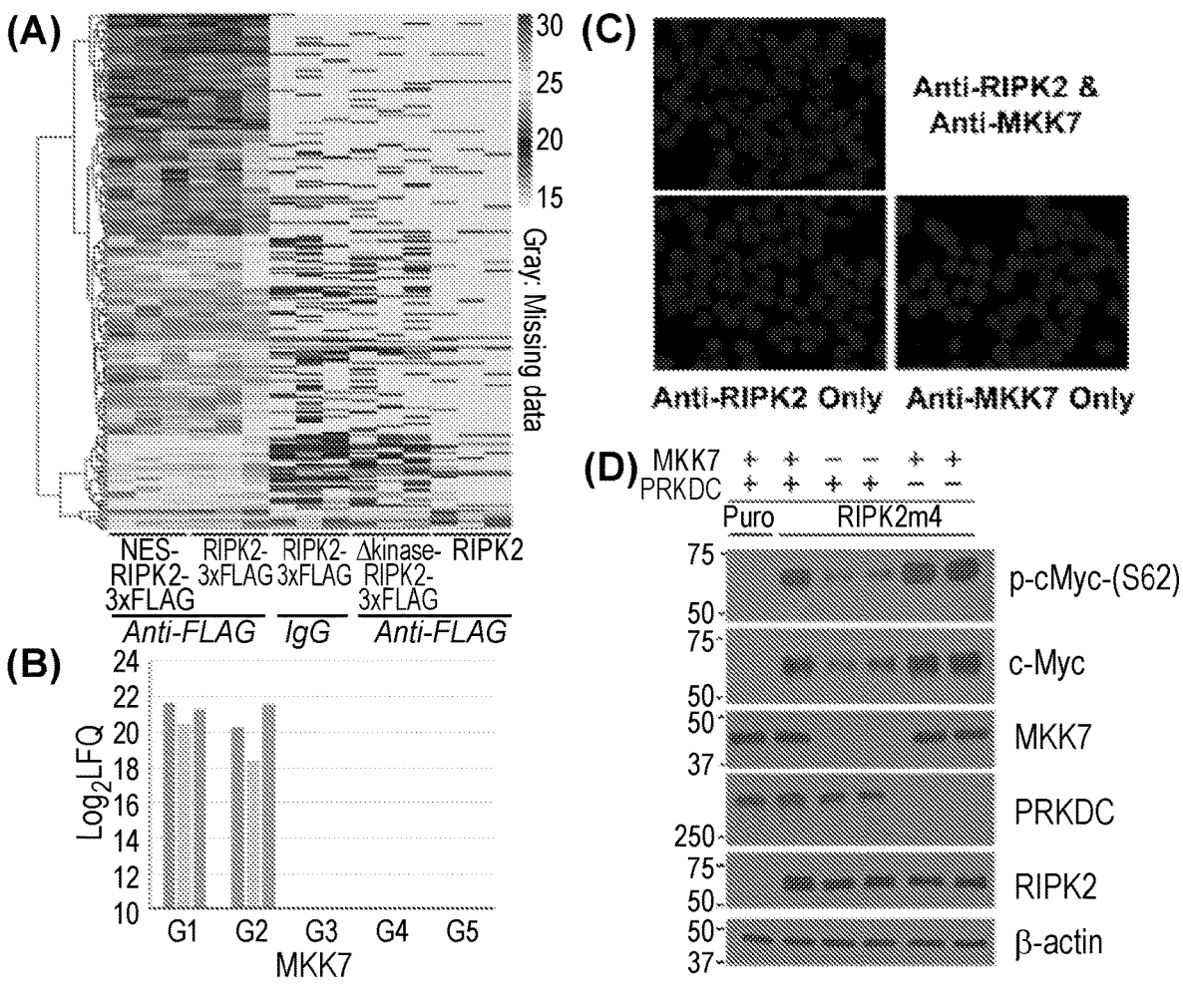
FIG. 5, panels (A)-(D), shows that MKK7 associates with RIPK2 and is essential for RIPK2's stabilization of c-Myc. (A) Heatmap of 226 proteins associated with the kinase domain of RIPK2, which is essential for RIPK2's stabilization of c-Myc (data not shown). (B) Histogram of the log$_2$-transformed label-free quantification (LFQ) intensities. G1 to G5 correspond to the five groups shown in panel A. The three colors represent three different biological replicates. (C) In-situ proximity ligation assay (PLA) validation of the RIPK2-MKK7 interaction. Red dots show the in-situ PLA signals visualizing RIPK2-MKK7 interaction. DAPI (blue) was used to stain nuclei. Anti-RIPK2 alone and anti-MKK7 alone were used as negative controls. (D) MKK7 but not PRKDC is essential for RIPK2's phosphorylation of c-Myc$^{S62}$ and stabilization of c-Myc. MKK7 knockout significantly suppressed RIPK2-induced c-Myc$^{S62}$ phosphorylation and protein stabilization. NES: nuclear export signal; Δkinase: deletion of the kinase domain.

Mitogen-activated protein kinase 7 (MKK7) associates with RIPK2 and is essential for RIPK2's stabilization of c-Myc. We found that the kinase-dead form (K47A and S176A) of RIPK2 can still stabilize c-Myc (data not shown), suggesting that RIPK2 does not directly phosphorylate c-Myc$^{S62}$. To identify the key mediator of RIPK2's indirect phosphorylation of c-Myc$^{S62}$, we conducted mass spec-based interactome profiling analysis. We immunoprecipitated (IP) RIPK2 complexes and subjected the IP products to label-free proteomic analysis using gel-enhanced liquid chromatography-tandem mass spectrometry (GeLC-MS/MS). A total of 1,189 proteins were identified with an FDR of <1%. After statistical analysis, a total of 226 proteins were identified as candidate proteins associated with RIPK2 (FIG. 5A). One of these interacting proteins is MKK7 (FIG. 5B), an upstream kinase of JNK, which in turn can directly phosphorylate the S62 of c-Myc. Moreover, using in-situ proximity ligation assay (PLA), we confirmed that RIPK2 colocalizes with MKK7 (FIG. 5C). The PLA method uses two primary antibodies to recognize a pair of proteins and then use secondary antibodies tagged with short DNA strands to bind with the primary antibodies. If the two DNA strands are within ~40 nm, they are ligated and rolling cycle amplification with fluorescently conjugated nucleotides is used to visualize interaction sites. In this assay, we used the Duolink In Situ Red Starter Kit Mouse/Rabbit (Sigma) according to the manufacturer's protocol. Briefly, after fixing cells and blocking samples, we incubated samples sequentially with 1) both a rabbit anti-RIPK2 antibody and a mouse anti-MKK7 antibody, 2) a pair of PLA probes, 3) ligation solution, and 4) amplification solution. We visualized nuclei using 4'6-diamidino-2-phenylindole (DAPI) and then examined PLA signals under an All-in-One Fluorescence Microscope BZ-X710 (KEYENCE America). We included negative controls by omitting one of the two primary antibodies. Moreover, we found that knocking out MKK7 but not PRKDC, another RIPK2-interacting protein, significantly decreases c-Myc S62 phosphorylation and c-Myc protein abundance (FIG. 5D).

Figure 6:
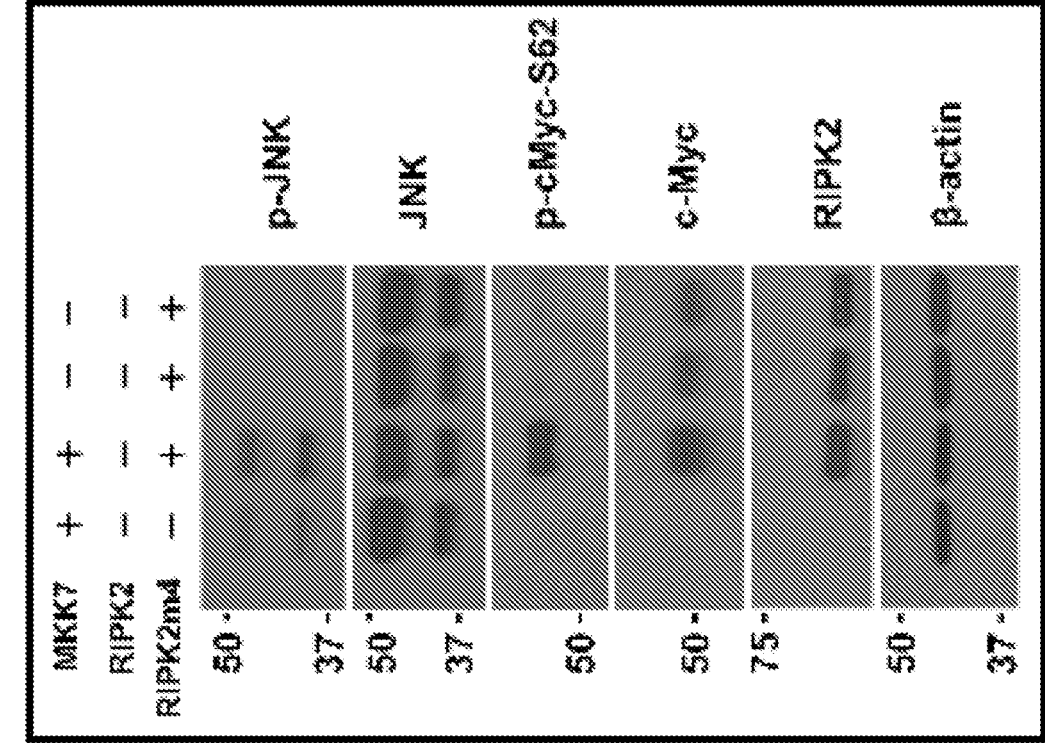
FIG. 6 shows that RIPK2 induces MKK7-dependent JNK activation and c-Myc stabilization. RIPK2m4: a mutant form that is resistant to Cas9 cleavage.

RIPK2 induces MKK7-dependent JNK activation and c-Myc stabilization. The overexpression of RIPK2 in HEK293T/RIPK2$^{-/-}$ cells significantly (p<0.01) increased the abundance of active JNK (pT183/Y185) but not total JNK, suggesting that RIPK2 overexpression activates JNK. RIPK2 overexpression also significantly increased the abundance of pS62-c Myc and c-Myc. In addition, MKK7-KO dramatically suppressed RIPK2-induced JNK activation, c-Myc$^{S62}$ phosphorylation and c-Myc accumulation, suggesting that RIPK2-induced JNK activation and c-Myc stabilization is MKK7-dependent (FIG. 6).

Figure 7:
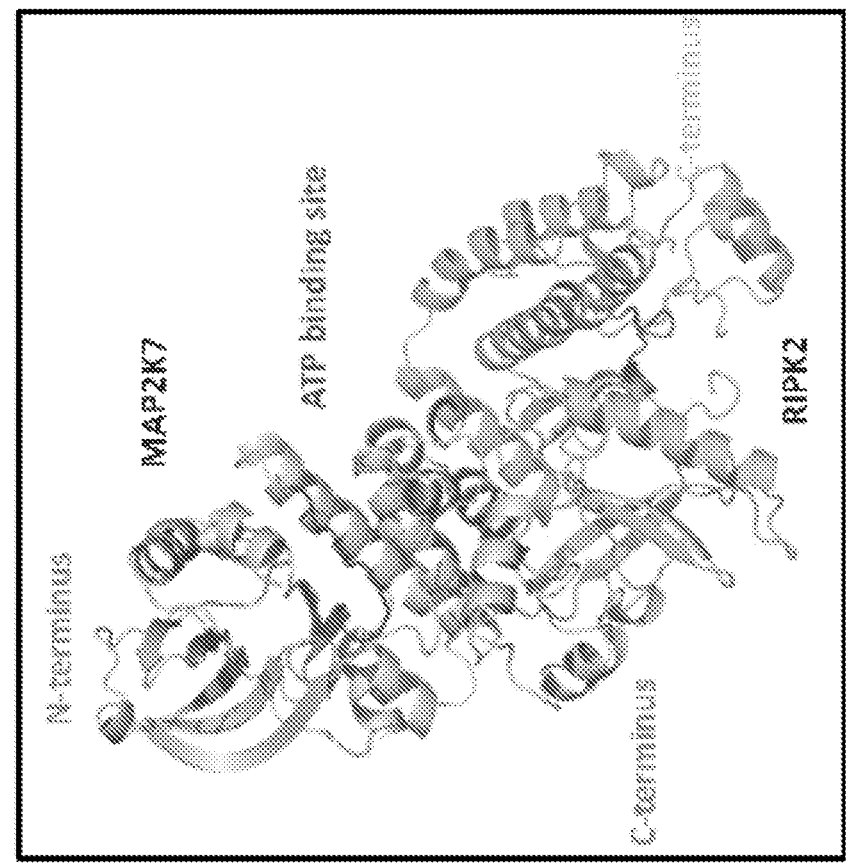
FIG. 7 shows that RIPK2 binds to MKK7 in a head-to-tail fashion. The N-terminal kinase domain of RIPK2 binds to the C-terminal kinase domain of MKK7.

RIPK2 binds to MKK7 in a head-to-tail fashion. Our structural modeling suggested that RIPK2 interacts with MKK7 in a head-to-tail fashion. The complex appears to be stabilized by small hydrophobic core residues (P11, W40, H37, H16, K17, and P14) located at the N-terminus of RIPK2 (FIG. 7).

RIPK2 binds to FASN and nucleocytoplasmic transport machinery proteins Ran, Importin β-1, and Exportin-1. In addition to MKK7, our interactome analysis identified FASN, Ran, Importin β-1, and Exportin-1 as proteins associated with the kinase domain of RIPK2 (FIG. 8), a domain necessary for RIPK2's stabilization of c-Myc (data not shown). Notably, FASN is the enzyme that catalyzes the biosynthesis of palmitates while the three nucleocytoplasmic transport machinery proteins were identified as S-palmitoylated proteins.

Figure 9:
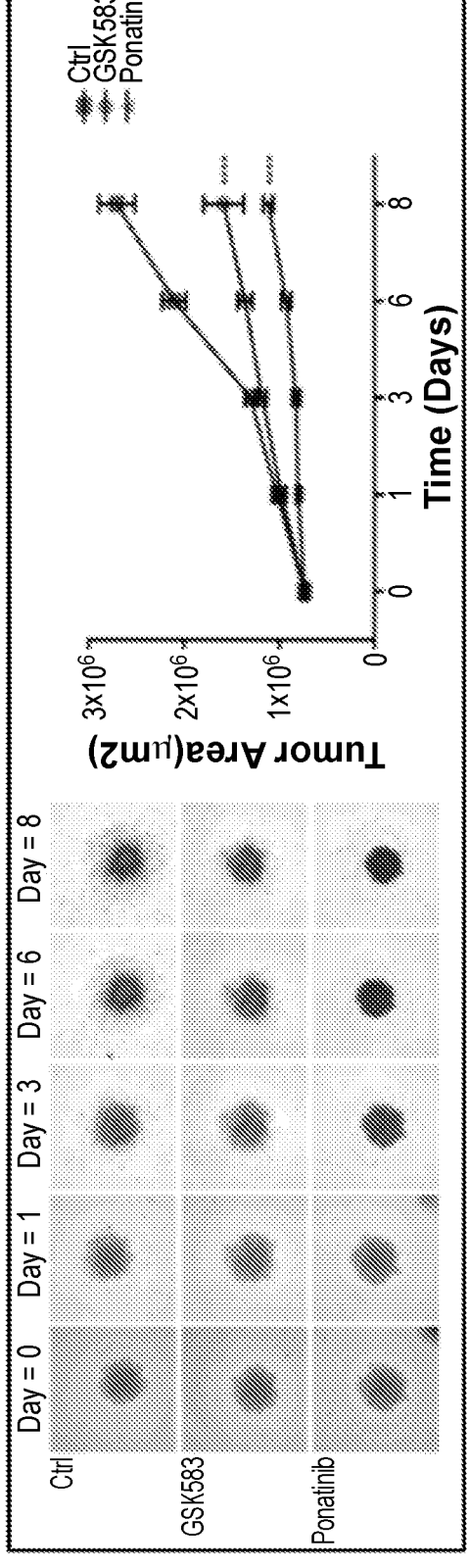
FIG. 9 shows that pharmacological inhibition of RIPK2 suppresses PC3 cell invasion in 3D culture. PC3 cells were cultured in 3D and treated with potent RIPK2 inhibitors GSK583 (10 μM) and Ponatinib (5 μM) in 10% FBS-containing media for 8 days.
Figure 10:
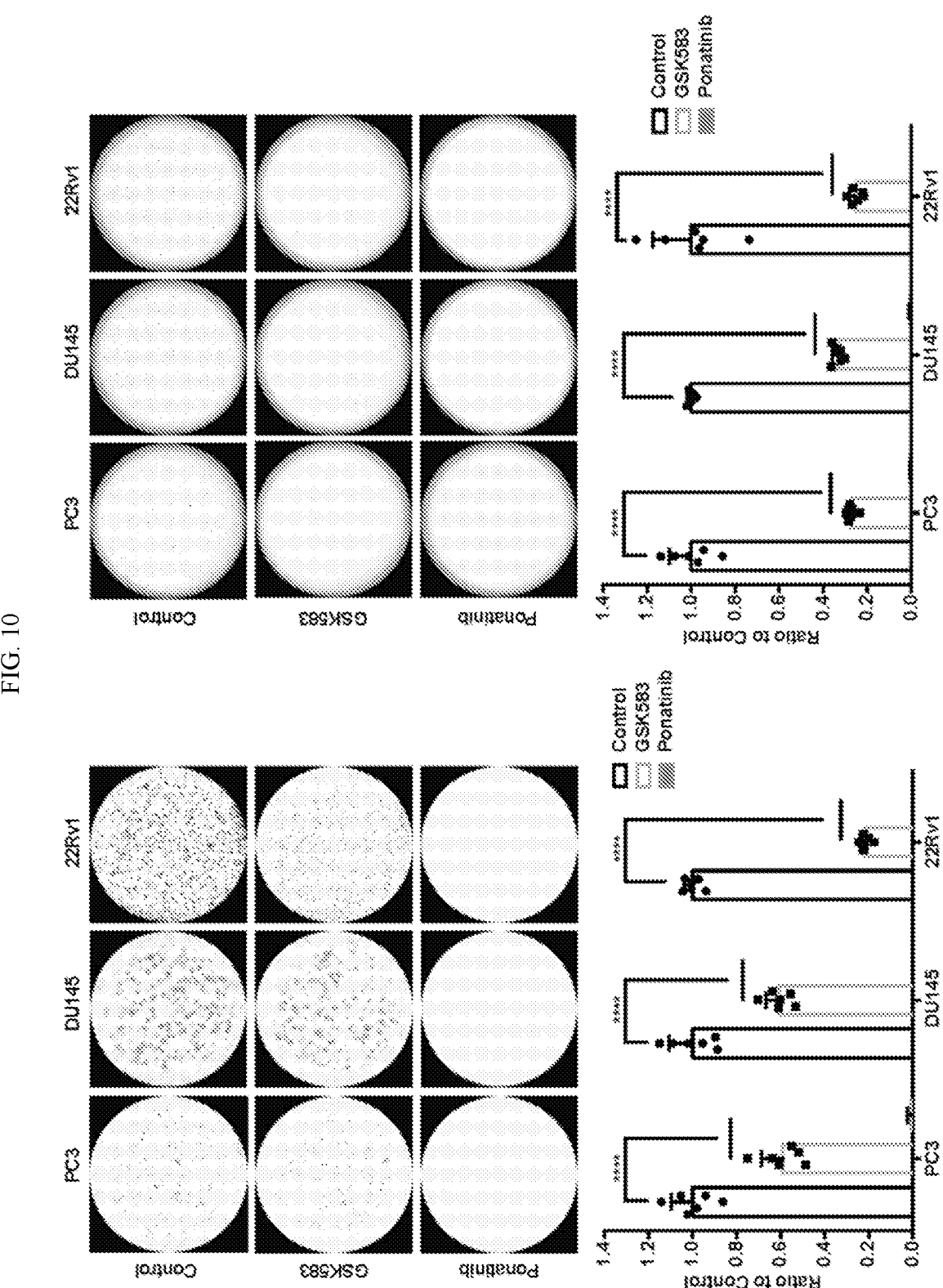
FIG. 10 shows that pharmacological inhibition of RIPK2 suppresses the colony formation of PCa cells in vitro. PC3, DU145, and 22Rv1 cells were treated with potent RIPK2 inhibitors GSK583 (10 μM) and Ponatinib (5 μM) and their anchorage-dependent (left) and anchorage-independent (right) colony formation was compared.
Figure 11:
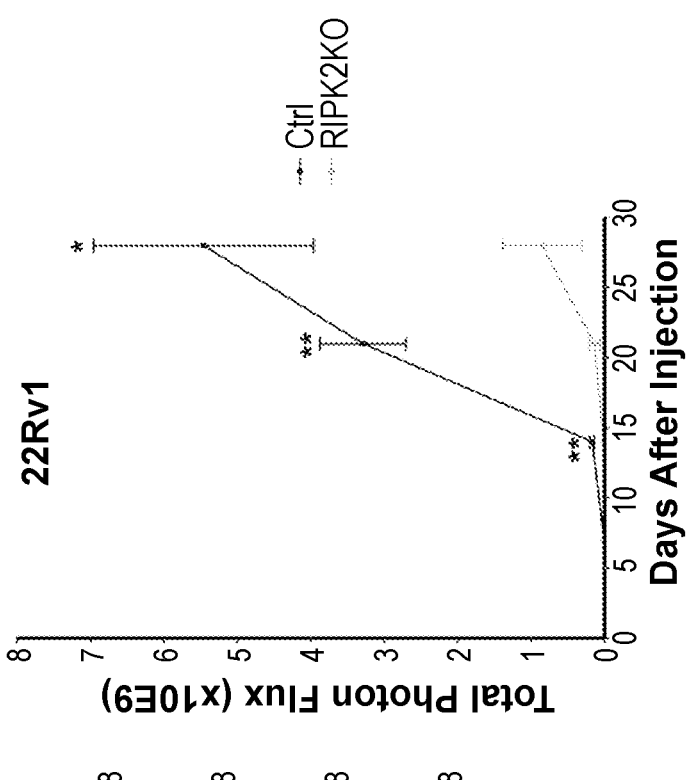
FIG. 11 shows that RIPK2 knockout significantly suppresses prostate cancer metastasis in intact mice. One million mCPRC 22Rv1 cells with or without RIPK2 knockout were injected into the left cardiac ventricle of each male SCID-Beige mouse. Tumor metastasis was measured by an IVIS Optical Imaging system every week.
Figure 11:
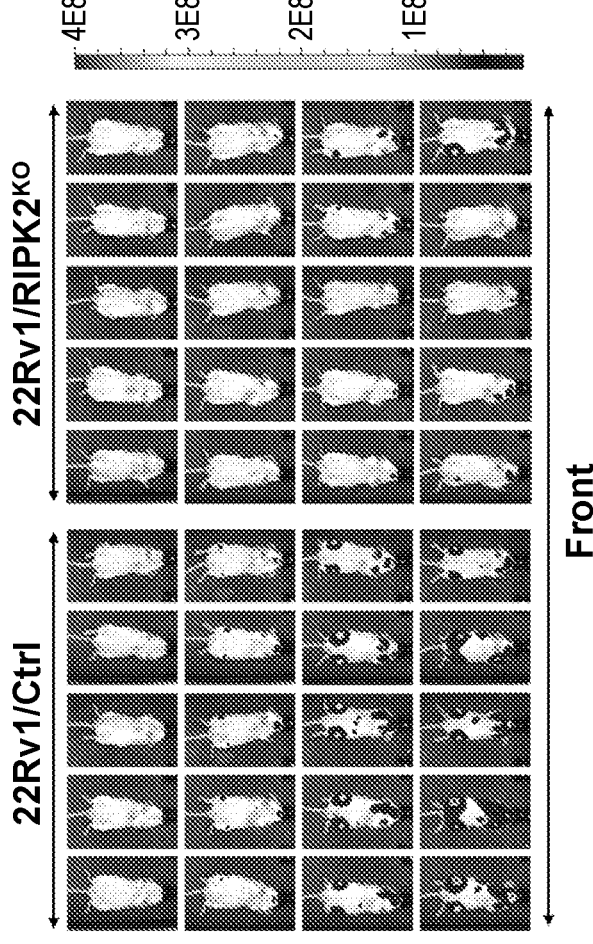
Figure 12:
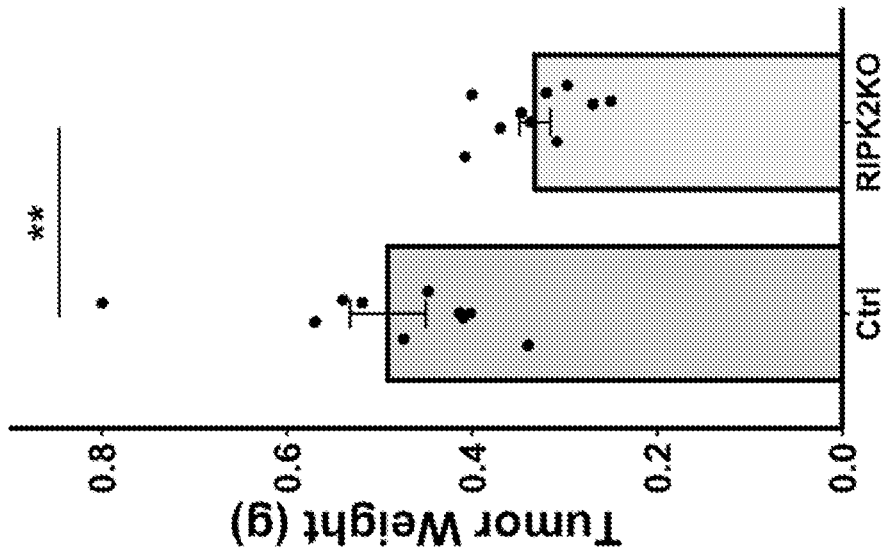
FIG. 12 shows that RIPK2 knockout significantly decreases tumor growth in intact mice. One million 22Rv1 cells with or without RIPK2 knockout were subcutaneously injected at both flanks of each male SCID-Beige mouse. Tumor length and width were measured by a caliper and tumor volumes were calculated using the formula $V=(width^2 \times length)/2$.
Figure 12:
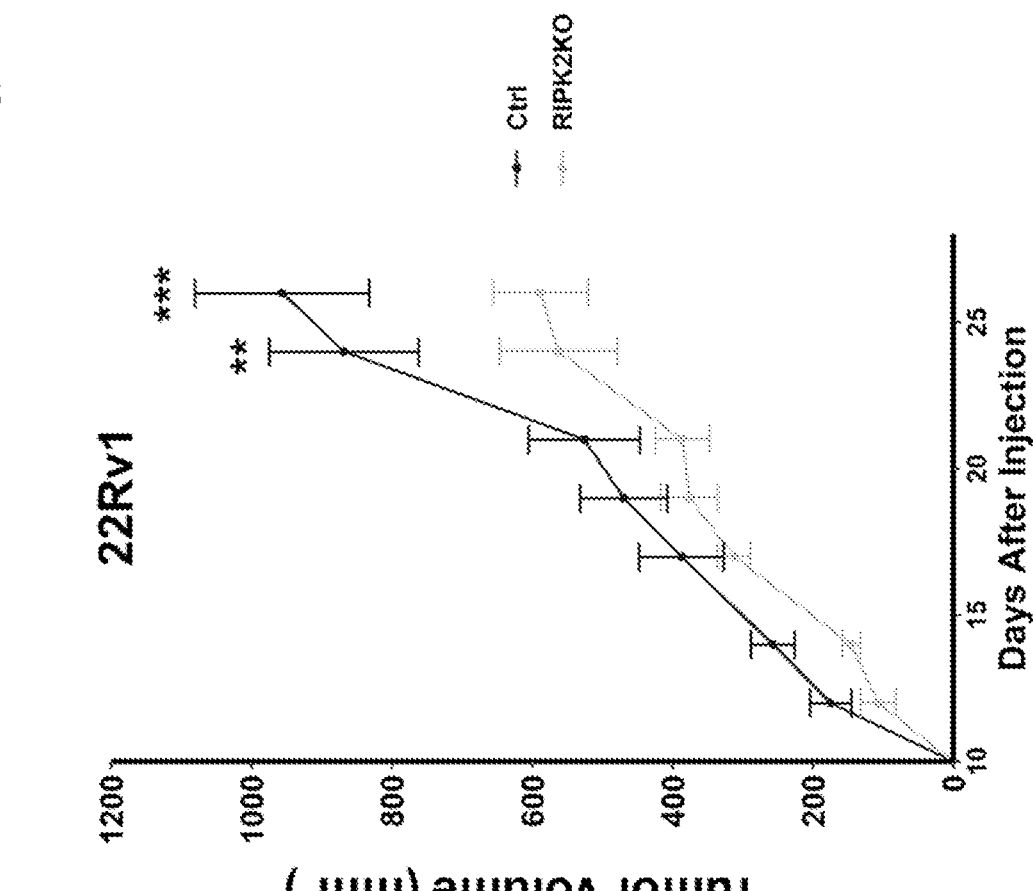

Pharmacological inhibition of RIPK2 suppresses PCa cell invasion in vitro. RIPK2 inhibition by potent RIPK2 inhibitors GSK583 and Ponatinib significantly decreased PC3 cell invasion in 3D culture (FIG. 9). This suggests that RIPK2 inhibitors can potentially benefit mCRPC patients.

Genetic deletion of RIPK2 suppresses PCa metastasis in vivo. RIPK2 knockout by CRISPR/Cas9 significantly suppressed mCRPC 22Rv1 metastasis in male mice. This suggests that targeting RIPK2 can potentially abolish or delay PCa metastasis in patients.

Genetic deletion of RIPK2 reduces PCa tumor growth in vivo. RIPK2 knockout by CRISPR/Cas9 significantly reduced PCa tumor growth in male mice. This suggests that targeting RIPK2 can potentially shrink tumors in mCRPC patients.

Pharmacological inhibition of RIPK2 suppresses PCa metastasis in vivo. RIPK2 inhibition by potent RIPK2 inhibitor GSK583 significantly decreased mCRPC 22Rv1 metastasis in male mice. This suggests that RIPK2 inhibitors can potentially benefit mCRPC patients.

Frequent co-amplification of RIPK2 and MYC genes in mCRPC patients. RIPK2 and MYC genes are co-amplified in 13% mCRPC patients. This subset of patients may benefit from precision treatment using potent RIPK2 inhibitors.

Frequent co-amplification of RIPK2 and MYC genes in breast cancer patients. RIPK2 and MYC genes are co-amplified in 18% of breast cancer patients. This subset of patients may benefit from precision treatment using potent RIPK2 inhibitors.

Example 2

Delineate the Molecular Effectors of the RIPK2/MKK7/JNK/c-Myc Pathway in PCa Metastasis and Therapeutic Resistance to Antiandrogens While not wishing to be bound by any particular theory, we believe that RIPK2 directly interacts with MKK7 and their association activates JNK, which in turn phosphorylates c-Myc$^{S62}$ and results in the accumulation of c-Myc, consequently promoting PCa metastasis and enzalutamide resistance. Our rationale is based on our preliminary findings shown in FIGS. 1-13. In addition, Myc has so far been considered undruggable because its surface topology lacks deep pockets for the design of potent small-molecule binders and active JNK phosphorylates c-myc$^{S62}$ and protects c-Myc from proteasomal degradation. Significantly, RIPK2 inhibitors can be used to treat mCRPC driven by hyperactive c-Myc signaling that results from RIPK2 gene amplification and overexpression. The concepts that RIPK2 drives PCa progression to mCRPC and that RIPK2 can serve as a novel drug target for mCRPC treatment is significant. In addition, the RIPK2/MKK7/JNK/c-Myc pathway is a completely new signaling pathway.

We will also delineate the molecular details of the RIPK2/MKK7/JNK/c-Myc pathway using HEK293T cells, which are easy to culture and provide high transfection efficiency. Key experiments will be repeated in multiple PCa cell lines.

We will also determine whether the RIPK2-MKK7 association depends on the polyubiquitination (polyUb) of RIPK2. Previous studies suggested that RIPK2 polyUb is a prerequisite to RIPK2 association with the IκB kinase (IKK) and TAB/TAK complexes, whose formation leads to the activation of the downstream NF-κB and MAPK signaling pathways. Therefore, it is possible that the RIPK2-MKK7 association also depends on the polyUb of RIPK2. To test this hypothesis, we will IP MKK7 complexes from HEK293T cells using an anti-MKK7 antibody and probe RIPK2 by IB analysis using a high-quality anti-RIPK2 antibody (Cell Signaling Tech., #4142). We will measure the apparent molecular weight (Mw) of the RIPK2 band(s) to determine whether RIPK2 is predominantly poly-ubiquitinated. The presence of a dominant band at about 61 kDa (the theoretical Mw of RIPK2) indicates that MKK7 binds to non-ubiquitinated RIPK2. In contrast, the presence of a dominant band at ≥70 kDa suggests that MKK7 binds to ubiquitinated RIPK2. If the latter is the case, we will determine the major polyUb linkages by performing IB analysis using pan and linkage-specific anti-ubiquitin antibodies. Previous studies showed that RIPK2 may undergo "Lys-63"-, "Lys-48"-, and "Met-1"-linked polyubiquitination. Thus, we will use K63/K48/M1 linkage-specific anti-ubiquitin antibodies (Cell Signaling Technology and Millipore) to determine the major polyUb linkages by IB analysis. Furthermore, we will perform site mutagenesis studies to identify the lysine residue(s) whose polyUb is essential for the RIPK2-MKK7 interaction. Our study suggested that MKK7 binds to RIPK2 kinase domain (FIG. 5B), which contains three ubiquitination sites (K182, K203, and K209). We will mutate each site from lysine to arginine, ectopically express Flag-tagged wild-type vs. mutant RIPK2 into stable HEK293T/RIPK2–/– cells that we have already generated, IP RIPK2 complexes using an anti-Flag antibody, and perform IB analysis to probe the relative abundance of MKK7 in the complexes. In addition, we will perform in situ PLA analysis (as described in preliminary result C1d) and quantify the PLA signal difference using ImageJ (v1.52a) to determine whether the RIPK2-MKK7 association is decreased by the site mutations.

We will also map the interaction interface of RIPK2 and MKK7. Our structural model suggested that RIPK2 may directly bind to MKK7 (FIG. 7). If RIPK2-MKK7 association is independent of RIPK2 polyUb, we will perform pull-down assays using purified recombinant proteins to confirm direct RIPK2-MKK7 interaction. We will express recombinant proteins of RIPK2 tagged with C-terminal His6 and MKK7 tagged with C-terminal GST in HEK293T cells. We will use Ni-NTA agarose beads (Thermo) to purify RIPK2-His6 and use Glutathione agarose beads (Thermo) to purify MKK7-GST, followed by SDS-PAGE analysis to verify their purity. We will incubate purified RIPK2-His6 and MKK7-GST with either Ni-NTA beads or Glutathione beads, followed by bead washing, protein elution, and IB analysis to detect the RIPK2-MKK7 association. Subsequently, we will apply enzymatic mass spec-based footprinting to verify or identify the putative interaction interface. Briefly, we will perform tryptic hydrolysis by adding bovine TPCK-treated trypsin (Sigma) to aliquots of purified RIPK2-His6 and MKK7-GST alone, or in combination to obtain the RIPK2-His6/MKK7-GST complex, at an enzyme/substrate ratio of 1:100 (w/w), followed by incubating the mixtures overnight at 37° C. We will desalt the resulting peptide mixture using C18 spin columns and analyze the desalted samples using an EASY-nLC 1200 ultraperformance liquid chromatography (UPLC) system coupled with an Orbitrap Fusion Lumos Tribrid mass spectrometer (Thermo). We will perform label-free mass spec comparison of the three samples (RIPK2-His6 alone, MKK-GST alone, and RIPK2-His6/MKK7-GST complex) to identify the "trypsin-insensitive" interaction interface, which can be revealed by differences in mass spec intensities. Alternatively, if RIPK2 polyUb is essential for the association, we will generate a panel of GST-fusion proteins containing a variety of fragments of MKK7, immobilize each MKK7 fragment protein with Glutathione agarose beads, and incubate the beads with protein lysates extracted from HEK293T. After washing beads, we will elute bound proteins and perform IB analysis, using an anti-RIPK2 antibody, to determine which domain of MKK7 is both necessary and sufficient for RIPK2 binding. We will optimize our preliminary structural model for the RIPK2-MKK7 complex (FIG. 7) and identify hot-spot amino acid residues important for protein-protein interactions.

We will also determine whether RIPK2-induced JNK activation and c-Myc stabilization depend on RIPK2-MKK7 association. Our preliminary study suggested that RIPK2 induces MKK7-dependent JNK activation and c-Myc stabilization (FIG. 6). Here, we will determine whether it is the RIPK2-MKK7 association that induces JNK activation and c-Myc stabilization. Firstly, we will determine whether compared with expressing RIPK2 or MKK7 protein alone, co-expressing RIPK2 and MKK7 proteins significantly increases JNK activation and c-Myc stabilization in HEK293T/RIPK2–/– cells. Secondly, we will test whether disrupting RIPK2-MKK7 association, by mutating hotspot residues on RIPK2 (if RIPK2 polyUb is not important for RIPK2-MKK7 association) or MKK7 (if RIPK2 polyUb is important), can inhibit JNK activation and c-Myc stabilization. Our preliminary structural model suggests that the RIPK2-MKK7 complex is stabilized by small hydrophobic core residues (P11, W40, H37, H16, K17, and P14) located at the N-terminus of RIPK2 (FIG. 7). We will further optimize our structural model to identify the most important hot-spot residues. We will subject the RIPK2-Flag (or MKK7-GST) construct to site-directed mutagenesis to mutate candidate hot-spot residues of interest, followed by comparing the effects of JNK activation and c-Myc stabilization by wild-type vs. mutant RIPK2 (or MKK7) with IB analysis.

We will also test whether RIPK2 inhibitors block the RIPK2-MKK7 association. Firstly, we will ectopically express RIPK2-Flag in HEK293T/RIPK2–/– cells and treat the cells with potent RIPK2 inhibitors GSK583, Ponatinib, and Compound 38 (hereafter abbreviated as G/P/C) vs. DMSO. We will IP RIPK2 complexes using an anti-Flag antibody, followed by comparing the differences of MKK7 protein levels by IB analysis. In addition, we will IP MKK7 complexes using an anti-MKK7 antibody, followed by comparing the differences of RIPK2 protein abundance by IB analysis. Secondly, we will treat parental HEK293T cells with potent RIPK2 inhibitions G/P/C vs. DMSO, perform in situ PLA analysis as described in preliminary result C1d, and quantify the PLA signal difference using ImageJ (v1.52a).

Figure 4:
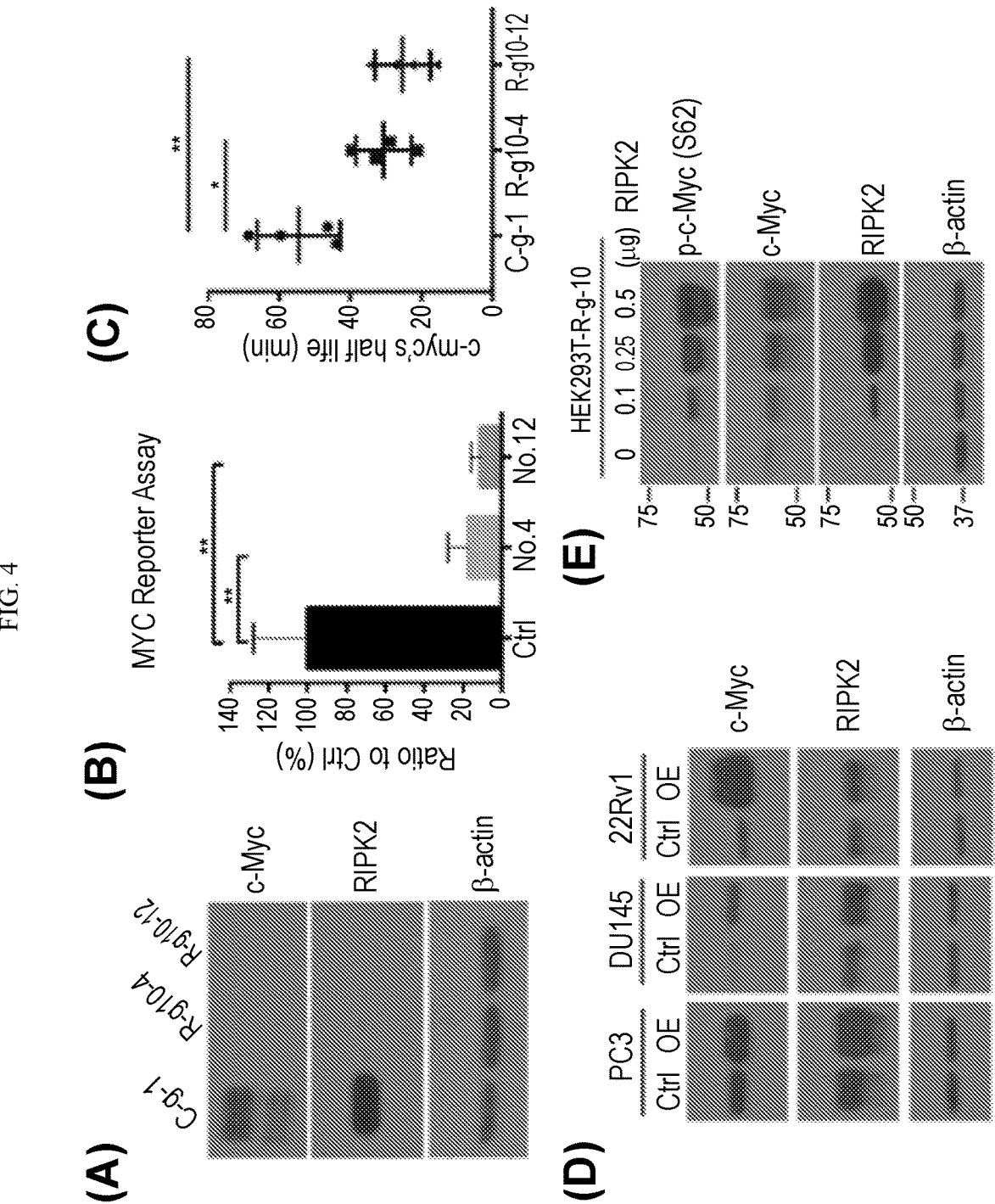
FIG. 4, panels (A)-(E), shows that RIPK2 regulates c-Myc abundance, activity, and stability. (A) RIPK2-KO dramatically decreases c-Myc protein abundance. (B) RIPK2-KO significantly decreases c-Myc activity. (C) RIPK2-KO significantly decreases c-Myc protein half-life. (D) RIPK2 overexpression increases c-Myc protein abundance. (E) RIPK2 overexpression increases c-Myc$^{S62}$ phosphorylation and c-Myc abundance in a dose-dependent fashion.

We will also determine whether the RIPK2/MKK7/JNK/c-Myc pathway is conserved in different PCa cell lines. After detailed pathway characterization in HEK293T cells, we will repeat key experiments in LNCaP, 22Rv1, DU145, PC3 cell lines to determine whether the RIPK2/MKK7/JNK/c-Myc signaling pathway is conserved in different PCa cell lines. We already found that RIPK2 deletion drastically decreased, whereas RIPK2 overexpression significantly increased, c-Myc protein abundance in PCa 22Rv1, DU145, and PC3 cells (FIG. 4). Here, we will determine whether co-expressing wild-type RIPK2 (RIPK2WT) and MKK7 (MKK7WT) significantly increases JNK activation and c-Myc stabilization, compared with a) expressing RIPK2WT alone, b) expressing MKK7WT alone, and c) co-expressing RIPK2 and MKK7 with hot-spot residue mutations. We will also determine whether RIPK2 inhibitors G/P/C decrease RIPK2/MKK7 colocalization, JNK activation, and c-Myc stabilization in parental LNCaP, 22Rv1, DU145, and PC3 cells by PLA and IB analyses.

While not wishing to be bound by any particular theory, we will also determine that genetic and pharmacological inhibition of RIPK2 suppresses PCa metastasis and enzalutamide resistance. Thus, we will focus on the biological effects of RIPK2 inhibition rather than RIPK2 overexpression.

Figure 13:
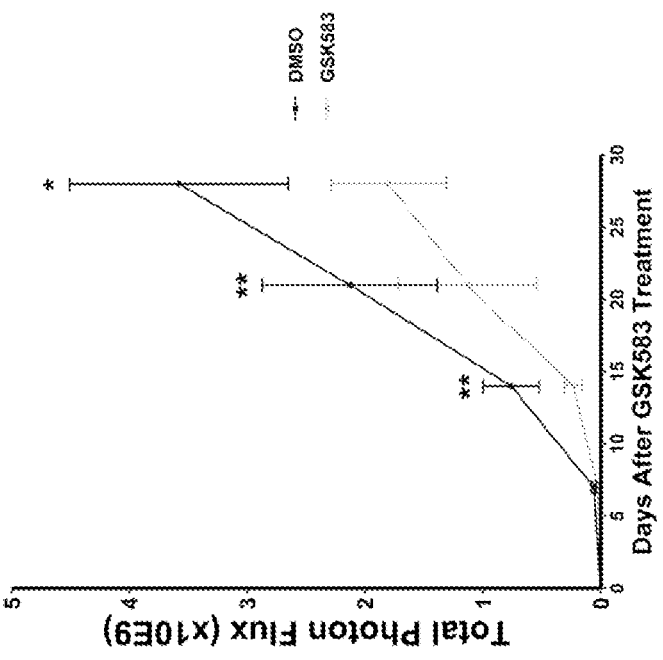
FIG. 13 shows that pharmacological inhibition of RIPK2 using GSK583, a specific RIPK2 inhibitor, significantly reduces prostate cancer metastasis in intact mice. One million mCPRC 22Rv1 cells with or without RIPK2 knockout were injected into the left cardiac ventricle of each male SCID-Beige mouse. A week later, mice were treated with 10 mg/g GSK583 or vehicle control (DMSO). Tumor metastasis was measured by an IVIS Optical Imaging system every week.
Figure 13:
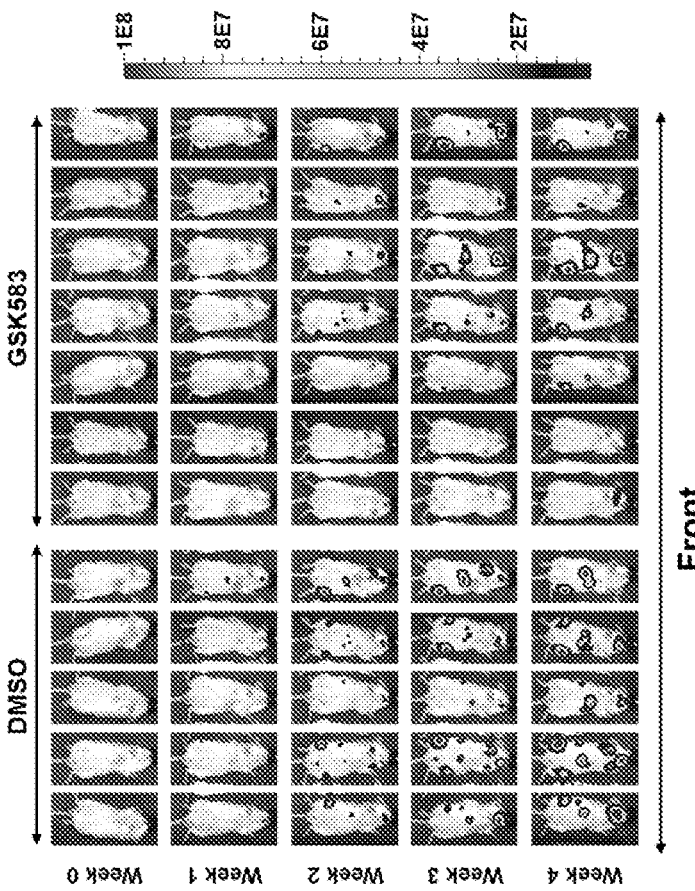
Figure 15:
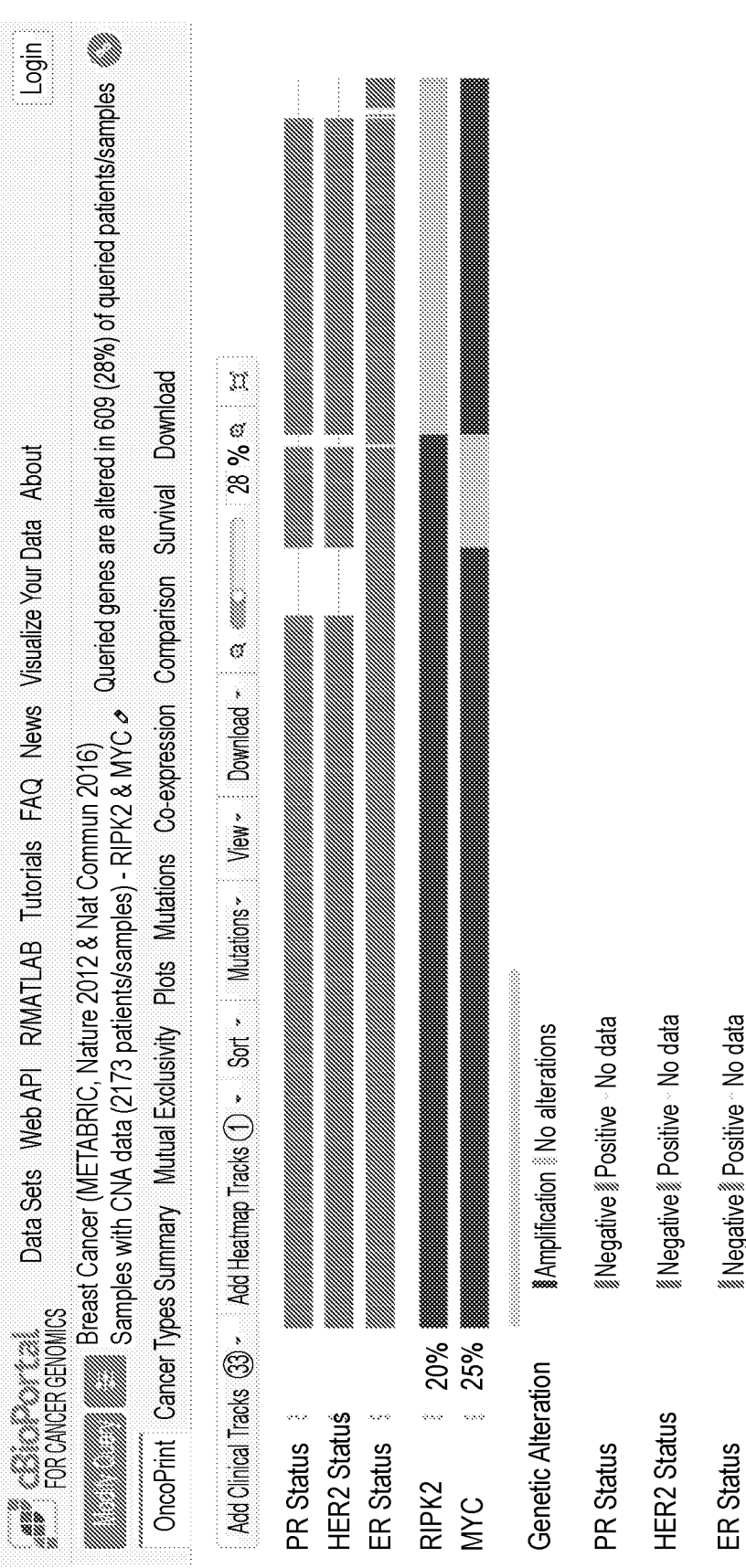
FIG. 15 shows a frequent co-amplification of the RIPK2 and MYC genes in breast cancer with different receptor status (n=2,173). RIPK2 was amplified in 20% of breast cancer, MYC in 25% of breast cancer, and both in 18% of breast cancer.

We will also determine whether genetic and pharmacological inhibition of RIPK2 suppresses PCa cell invasion, colony formation, and enzalutamide resistance in vitro. In our study, we showed that RIPK2-KO suppressed PCa cell invasion and colony formation (FIG. 2) and metastasis (FIG. 11) and that RIPK2 inhibition by G/P suppressed PC3 cell invasion (FIG. 9), colony formation (FIG. 10) and metastasis (FIG. 13). In addition, previous studies suggested that c-Myc drives castration resistance. Thus, we will determine whether RIPK2-KO re-sensitizes enzalutamide-resistant PCa cells to enzalutamide. We have already knocked out RIPK2 from enzalutamide-resistant 22Rv1 cells. Here, we will knock out RIPK2 from two additional enzalutamide-resistant cell lines MR49F and C4-2R25. We will use the MTS assay (Promega, #G3582) to compare the proliferation rates of cells with RIPK2-KO (vs. ctrl-KO) in the presence of enzalutamide (10-40 μM) (vs. DMSO). Furthermore, we will determine whether RIPK2 inhibition re-sensitizes enzalutamide-resistant PCa cells to enzalutamide. We will compare the proliferation rates of parental 22Rv1, MR49F, and C4-2R cells treated with enzalutamide plus a RIPK2 inhibitor G/P/C (vs. DMSO).

While not wishing to be bound by any particular theory, we will further confirm that genetic and pharmacological inhibition of RIPK2 suppresses PCa tumor growth, metastasis, and enzalutamide resistance in vivo. We will compare the following six groups: 1) tumor growth assay using PC3 cells with RIPK2-KO vs. ctrl-KO, 2) metastasis assay using luciferase-expressing PC3 cells with RIPK2-KO vs. ctrl-KO, 3) enzalutamide-resistance assay using 22Rv1 with RIPK2-KO vs. ctrl-KO cells: after the formation of ~200 mm3 tumors, mice will be treated with vs. without enzalutamide (30 mg/kg), 4) tumor growth assay using parental PC3 and 22Rv1 cells and mice treated with Compound 3 (a RIPK2-specific inhibitor in phase I clinical trials) vs. vehicle control, 5) metastasis assay using luciferase-expressing PC3 and 22Rv1 cells and mice treated with Compound 3 vs. vehicle control, and 6) enzalutamide-resistance assay using 22Rv1 cells: after the formation of ~200 mm³ tumors, mice will be treated with enzalutamide (30 mg/kg) plus Compound 3 vs. DMSO. The in vivo PCa assays will be conducted using our standard animal experiment protocols. Briefly, for tumor growth assay, we will perform subcutaneous injection of PCa cells into the flanks of male athymic nude (nu/nu) mice (4-5 weeks old) (Charles River), measure the lengths of minor and major tumor aces by caliper, and calculate tumor volumes using the formula of $V=(width^2 \times length)/2$. For metastasis assay, we will inoculate luciferase-expressing PCa cells intracardially into male SCID/Beige mice (6-8 weeks old) and image mice weekly with bioluminescence imaging using a Xenogen IVIS Spectrum Imaging System (PerkinElmer). For enzalutamide-resistance assay, after the formation of 200 mm³ tumors, we will treat mice with enzalutamide and/or Compound 3 and measure tumor volumes. To reach a statistically meaningful conclusion ($p<0.05$), 6 mice per group will be used for the tumor growth and enzalutamide-resistance assays and 10 male mice per group will be used for the metastasis assay. In addition, we will perform IHC analysis to measure protein expression levels of RIPK2, c-Myc, pJNK, JNK, PCNA (proliferation), and cleaved caspase-3 (apoptosis). We will analyze 1) survival rates by log-rank test and presented by Kaplan-Meier Survival Curve, 2) weight changes by ANOVA with Tukey-Kramer post hoc test on percentage of initial weight at day 1, 3) tumor growth by log-rank test of tumor doubling time distribution or by multivariate growth curve analysis, 4) metastasis by visual assessment and by mean photon intensity of region of interests in two groups by two-tailed Student's t-test.

We will also confirm c-Myc as a key mediator of RIPK2-driven mCRPC development.

We will also determine whether c-Myc overexpression largely abolishes the tumor-suppressive effects of RIPK2 KO and inhibition. In our preliminary results, RIPK2-KO significantly decreased colony formation capabilities of 22Rv1, DU145, and PC3 cells (FIG. 2). We have subcloned c-Myc-Flag into the all-in-one doxycycline (Dox)-inducible lentiviral vector pCW57-MCS1-P2A-MCS2 (Addgene) and sequenced the construct on both strands to verify sequence integrity. Here, we will stably transfect the Dox-inducible c-Myc-Flag plasmid into 22Rv1, DU145, PC3, MR49F, and C4-2R cells with vs. without stable RIPK2 knockout. We will confirm a minimal leaky expression of c-Myc-Flag in the absence of Dox and optimize Dox concentration to restore the protein levels of c-Myc in RIPK2-KO cells to those in Dox-untreated control cells without RIPK2-KO. We will generate two sets of cells for cell invasion and colony formation assays: 1) PCa/RIPK2–/–/MYC-tet (vs. control) cells treated with Dox vs. DMSO to induce c-Myc expression and 2) PCa/MYC-tet cells treated with G/P/C vs. DMSO to inhibit RIPK2 activity and with Dox vs. DMSO to induce c-Myc overexpression. For both experimental sets, we will perform 3D invasion, clonogenic assay, and soft agar assay. We will conduct a statistical analysis using the same protocol for the preliminary results (FIG. 2). In addition, we will determine whether the Dox-induced expression of c-Myc significantly increases the resistance of 22Rv1/RIPK2–/–, MR49F/RIPK2–/–, and C4-2R/RIPK2–/– cells to enzalutamide treatment.

We will also determine whether c-Myc inhibition and knockdown significantly impair RIPK2's PCa-promoting effects in vitro. We will stably transfect RIPK2 plasmid (vs. control vector) into parental LNCaP, VCaP, 22Rv1, DU145, and PC3 cells. After confirming the overexpression of RIPK2, we will perform 3D invasion assay (using PC3), clonogenic and soft agar assays (using PC3/DU145/22Rv1), and enzalutamide resistance assay (using LNCaP and VCaP) in the presence vs. absence of 10058-F4 (a potent c-Myc-specific inhibitor). The goal is to determine a) whether RIPK2 overexpression promotes PCa cell invasion, colony formation, and enzalutamide resistance and b) whether c-Myc inhibition can largely abolish the effects by RIPK2 overexpression. Next, from the stable cell clones with RIPK2 overexpression, we will knock down c-Myc using a lentiviral c-Myc shRNA (Addgene, #29435) as described, followed by D3 analysis to confirm c-Myc depletion. We will determine whether c-Myc knockdown significantly inhibits RIPK2-enhanced cell invasion, colony formation, and enzalutamide resistance compared to control cells.

We will also determine whether c-Myc overexpression abolishes the inhibitory effects of RIPK2 KO on PCa tumor growth, metastasis, and enzalutamide resistance in vivo. We will use limiting dilution to isolate PC3 and 22Rv1 single-cell clones with both stable RIPK2-KO (vs. ctrl-KO) and Dox-inducible c-Myc expression. For each cell line, we will compare mice fed with Dox vs. control vehicle. We will perform in vivo tumor growth, metastasis, and enzalutamide resistance assays as well as data analysis and IHC analysis as described herein.

Expected Outcomes: The RIPK2/MKK7/JNK/c-Myc pathway is distinct from the canonical RIPK2-NFκB/MAPK pathway. Moreover, our structural modeling analysis suggested that unmodified RIPK2 may directly bind to MKK7. Therefore, we predict that the RIPK2-MKK7 association is independent of RIPK2 polyUb. We anticipate that a) RIPK2 and MKK7 directly interact with each other, b) RIPK2-induced JNK activation and c-Myc stabilization depends on direct RIPK2-MKK7 interaction, c) potent RIPK2 inhibitors G/P/C can disrupt RIPK2-MKK7 association, and d) the RIPK2/MKK7/JNK/c-Myc pathway is conserved in all the tested PCa cell lines. We expect genetic and pharmacological inhibition of RIPK2 can at least significantly suppress PCa metastasis and enzalutamide resistance. We anticipate confirming that c-Myc is a key mediator of RIPK2-driven PCa metastasis and enzalutamide resistance.

If commercially available anti-MKK7 antibodies do not work well for IP, we will fuse MKK7 with a Flag tag and ectopically express MKK7-Flag in HEK293T cells, followed by using an anti-Flag antibody to pull down MKK7 complexes. If RIPK2 and MKK7 do not directly interact with each other, we will identify the intermediate protein(s) that directly bind to both RIPK2 and MKK7. Briefly, we will subject isolated MKK7 complexes to LC-MS/MS analysis to identify MKK7-interacting proteins and overlap them with proteins interacting with RIPK2. If neither RIPK2 KO nor RIPK2 inhibition can suppress enzalutamide resistance, we will investigate whether targeting RIPK2 can suppress PCa cell resistance to docetaxel and cabazitaxel, two common chemotherapies for mCRPC.

Example 3

Elucidate the RIPK2/FASN/S-Palmitoyl-RAN Pathway and its Roles in mCRPC Development Hypothesis: RIPK2 serves as a scaffold protein to bring FASN and Ran/importin β1/exportin-1 in proximity and thus facilitates FASN-promoted S-palmitoylation of Ran, importin β1 and exportin-1. This in turn modulates the nucleocytoplasmic transport of certain oncoproteins and tumor suppressor proteins, consequently promoting PCa metastasis and drug resistance. Rationale: The rationale is based on the literature and our preliminary findings that 1) S-palmitoylation is an important post-translational modification (PTM) that regulates protein localization, activity, stability, and complex formation, 2) RIPK2 interacts with FASN (FIG. 8), an enzyme that catalyzes de novo palmitate synthesis and promotes protein S-palmitoylation, 3) FASN is a metabolic PCa oncogene, 4) 80% of RIPK2-interacting proteins, including nucleocytoplasmic machinery proteins Ran, importin β1 and exportin-1, were previously identified as S-palmitoylated proteins, 5) Ran, importin β1 and exportin-1 are key proteins for nucleocytoplasmic transport, 6) aberrant nucleocytoplasmic transport of oncoproteins and tumor suppressor proteins promotes cancer, and 7) targeting nuclear export demonstrated clinical activity in mCRPC patients refractory to second-line anti-androgenic agents. Significance: RIPK2 can be developed into a novel drug target for the treatment of mCRPC driven by aberrant nucleocytoplasmic transport caused by RIPK2 amplification and overexpression. Innovation: 1) the concept that RIPK2 regulates protein S-palmitoylation is novel, 2) the concept that the S-palmitoylation modulates nucleocytoplasmic transport is novel, 3) the combination of leading-edge proteomics technologies is novel.

We will also determine whether RIPK2 promotes FASN-dependent S-palmitoylation of Ran, importin β1 and exportin-1.

We will also determine whether RIPK2 enhances the S-palmitoylation levels of Ran, importin β1 and exportin-1. We will apply two complementary approaches, low-background acyl-biotinyl exchange (LB-ABE) and metabolic labeling with a palmitic acid analog followed by click chemistry (MLCC), to compare the S-palmitoylation levels of Ran, importin β1 and exportin-1 in HEK293T cells under four conditions: ctrl-KO, RIPK2-KO, ctrl-OE, and RIPK2-OE (n=3). In the LB-ABE approach, we will lyse cells with a 4% SDS-containing buffer, reduce disulfide bonds with 50 mM TCEP, alkylate non-S-palmitoylated cysteine residues with 50 mM N-ethylmaleimide (NEM) followed by 25 mM 2,2'-dithiodipyridine (DTDP), cleave off S-palmitoyl groups from cysteine residues (S-palmitoylation sites) with 2 M neutral hydroxylamine, and biotinylate newly formed free cysteine residues with 1 mM Biotin-HPDP. We will enrich in vitro biotinylated (i.e., formerly S-palmitoylated) proteins with streptavidin beads and elute Biotin-HPDP-conjugated proteins with TCEP. We will use target-specific antibodies to probe the relative abundance of Ran, importin β1 and exportin-1 across the four cell-conditions before and after S-palmitoyl protein enrichment. We will use ImageJ (v1.52a) to perform densitometric analysis, determine the relative S-palmitoylation levels by calculating the (S-palmitoyl form)/(total form) ratios, and apply two-tailed Student's t-test to calculate p values. In the MLCC approach, we will incubate the 4-condition cells with 100 μM w-alkynyl palmitic acid (Alk-C16) (Avanti, #900400) for 6 h (n=3). Over time, Alk-C16 will be metabolically incorporated onto S-acylation sites. After protein extraction, we will react cellular proteins with biotin-azide via click chemistry in vitro, so Alk-C16-proteins are conjugated with biotin-azide. We will isolate in vitro biotinylated (formerly S-acylated) proteins by streptavidin affinity purification, before eluting bound proteins by boiling samples in 3× protein loading buffer containing 2 mM biotin and 20 mM DTT for 10 min. We will subject the enriched proteins and input proteins to D3 analysis using target-specific antibodies, so as to quantify the relative abundance of the S-acylated form and the total form, respectively, which in turn provides relative S-acylation levels. We will use ImageJ (v1.52a) to perform densitometric analysis and apply two-tailed Student's t-test to calculate p values. We will repeat the procedures on PCa LNCaP, 22Rv1, DU145, and PC3 cells.

We will also determine whether RIPK2-enhanced S-palmitoylation of Ran, importin β1 and exportin-1 is FASN-dependent. We will compare the S-palmitoylation levels of Ran, importin β1 and exportin-1 in RIPK2-over-expressing HEK293T cells under four different conditions: 1) ctrl-shRNA, 2) FASN-targeting shRNA, 3) DMSO, and 4) FASN-specific inhibitor cerulenin. We will apply both LB-ABE and MLCC to determine whether targeting FASN suppresses RIPK2-enhanced S-palmitoylation of Ran, importin β1 and exportin-1.

We will also generate a protein-protein interaction map of RIPK2, FASN, Ran, importin β1 and exportin-1. Firstly, we will map the PPI topology of the five proteins using both co-IP and PLA analyses. In the co-IP analysis, we will use one protein as a bait protein, perform IP using an anti-bait antibody, and probe the other four proteins by IB analysis. We will repeat the procedure for all the five proteins, followed by mapping the bait-prey relationships. In PLA analysis, we will probe which proteins are in close proximity by analyzing every protein pair as described in FIG. 5. The five proteins may form up to 10 heterodimers. Secondly, we will generate structural models for the RIPK2-FASN, RIPK2-Ran, RIPK2-importin β1, and RIPK2-exportin-1 complexes and map potential interfaces by homology mod-eling and protein-protein docking. Thirdly, we will test whether RIPK2 association with these proteins can be abolished by deletion of RIPK2 segments involved in pro-tein-protein association. We will perform domain deletion and test whether a Flag-tagged mutant is less effective than Flag-tagged wild-type RIPK2 in binding to FASN, Ran, importin β1, and exportin-1. We will ectopically express Flag-tagged wild-type vs. mutant RIPK2 in HEK293T/RIPK2$^{-/-}$ cells, isolate RIPK2 complexes by IP using an anti-Flag antibody, and perform IB analysis to quantify the protein levels of FASN, Ran, importin β1 and exportin-1 in the complexes. Fourthly, we will test whether RIPK2 asso-ciation with these proteins can be alleviated by mutating hot-spot residues identified based on the structural models built earlier and the domain deletion result. We will subject the Flag-tagged wild-type RIPK2 construct to site-directed mutagenesis using the QuikChange II Site-Directed Muta-genesis Kit (Agilent). We will ectopically express Flag-tagged wild-type vs. mutant RIPK2 in HEK293T/RIPK2$^{-/-}$ cells, isolate RIPK2 complexes by IP using an anti-Flag antibody, and perform IB analysis to quantify the protein levels of FASN, Ran, importin β1 and exportin-1 in the complexes. Fifthly, we will determine whether impaired RIPK2 association with FASN suppresses the S-palmitoy-lation of Ran, importin β1 and exportin-1. We will ectopi-cally express Flag-tagged wild-type vs. mutant RIPK2 (with impaired interaction with FASN) in HEK293T/RIPK2-/- cells, and measure the S-palmitoylation level changes of Ran, importin β1 and exportin-1 by LB-ABE and MLCC. Finally, we will determine whether impaired RIPK2 asso-ciation with Ran, importin β1 or exportin-1 suppresses the S-palmitoylation of each target protein. We will ectopically express Flag-tagged wild-type vs. mutant RIPK2 (with impaired interaction with Ran) in HEK293T/RIPK2-/- cells, and measure the S-palmitoylation levels of Ran. We will repeat the procedure for importin β1 and exportin-1.

We will also determine whether RIPK2 regulates the nucleocytoplasmic transport of certain oncoproteins and tumor suppressor proteins important for PCa progression. We will also have quantitative proteomic comparison of the cytoplasmic and nuclear fractions of PCa cells with vs.

without RIPK2-KO. We will use the NE-PER Nuclear and Cytoplasmic Extraction Reagent (Thermo) to separate cyto-plasmic from nuclear fractions of LNCaP, 22Rv1, DU145, and PC3 cells with vs. without RIPK2 knockout. We will perform TMT16plex-based multiplexed quantitative pro-teomics to identify proteins whose abundance is differen-tially regulated in the cytoplasmic vs. nuclear fractions as we previously described. Briefly, for each cell line, we will digest an equal amount of proteins into peptides with trypsin using filter-aided sample preparation (FASP) and label the resulting tryptic peptides using a set of TMT16plex reagents (2 conditions×2 fractions×4 biological replicates). We will mix TMT16plex-labeled peptides into one sample, desalt the mixture with C18 spin columns (Thermo), and fractionate the peptide mixture into 24 fractions by high-pH reversed-phase liquid chromatography (RPLC) using an Ultimate 3000 XRS system (Thermo). We will analyze each peptide fraction using an EASY-nLC 1200 UPLC system connected to an Orbitrap Fusion Lumos Tribrid mass spectrometer (Thermo). For higher quantification accuracy, we will apply the synchronous precursor selection-triple mass spectrom-etry (SPS-SP3) method. Notably, the SPS-MS3 method largely eliminates the ratio compression issue caused by precursor ion interference and thus significantly improves the quantification accuracy. We will analyze the acquired RAW files with Proteome Discoverer (v2.2) and perform statistical analysis using Perseus (v1.6.6.0) and R (v3.5.0). For protein identification, we will apply the standard cutoff of 1% to filter peptide-spectrum matches (PSMs), peptide identifications, and protein identifications. For protein quan-tification, we will apply the cutoffs of q<0.05 and log$_2$-transformed fold change >0.5 in absolute value to identify differentially expressed proteins.

We will also validate select proteins whose nucleocyto-plasmic distribution is regulated by RIPK2. From the dif-ferentially distributed proteins identified in SA2.2a, we will select three known PCa oncoproteins and three known tumor suppressor proteins for which high-quality antibodies are available. We will confirm their differential nucleocytoplas-mic distributions in cells with RIPK2-KO vs. ctrl-KO by IB analysis using target-specific antibodies. We will also deter-mine whether their nucleocytoplasmic transport in parental cells can be modulated by RIPK2 inhibitors G/P/C.

Figure 8:
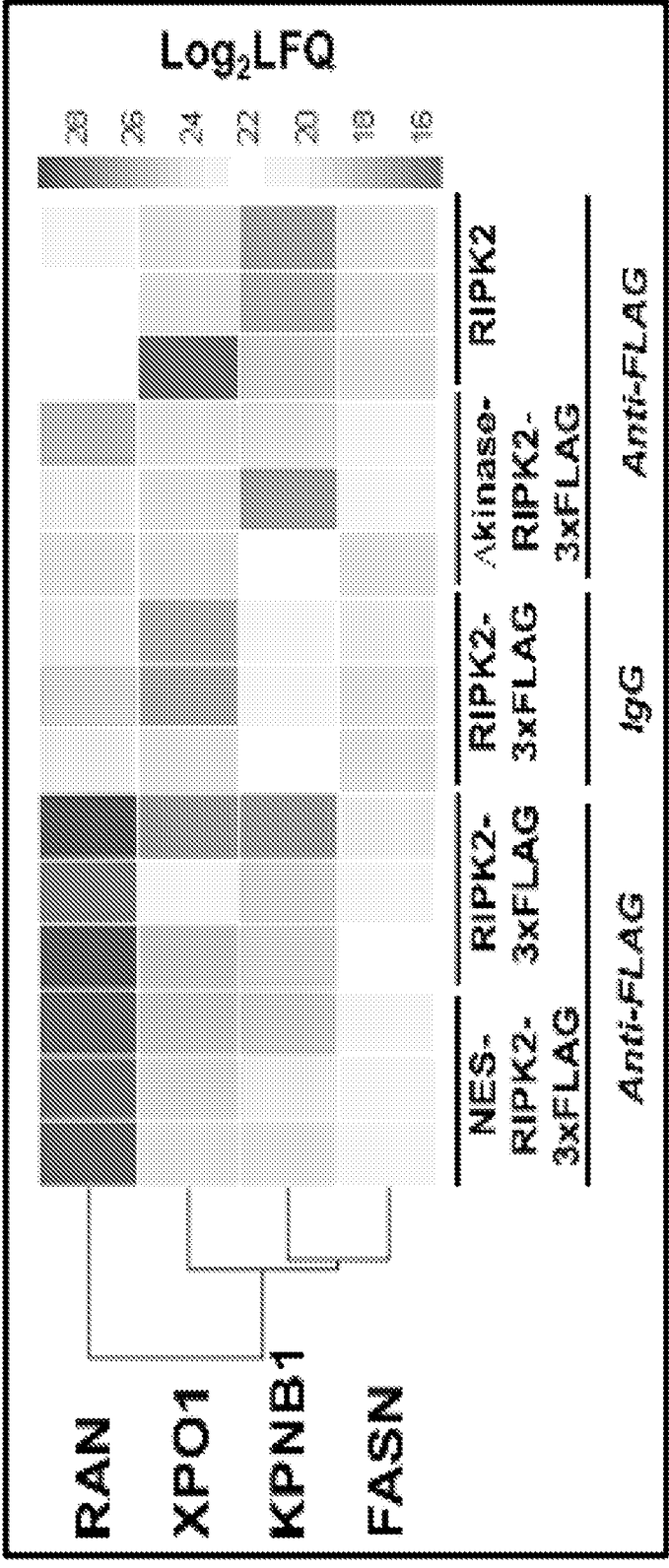
FIG. 8 shows the heatmap of four proteins associated with the kinase domain of RIPK2. NES: nuclear export signal; Δkinase: deletion of the kinase domain. LFQ: label-free quantification.

We will also determine whether Ran S-palmitoylation is important for RIPK2-induced PCa progression The Ran GTPase is a small 25 kDa protein that is important for transporting proteins into and out of the cell nucleus. Our RIPK2 interactome study suggested that Ran is an abundant protein in the RIPK2 complex (FIG. 8). Thus, in this task, we will focus on studying Ran instead of importin β1 or exportin-1.

We will also identify Ran cysteine residue(s) whose S-palmitoylation is enhanced by RIPK2. Ran only has three cysteine residues (Cys85, Cys112, and Cys120) and it was found to be at least S-palmitoylated on Cys112 and Cys120. We will generate a FLAG-tagged RAN construct and mutate the three cysteine residues (C85A, C112A, C120A, C85A-C112A, C85A-C120A, C112A-C120A, and C85A-C112A-C120A).

Using these constructs, we will determine the site(s) on which the S-palmitoylation level is regulated by RIPK2. We will co-express RIPK2 and each RAN construct into HEK293T cells, followed by analyzing the S-palmitoylation level changes using LB-ABE and MLCC as described in SA2.1a. We will also determine whether RIPK2 inhibition by G/P/C suppresses the S-palmitoylation of Ran on the identified site(s).

We will also determine whether RIPK2-enhanced Ran S-palmitoylation modulates the nucleocytoplasmic transport of the oncoproteins and tumor suppressor proteins validated in SA2.2b. We will co-express RIPK2 and wild-type vs. S-palmitoylation-deficient mutant Ran into HEK293T cells. We will separate cytoplasmic from nuclear fractions and probe the abundance of the oncoproteins and tumor suppressor proteins as described herein.

We will also determine whether Ran S-palmitoylation is important for RIPK2-driven PCa progression in vitro. We will stably co-express RIPK2 and wild-type vs. S-palmitoylation-deficient mutant Ran in LNCaP, VCaP, 22Rv1, DU145, and PC3 cells. We will perform 3D invasion, clonogenic assay, soft agar assay, and enzalutamide resistance assay, followed by statistical analysis, as described herein.

We will also determine whether Ran S-palmitoylation is important for RIPK2-driven PCa progression in vivo. We will use PC3 and 22Rv1 single-cell clones with stable co-expression of RIPK2 and RAN (wild-type vs. S-palmitoylation-deficient). We will perform in vivo tumor growth and metastasis assays as well as data analysis and IHC analysis as described herein. For enzalutamide resistance assay, depending on the results herein, we will use LNCaP and/or VCaP cells with stable co-expression of RIPK2 and RAN (wild-type vs. S-palmitoylation-deficient).

We expect that RIPK2 enhances FASN-dependent S-palmitoylation of Ran, importin β1 and exportin-1 in different PCa cell lines and that RIPK2 directly binds to FASN and Ran. We anticipate quantifying >8,000 proteins in the TMT16plex analyses; among these, >50 proteins will be identified as differentially nucleocytoplasmic transported. We expect that Ran S-palmitoylation is important for RIPK2-driven mCRPC development in vitro and in vivo.

If RIPK2 does not regulate the S-palmitoylation of Ran, importin β1 or exportin-1, we will perform a global S-palmitoyl-proteomics analysis to identify proteins whose S-palmitoylation is regulated by RIPK2 and select PCa-related candidates for further analysis. If no candidate oncoproteins or tumor suppressors could be identified or validated, we will perform DAVID and Ingenuity Pathway Analysis to identify significantly enriched protein groups that are involved in PCa progression, from which we will select PCa-related candidates for investigation. If Ran S-palmitoylation is not important for RIPK2-induced mCRPC development, we will study the roles of S-palmitoylated importin β1 or exportin-1.

Example 4

Determine Whether RIPK2 Drives mCRPC Development by Modulating the Subunit Abundance or Assembly of Certain Protein Complexes that are Important for PCa Progression While not wishing to be bound by any particular theory, RIPK2 regulates the subunit abundance or assembly of certain PCa-related protein complexes, which in turn promote PCa metastasis and enzalutamide resistance. Rationale: Protein complexes act as highly specialized molecular machinery and carry out essentially all major processes in a cell. The abnormal expression and/or activation of certain protein complexes may lead to the pathogenesis and progression of many diseases. Our study showed that RIPK2-KO in PC3 cells decreased the subunit abundance of the c-Myc:Max complex and the multiprotein ATP synthase, two protein complexes important for cancer progression.

This suggests that RIPK2 may promote mCRPC development at least partly by modulating certain PCa-related protein complexes. We recently developed a novel method for global analysis of protein complexes to identify deregulated protein complexes in PCa tissue specimens. This method is partly built upon a Nature Biotechnology paper showing that, when coupled with protein co-regulation analysis, TMT-SPS-MS3 quantification permits systems-wide analysis of protein-protein interactions with high accuracy. Here, we will apply our method to identify cellular protein complexes regulated by RIPK2, followed by validation and functional studies to determine whether key protein complexes of interest mediate RIPK2-driven PCa metastasis and enzalutamide resistance. Significance: Global analysis at the protein complex level provides a new layer of information, which can hardly be captured by genomic, transcriptomic, or proteomic analysis. The study may provide novel protein-complex biomarkers reporting RIPK2 activity in PCa cells and new drug targets. Innovation: Our method for proteome-wide analysis of protein complexes is novel.

We will also identify protein complexes whose subunit abundance or assembly is regulated by RIPK2 SA3.1a: Quantitative proteomic comparison of PCa cells with vs. without RIPK2 KO. We have already generated stable single-cell clones for LNCaP, 22Rv1, DU145, and PC3 cells with vs. without RIPK2 KO. We will apply TMT16plex-based multiplexed quantitative proteomics to compare the eight cell clones, essentially as we described3. We will culture these cell clones in regular media, extract proteins, digest an equal amount of proteins into tryptic peptides using FASP, and label tryptic peptides using a set of TMT16plex reagents (4 lines×ctrl/RIPK2-KO×2 biological replicates). We will combine differentially TMT-labeled samples into one mixture, desalt peptides with C18 spin columns, fractionate peptides by high-pH RPLC into 24 fractions, analyze each fraction by LC-SPS-MS3 using an EASY-nLC 1200 coupled to an Orbitrap Fusion Lumos, and use Proteome Discoverer (v2.2) to perform database searching for protein identification and quantification.

We will also perform expression analysis to identify differentially expressed protein complexes. The CORUM (v3.0) database is a high-quality collection of 4,274 experimentally verified mammalian protein complexes, of which 67% are human protein complexes. Notably, the CORUM database only comprises protein complexes that have been individually isolated and characterized. Therefore, it is generally considered as a gold-standard database for mammalian protein complexes. Essentially as we described3, we will use the R (V3.5.0) to map proteins quantified across all samples into individual CORUM protein complexes. For statistical analysis, we will only include non-redundant protein complexes containing ≥2 quantified subunits and with ≥50% subunit coverage. We will calculate the mean log 2-ratios of all proteins in each qualified CORUM complex, compare the differences between the ctrl-KO and RIPK2-KO groups by two-tailed Student's t-test, and apply the Storey method to correct the p values for multiple testing. We will accept the CORUM complexes with q values of <0.05 and the mean difference of >0.5 in absolute value as differentially expressed complexes.

We will use Perseus (v1.6.6.0) to perform Fisher exact test of the differentially expressed complexes, followed by applying the cutoffs of q<0.05 and enrichment factor >2 to identify significantly enriched gene ontology (GO) terms.

We will also use co-regulation analysis to identify differentially assembled protein complexes. Essentially as we described3, we will only include non-redundant CORUM protein complexes containing ≥2 quantified subunits and with ≥50% protein-protein interaction (PPI) coverage. We will apply R (v3.5.0) to conduct differential co-regulation analysis3. Briefly, we will use the Spearman's method to assess the correlation of proteins within each CORUM complex, followed by performing the Fisher z-transformation to stabilize the variance of sample correlation coefficients in each condition. To avoid obtaining infinite z scores, we will replace all Spearman's Rho values of 0.99 through 1 by 0.99 and those of −1 through −0.99 by −0.99. For each CORUM complex, to determine whether the difference of the mean z scores between the two conditions (ctrl-KO vs. RIPK2-KO) is statistically significant, we will perform the following steps: 1) 8 out of the 16 samples will be randomly sampled twice and used as condition A and condition B, respectively; 2) for each condition, Spearman's Rho values and z scores will be computed; 3) the mean z score difference between conditions A and B will be calculated; 4) the steps 1-3 will be repeated for 10,000 times, and a null hypothesis distribution of the mean z score differences will be generated; 5) the significance of each observed mean z score difference will be computed using the null hypothesis distribution; 6) the p values will be adjusted by the Storey method for multiple comparison3. We will apply the cutoffs of q<0.05 and mean z score differences of >0.7 in absolute value to identify differentially assembled protein complexes. We will use Perseus (v1.6.6.0) to perform Fisher exact test, followed by applying the cutoffs of q<0.05 and enrichment factor >2 to identify significantly enriched GO terms.

We will also validate the modulation of select candidate protein complexes of interest by RIPK2 SA3.2a: Select candidate protein complexes of interest. From the list of differentially expressed or assembled protein complexes, we will select certain protein complexes based on the criteria that 1) at least one key subunit is known to be functionally important for PCa progression, 2) only select protein complexes consisting of two or three subunits to simplify validation, 3) only select protein complexes that are positively regulated by RIPK2 to simplify functional studies, and 4) exclude the c-Myc:Max complex for further analysis because c-Myc is studied in Aim 1. In descending order, we will rank eligible protein complexes based on a) the −log 10-transformed q values, b) the fold changes, and c) the number of citations for a key subunit. We will select the top three candidates from each list for validation.

We will also validate select protein complexes whose subunit expression is regulated by RIPK2. We will culture stable LNCaP, 22Rv1, DU145, and PC3 cell clones under four conditions: ctrl-KO, RIPK2-KO, ctrl-OE, and RIPK2-OE (n=3). We will perform IB analysis to compare the relative abundance of each subunit in whole-cell lysates, using subunit protein-specific antibodies. Moreover, we will IP the protein complexes from the eight cell-conditions (n=3) using subunit protein-specific antibodies, followed by measuring the relative abundance of each subunit by IB analysis. Negative controls will be blank protein A/G PLUS Agarose. For the validated complexes, we will apply the same procedure to determine whether their abundance in parental LNCaP, VCaP, 22Rv1, MR49F, C4-2R, DU145, and PC3 cells are regulated by RIPK2 inhibitors G/P/C. SA3.2c: Validate select protein complexes whose subunit assembly is regulated by RIPK2. Firstly, we will perform in-situ PLA analysis of LNCaP, 22Rv1, DU145, and PC3 cells under four conditions: ctrl-KO, RIPK2-KO, ctrl-OE, and RIPK2-OE (n=3). If a candidate complex consists of two subunits, we will use the Duolink In Situ Red Starter Kit Mouse/Rabbit (Sigma) as described in FIG. 5C. If a candidate protein complex consists of three subunits, we will use the Duolink PLA Multicolor Probemaker Kit (Sigma) according to the manufacturer's protocol. Briefly, we will prepare three pairs of custom PLA oligo-conjugated primary antibodies (red, green, and orange). After fixing cells and blocking samples, we will incubate samples sequentially with 1) oligo-conjugated primary antibodies, 2) ligation solution and 3) amplification solution. We will visualize nuclei using DAPI and then examine PLA signals under an All-in-One Fluorescence Microscope BZ-X710. We will include negative controls by omitting one of the three oligo-conjugated primary antibodies. For quantitative comparison, we will count red dots and blue nuclei in five random fields, calculate the red/blue ratios, and compare the ratios in the experimental versus control conditions using two-sided Student's t-test at a significance level of 5%. Secondly, we will IP the protein complexes from the eight cell-conditions (n=3) using subunit protein-specific antibodies, followed by measuring the relative abundance of each subunit by D3 analysis. Negative controls will be blank protein A/G Plus agarose beads. For the validated protein complexes, we will apply the same procedure to determine whether their levels in parental LNCaP, VCaP, 22Rv1, MR49F, C4-2R, DU145, and PC3 cells are regulated by RIPK2 inhibitors G/P/C.

We will also determine whether protein complexes of interest mediate RIPK2-driven PCa progression. From the validated protein complexes, we will select two protein complexes whose subunits are most related to PCa progression, according to the number of PubMed entries, for in vitro analysis. Based on the in vitro analysis result, we will choose one protein complex for in vivo assays.

We will also determine whether protein complexes of interest mediate RIPK2-driven PCa progression in vitro. We will identify the interaction interface and hot-spot residues as described in Task 1.1. We will determine whether stably co-expressing the wild-type but not mutant protein complex subunits will rescue impaired 3D invasion, colony formation, and enzalutamide resistance resulting from RIPK2 KO or inhibition. We will determine whether shRNA knockdown of the protein complex subunits, either individually or in combination, in RIPK2-overexpressing PCa cells will significantly impair RIPK2-enhanced 3D invasion, colony formation, and enzalutamide resistance. All the cell assays will be performed as described in herein.

We will also determine whether the protein complex of interest mediates RIPK2-driven PCa progression in vivo. Based on our results, we will choose one protein complex for in vivo analyses. We will use the cell clones qualified herein to analyze PCa tumor growth, metastasis, and enzalutamide resistance as described herein.

We anticipate quantifying >8,000 proteins across all the 16 cell pellet samples and discover >20 differentially expressed/assembled protein complexes using our new complexome profiling method. We anticipate validating the regulation of at least four out of six select candidate protein complexes by RIPK2. We anticipate to successfully map the interaction interface and hot-spot residues for two complexes. We will identify one protein complex mediating RIPK2-driven PCa progression in vitro and in vivo.

If we cannot identify any significantly changed CORUM protein complexes across the four PCa cell lines, we will use the Human Protein Complex Map (hu.MAP) database to replace the CORUM database and perform differential expression and co-regulation analyses. Notably, the hu.MAP database was developed by integrating >9,000 mass spectrometry experiments and contains >4,600 human protein complexes. Alternatively, we will study the roles of the multiprotein ATP synthase, because our preliminary data suggested that multiple subunits within the complex were significantly downregulated by RIPK2-KO in PC3 cells. In addition, it is possible that some proteins units in the tested protein complexes do not have high-quality antibodies. In this case, we will apply targeted mass spectrometry methods, such as triggered by offset, multiplexed, accurate mass, high resolution, and absolute quantification (TOMAHAQ) and parallel reaction monitoring (PRM), to quantify the protein abundance.

Example 5

There is progressively increased expression of RIPK2 in PCa as it become more aggressive: low GG<high GG<mCRPC<neuroendocrine PC. The end result of RIPK2 inhibition in advanced PCa is inhibition of MYC signaling. The biological phenotype is a reduction of invasive capacity with a minimal effect of slowing cancer growth. There is similar co-amplification of RIPK2 and MYC in breast cancer. Through pilot studies on plasma samples of patients with CRPC, we identify patients with RIPK2 and MYC co-amplification by analysis of plasma extracellular vesicles.

Ponatinib is an FDA-approved anticancer agent that inhibits RIPK2. Ponatinib (Iclusig, AP24534-ARIAD pharmaceuticals) produced abl and src-family kinase inhibitor approved for use of the treatment of chronic myeloid leukemia (CML) and Philadelphia chromosome-positive (Ph+) acute lymphoblastic leukemia (ALL). It is approved for use in T315I mutated forms of Ph+ ALL. Arterial occlusive adverse events of interest to this agent include: cardiac vascular events (21%), peripheral vascular (12%) and cerebrovascular (9%). Venous thromboembolic events occurred in 6% of patients. Common adverse events include:

| | |
|---|---|
| hypertension | 69% |
| rash | 63% |
| abdominal pain | 48% |
| fatigue | 47% |
| headache | 43% |
| arterial ischemia | 42% |
| dry skin | 42% |
| constipation | 41% |
| arthralgia | 32% |
| nausea | 28% |
| pyrexia | 26% |
| peripheral neuropathy | 24% |
| myalgia | 24% |
| pain in extremity | 23% |
| back pain | 21% |
| diarrhea | 20% |

As such, while not wishing to be bound by any particular theory, we believe that in PCa and Breast Ca where both RIPK2 and MYC are overexpressed or amplified, inhibition of RIPK2 results in inhibition of metastatic potential that will manifest as delayed radiographic progression free survival (rPFS).

Study design: Single arm, open label study of ponatinib monotherapy in biomarker (+) patients. Ponatanib will be provided ARIAD pharmaceuticals, now part of Takeda Oncology.

We believe that ponatinib will result in delayed radiographic progression in PCa and/or Breast Ca. Impact on angiogenic signals therapy may obscure PSA benefit.

Eligibility
Inclusion-Prostate
Progression by PSA±radiograph
Must have had at least one but no more than 2 prior contemporary ARSI therapies including abiraterone, enzalutamide, darolutamide, or apalutamide. Prior bicalutamide, flutamide, or nilutamide will not count.
Exclusion-Prostate
Small cell prostate cancer
Radiographic progression without a rising serum PSA
Prior use of chemotherapy for CRPC
Objectives
Primary Objectives
Measure the % of the study population (RIPK2/MYC amplified/gained) without radiographic progression at 4 months on single agent ponatinib
Secondary Objectives
Measure PFS of ponatinib after previous ARSI therapy
Describe the adverse events associated with ponatinib in prostate and breast cancers
Measure the PSA response rates (>50% decrease) of ponatinib
Statistical Considerations
Assumptions
For patients who decline chemotherapy, use an alternative ARSI would represent a standard of care in CRPC. Radiographic PFS on a second ARSI is 3.7 mo (de Witt R, N Eng J Med 2019)
If ponatinib does not influence outcome, radiographic progression should occur by 4 months in more 50% of the population from the point of starting the study

Example 6

Generation of Mutant and Fusion cDNA

Primer sequences for molecular cloning were listed in Data S7. Site-directed mutagenesis was conducted with the QuickChange II XL Site-Directed Mutagenesis Kit (Agilent, #200521). RIPK2m4 was generated by synonymous substitution of 648 A→T, 651 T→A, 654 C→A, and 657 A→C. The following fusion cDNAs were generated by PCR and cloned into the pLenti-puro vector: 3×FLAG-tag was fused to the C-terminus of target genes; NLS (CCAAAAAAGAAAAGAAAAGTT) (SEQ ID NO:1) and NES (CTACCGCCGCTGGAAAGACTGACTCTG) (SEQ ID NO:2) to the N-terminus of RIPK2m4; 6×His-tag to the C-terminus of MKK7. The RIPK2m4 sequence was cloned into the pLJM-eGFP vector to form RIPK2m4-eGFP. The MKK7 sequence was cloned into the mCherry2-N1 vector to form MKK7-mCherry. All plasmids were validated by sequencing (Laragen).

RNA Extraction and Quantitative Real-Time Polymerase Chain Reaction (RT-PCR)

Total RNA was extracted from cells using the TRIZOL (Invitrogen). Messenger RNA was converted to the first-strand cDNA using iScript cDNA synthesis kit (Bio-Rad), followed by RT-PCR reaction using SYBR Green PCR Master Kit in QuantStudio 5 Systems (Applied Biosystems). Gene expression was normalized to GAPDH using the comparative CT method.

Cell Lines

PC3, DU145, 22Rv1, LNCaP, RWPE-1, RWPE-2, and HEK293T cells were obtained from the American Type Culture Collection (ATCC). The cell lines were authenticated using the Promega PowerPlex 16 system DNA typing (Laragen). Unless otherwise specified, the cells were cultured in the media as follows. PC3, DU145, and HEK293T cells were cultured in DMEM, while 22Rv1 and LNCaP cells were cultured in RPMI-1640, supplemented with 10% fetal bovine serum (FBS), 2 mM L-glutamine, 100 units/mL penicillin and 100 µg/mL streptomycin. RWPE1 and RWPE2 cells were cultured in Keratinocyte Serum-Free Medium supplemented with 50 µg/mL bovine pituitary extract and 5 ng/mL human recombinant epidermal growth factor. All cells were cultured at 37° C. in a 95% air, 5% CO2 humidified atmosphere. *Mycoplasma* contamination was routinely monitored using the MycoAlert PLUS *Mycoplasma* Detection Kit (Lonza, #LT07-118).

Gene Knockout by CRISPR/Cas9 sgRNAs targeting human RIPK2 (#2 and #3), MAP2K7 (#1 and #2), and PRKDC (#1 and #2) genes were designed using the sgRNA designer (Broad Institute). Their sequences and targeting domains are shown in Data S8. All guide RNAs were cloned into LentiGuide-Puro (Addgene) according to the Zhang laboratory protocol, followed by sequencing validation (Laragen). Transfer (LentiGuide-Puro or LentiCas9-Blast), packing (psPAX2), and envelope (pMD2.G) plasmids were co-transfected into HEK293T cells to produce lentivirus containing sgRNAs and Cas9. After 7 h, cell supernatants were filtered with 0.45 µm filters and stored at −80° C. for future use. To generate stable cell lines with gene knockout, cells were cultured in 6-well plates for 24 h to reach ~50% confluency, followed by infection with lentivirus of Cas9 and sgRNA supplemented with 10 µg/mL polybrene. After 72 h, medium was replaced by fresh medium supplemented with 10% FBS, 2 mM L-glutamine, 100 units/mL penicillin, 100 µg/mL streptomycin, 10 µg/mL blasticidin and 1 µg/mL puromycin. The selective medium was replaced every other day.

Isolation of Stable Single Cell Clones

Single-cell clones were isolated by seeding individual cells in 96-well plates (5 cells/mL, 100 µL per well). About 10 days later, monoclonal cells were marked, monitored for growth, and sub-cultured.

Transient Transfection

When cells grew to a confluency of ~50%, a specified amount of plasmid was transfected into cells using Turbofectin 8.0 (Origene) by following the manufacturer's instruction. Briefly, plasmids and Turbofectin 8.0 were mixed at a ratio of 1:3 (w/v) to Opti-MEM, followed by incubation at room temperature for 15 min. The mixture was then added dropwise to cultured cells and incubated for 48 h at 37° C. In the RIPK2 and c-Myc co-transfection experiments, 0.5 µg per plasmid was used. In some cell line experiments, cells were co-transfected with the c-Myc or MKK7 plasmid to enable the immunoblotting detection of pS62-c-Myc or p-MKK-S271.

Cell Proliferation Assay

The growth curve assay was performed using the Cell Counting Kit-8 (CCK-8) (Sigma-Aldrich, #96992) according to the manufacturer's instruction. Briefly, 100 µL of cells (2,500 cells/mL for PC3 and DU145 and 10,000 cells/mL for 22Rv1) were plated in 96-well plates at day 0. A mixture of 10 µL CCK-8 reagent and 10 µL Dulbecco's phosphate-buffered saline (DPBS) was added into each well at indicated time points. Plates were incubated in a humidified incubator at 37° C. for 2 h, followed by measuring the absorbance at 450 nm using a microplate reader (800 TS, BioTek).

Migration Assay

Migration assay was performed. The outside membrane of Transwell inserts (8 µm pore size) was coated with 50 µL of 15 µg/mL Collagen Type I. A total of $5 \times 10^4$ control or RIPK2-KO PC3 cells in 200 µL serum-free medium were seeded into the upper chamber, followed by adding 600 µL 10% FBS-containing medium to the lower chamber. After incubation at 37° C. for 6 h, cells were fixed by 4% paraformaldehyde and stained by 0.12 mg/mL crystal violet solution for 15 min. Cells on the inside membrane of Boyden chambers were removed by cotton swabs. Migrated cells on the outside membrane were rinsed with deionized water for three times and imaged under an All-in-one Keyence microscope. The total area (µm2) of migrated cells was automatically calculated using the Keyence image analyzer.

Matrigel Invasion Assay

Invasion assay was conducted. The inside membrane of Transwell inserts (8 µm pore size) was coated with 50 µL Matrigel matrix (1:50 diluted). For each sample, 200 µL ($1 \times 10^6$ cells/mL) of control or RIPK2-KO PC3, DU145, or 22Rv1 cells suspended in serum-free medium were seeded in the upper chamber. 600 µL of 10% FBS-containing medium was added to the lower chamber. After incubation at 37° C. for 24 h, cells were fixed, stained, cleaned, imaged, and quantified as described in the migration assay. 3D Spheroid Invasion Assay Spheroid invasion assay was performed. 4,000 PC3 cells in 200 µL DMEM medium supplemented with 10% FBS, 2 mM L-glutamine, 100 units/mL penicillin and 100 µg/mL streptomycin were plated in Ultra-Low attachment U-bottom 96-well plates (Corning, #4515) and cultured for four days to form tumor spheroids. 100 µL Matrigel was gently dispensed to each well containing a tumor spheroid and incubated at 37° C. for 1 h. For the comparison of control and RIPK2-KO PC3 spheroids, 100 µL DMEM medium was added to each well. For the drug treatment experiment, 100 µL DMEM medium supplemented with DMSO, 10 µM GSK583, or 5 µM Ponatinib was added. Images at indicated time points were taken by an All-in-one Keyence microscope and analyzed by the INSIDIA macro in the environment of Fiji, an image processing package based on ImageJ. Relative perimeter, which reflects the complexity of the invading edge, was recently shown as a parameter that displays a similar trend to invasion index A (the percentage of edge sub-area over the entire cell-covered area) and thus can provide a quick and easy analysis of spheroid invasion. Hence, it was used to quantify invasion.

Clonogenic Assay (Anchorage-Dependent Colony Formation Assay)

Two milliliters of PC3 (250/mL), DU145 (250/mL), or 22Rv1 (1,000/mL) cells were seeded in 6-well plates and cultured in 10% FBS-containing media, which were replaced every 2-3 days. After 10-14 days, cells were fixed in 4% paraformaldehyde for 15 min and rinsed with DPBS for three times. Cells were stained with 120 µg/mL crystal violet solution. Cell colonies were quantified under an All-in-one microscope (Keyence) as described in the migration assay.

Soft Agar Assay (Anchorage-independent Colony Formation Assay)

Soft agar assay was performed essentially as described (Borowicz et al., 2014). Briefly, 1.5 mL of 0.5% Nobel agar solution was plated in each well of 6-well plates as the bottom layer. 1.5 mL of $6.67 \times 10^3$/mL (for PC3 and DU145) or $1.33 \times 10^4$/mL (for 22Rv1) cells in 0.3% noble agar solution were plated in 6-well plates as the top layer. Cells were cultured in DMEM supplemented with 10% FBS, 2 mM L-glutamine, 100 units/mL penicillin and 100 µg/mL streptomycin. The medium was replaced every 2-3 days. After 2-3 weeks, cell colonies were stained with 0.1% crystal violet solution for 20 minutes and washed with deionized water for five times. Cell colonies were quantified under an All-in-one microscope (Keyence) as described in the migration assay.

Animal Studies

All experimental protocols and procedures were approved by the Institutional Animal Care and Use Committee at Cedars-Sinai Medical Center and the Animal Care and Use Review Office at Department of Defense. All relevant ethical regulations, standards, and norms were rigorously adhered to.

Subcutaneous xenograft model: For In vivo tumor growth assays, control or RIPK2-KO 22Rv1 cells were adjusted to $1.5 \times 10^7$ cells/mL in DPBS, followed by mixing with Matrigel at a 1:1 ratio (v/v). For each male SCID/Beige mouse (7-week-old; Charles River), 100 μL mixture was subcutaneously injected into both flanks. Tumor length and width were measured with a caliper for three times each week, and tumor volumes were calculated using the formula of (length×width2)/2. At the endpoint, mice were euthanized and tumor xenografts were collected and weighted with a scale.

Experimental metastasis model: For In vivo metastasis assays, pBMN (CMV-copGFP-Luc2-Puro) (Addgene) was stably transfected into control and RIPK2-KO 22Rv1 cells. Two weeks later, luciferase-expressing cells were sorted with a FACSAria III (BD Biosciences) using the same gate for GFP. Control and RIPK2-KO 22Rv1 cells expressing similar levels of luciferase were selected and expanded. To each male SCID/Beige mouse (7-week-old; Charles River), 100 μL of $1 \times 10^7$ cells/mL in DPBS was intracardially injected into the left cardiac ventricle. Each week, 150 μL of 30 mg/mL D-luciferin was intraperitoneally injected into each mouse, followed by measuring tumor metastasis with an IVIS Spectrum In Vivo Imaging System (PerkinElmer). Luciferase activity was quantified by the Living Image software (Caliper Life Sciences, v4.3.1).

Established metastasis model: For drug treatment, to each male SCID/Beige mouse (8-week-old; Charles River), 100 μL of $2.5 \times 10^6$ cells/mL in DPBS was intracardially injected. Nine days later, mice were randomized into two groups (DMSO vs. GSK583) or three groups (DMSO vs. low-dose Ponatinib vs. high-dose Ponatinib). Two more mice were assigned to drug treatment groups in preparation for possible drug toxicity deaths, compared with the control group. Mice were daily administered by oral gavage (po qd) with a drug or vehicle control for 28 days. GSK583 was administered at 10 mg/kg po qd. For the low-dose Ponatinib group, mice were treated daily with 6 mg/kg Ponatinib, a dose that is equivalent to 30 mg Ponatinib for a 60-kg human adult. For the high-dose Ponatinib group, mice were treated with 30 mg/kg Ponatinib po qd for 10 days. Due to adverse effects, the Ponatinib dose was then reduced from 30 to 15 mg/kg. Metastases were visualized by bioluminescence imaging every week as described above. At the end of the experiments, mice were sacrificed by standard necropsy, and tumors were harvested and subjected to histopathology analyses.

Hematoxylin and Eosin (H&E) Staining and Immunohistochemistry (IHC)

H&E and IHC were carried out by the Cedars-Sinai Biobank & Translational Pathology core by following standardized protocols. For IHC staining of tissue microarrays, the anti-RIPK2 antibody (Sigma Aldrich #HPA015273) was used at 1:100 dilution. Stained slides were digitized using Aperio AT Turbo (Leica Biosystems). Cancer areas and normal glands were annotated by an expert pathologist (X. Y.) in the H&E images. The annotations were digitally transferred onto the IHC images, which were exported for image analysis in the Leica Tissue IA software package (Leica Biosystems). Protein expression was quantified by the mean 3,3'-diaminobenzidine (DAB) staining intensity of pixels in the annotated normal and tumor areas. DAB staining was automatically deconvolved from hematoxylin by the software.

c-Myc Luciferase Assay

The c-Myc activity was assessed using the Myc Reporter kit (BPS Biosciences) and the Dual-Luciferase Reporter System (Promega) according to the manufacturers' instructions. Briefly, 100 μL ($1.5 \times 10^5$ cells/mL) control and RIPK2-KO PC3 cells were seeded into 96-well plates. After overnight incubation, when cells reached ~50% confluency, 1 μL of Reporter A (60 ng/μL) in the Myc Reporter kit was transfected into cells using Turbofectin 8.0. After 48 h, cells were lysed in 25 μL Passive Lysis Buffer (provided in the Dual-Luciferase Reporter kit). 20 μL of cell lysate was transferred to 96-well plates and placed in a 96-well microplate luminometer (GloMax-Multi, Promega). 100 μL Luciferase Assay Reagent II and 100 μL Stop & Glo Reagent (both provided in the Dual-Luciferase Reporter kit) were sequentially injected, and firefly and Renilla luciferase activities were automatically measured. c-Myc activities were determined by the ratios of firefly to Renilla luciferase activities.

Label-Free Proteomics

Label-free proteomics was performed. Briefly, after cell lysis, 60 μg protein per sample was digested into tryptic peptides using the filter-aid sample preparation (FASP) method. About 1 μg peptides in 10 μL solution were separated on a 50-cm EASY-Spray column using a 200-min LC gradient at the flow rate of 150 nL/min. Separated peptides were analyzed with an LTQ Orbitrap Elite (Thermo Scientific) in a data-dependent manner. The acquired MS data (24 RAW files) were searched against the Uniprot_Human database (released on Jan. 22, 2016, containing 20,985 sequences) using the Andromeda algorithm (Cox et al., 2011) in the MaxQuant (v1.5.5.1) environment (Cox and Mann, 2008). A stringent 1% FDR was used to filter the identifications of peptide-spectrum matches, peptide, and protein groups. Note that in bottom-up proteomics analysis, different proteins identified by the same set of shared peptides cannot be distinguished, so they are collapsed into a "protein group" to minimize redundant identifications. The mass spectrometry proteomics data have been deposited to the ProteomeXchange Consortium (proteomecentral.proteomexchange.org) via the PRIDE partner repository with the database identifier PXD18890, where more detailed experimental information was included. Perseus (v1.6.6.0) (Tyanova et al., 2016) was applied to perform quality assessment and statistical analysis. Proteins identified from the reverse decoy and contaminating protein sequence databases as well as those with site-only identifications were removed. For statistical comparison, all LFQ intensity values were log 2-transformed, and only proteins with ≥3 valid values in each group were used. Unpaired two-tailed Welch's t-test followed by Benjamini-Hochberg adjustment was used to calculate p and q values, respectively. Protein groups meeting the criteria of p<0.05 and log 2-transformed fold change of >0.5 in absolute value were considered as significantly changed proteins for overlapping analysis. To compute the combined p and q values across the three comparisons (gRNA10_4 vs Ctrl, gRNA10-12 vs Ctrl, and gRNA10-16 vs Ctrl), Stouffer's method followed by Benjamini-Hochberg adjustment was applied.

Interactome Analysis by Immunoprecipitation-Mass Spectrometry (IP-MS)

Cells were cultured in 150-mm dishes until reaching the confluency of ~50%, and then transfected with 15 μg of indicated plasmids for 48 h. After cell lysis, 500 μL of 2 mg/mL protein solution was pre-cleared by incubating with 60 μL of 50% immobilized protein A/G Plus agarose bead slurry (Thermo Scientific, #20423) for 2 h at 4° C. The pre-cleared protein solution was incubated with 3 μg anti-FLAG antibody (Sigma Aldrich, #F1804) or IgG (Millipore, #12-371) overnight at 4° C. The next day, 60 μL of 50% immobilized protein A/G gel slurry was added to each sample, followed by incubation on a vertical shaker for 2 h at 4° C. After washing for five times, bound proteins were eluted with 50 μL of 2× Laemmli sample buffer containing 5% β-mercaptoethanol, by heating at 95° C. for 5 min. Eluted proteins were analyzed by gel-enhanced liquid chromatography-tandem mass spectrometry (GeLC-MS/MS). Briefly, eluted proteins were resolved by short-range SDS-PAGE, reduced, alkylated, and digested with trypsin (1:50, w/w) for 16 h in the gel. Tryptic peptides were analyzed using an EASY-nLC 1200 connected to an Orbitrap Fusion Lumos (Thermo Scientific) operated in a data-dependent manner. The acquired MS data (20 RAW files) were searched against the Uniprot_Human database (released on Mar. 30, 2018, containing 93,316 sequences) using MaxQuant (v1.5.5.1). The data have been deposited to the PRIDE with the database identifier PXD18870, where more detailed experimental information was provided. Perseus (v1.6.6.0) was applied to perform quality assessment and statistical analysis as described in the label-free proteomics analysis. Outlier samples were detected by unsupervised clustering and excluded from statistical analysis. For each comparison, only proteins with ≥3 valid values in at least one group were used. Missing data were imputed from normal distribution by Perseus, using the default values (width 0.3; down shift 1.8). The p and q values were computed as described above. Protein groups meeting the criteria of q<0.05 and log 2-transformed fold change of >2 were accepted as significantly enriched proteins. To identify protein candidates that bind to the kinase domain but no other regions of RIPK2, two criteria were applied. Firstly, proteins are significantly enriched in both experimental groups (i.e., G3 and G5) compared with the three control groups (i.e., G1, G2, and G4). Secondly, proteins are not significantly enriched in the control group G4 compared with the other control groups G1 and G2. The second criterion was used to exclude the identification of proteins that may bind to the non-kinase-domain regions of RIPK2, which are not important for RIPK2's regulation of c-Myc.

Phosphoproteomics

From regularly cultured control and RIPK2-KO PC3 cells (described in the label-free proteomics section), 1 mg protein was reduced, alkylated, and digested with trypsin in Amicon Ultra-4 centrifugal filter units (Millipore, #UFC803024) using the FASP method. To the resulting peptide solution, 1.5 mL acetonitrile, 7.5 mL of Incubation Buffer (60% acetonitrile, 3% trifluoroacetic acid), and 2 mg equilibrated TiO2 beads were sequentially added and mixed, followed by incubation for 60 min. TiO2 beads were washed with 1 mL of 60% acetonitrile, 3% trifluoroacetic acid, 50 mM citric acid three times (20 min per time) and 1 mL of 80% acetonitrile, 0.1% trifluoroacetic acid for 1 min once. Phosphopeptides were eluted with 100 μL of 50% acetonitrile, 14% ammonium hydroxide and then 100 μL of 80% acetonitrile, 5.6% ammonium hydroxide (5 min incubation per elution). Peptide solution resulting from the two elution steps was combined and dried down in a SpeedVac. Enriched phosphopeptides were analyzed using an EASY-nLC 1200 connected to an Orbitrap Fusion Lumos operated in a data-dependent manner. The acquired MS data (9 RAW files) were searched against the Uniprot_Human database (released on Jan. 22, 2016) using MaxQuant (v1.5.5.1).

Perseus (v1.6.6.0) was applied to perform quality assessment and statistical analysis, as described in the interactome analysis. Phosphosites meeting the criteria of FDR≤1% and localization probability of >0.75 were accepted as confident identifications. To compute relative phosphorylation level changes, relative phosphosite intensities were normalized against the relative abundance of corresponding proteins, which were quantified in the above-mentioned label-free proteomic analysis. To quantify kinase activity changes in each comparison (i.e., Ctrl vs. gRNA10-4 or Ctrl vs. gRNA10_12), the KSEA algorithm was employed. Briefly, a correctly formatted dataset containing phosphosites with P<0.05 were inputted into the KSEA App interface, where the PhosphoSitePlus plus NetworKIN dataset was selected. Only kinases with ≥5 substrate sites were selected for the quantification of kinase activities. For each kinase, the log 2(Ctrl/KO) ratios of all substrate sites were averaged to infer kinase activity changes.

Western Blot

Membranes were probed with antibodies against RIPK2 (1:1,000, Cell Signaling Technology #4142 or Santa Cruz Biotechnology #sc-166765), phospho-NF-κB p65 (Ser536) (1;1,000, Cell Signaling Technology, #3033), NF-κB p65 (1:1,000, Cell Signaling Technology, #8242), IκBa (1:1,000, Cell Signaling Technology, #4814), c-Myc (1:5,000, Abcam #ab32072), phospho-c-Myc (Ser62) (1:1,000, Cell Signaling Technology #13748S), ubiquitin (K48-linkage specific) (1:1,000, Cell Signaling Technology, #12805), FLAG (1:5, 000, Sigma #F1804), MKK7 (1:1,000, Cell Signaling Technology #4172S or 1:2,000, Santa Cruz Biotechnology #sc-25288), MKK7 (phospho-Ser271) (1:1,000, Aviva Systems Biology #OAAF05547), JNK (1:1,000, Cell Signaling Technology #9252S or 1:2,000 Santa Cruz Biotechnology sc-7345), JNK (phospho-T183/Y185) (1:1,000, Cell Signaling Technology #9251S), mCherry (1:1,000, Abcam #ab213511), GFP (1:1,000, Abcam #ab290), β-actin (1:5, 000, Sigma Aldrich #5441), or GAPDH (1:1,000, Cell Signaling Technology #3683). Signal was visualized with secondary HRP-conjugated antibodies (1:5,000, Cell Signaling Technology #7074S or #7076S) and chemiluminescent detection.

c-Myc Ubiquitination Assay

Control and RIPK2-KO PC3 Cells were cultured in 100-mm dishes until reaching the confluency of ~80%, and then treated with 10 μM MG132 for 4 hours before cell lysis. Immunoprecipitation was performed as described in the Interactome analysis section, except that an anti-c-Myc antibody (Abcam #ab32072) was used. Eluted proteins were probed by immunoblotting as indicated.

Immunofluorescence and Fluorescence Imaging

For immunofluorescence imaging of NES-RIPK2m4-3× FLAG or NLS-RIPK2m4-3×FLAG, 2 mL (1.25×10^5/mL) of HEK293T cells with RIPK2-KO were plated into 6-well plates and grown on poly-L-lysine pre-treated coverslips. Cells were transfected with NES-RIPK2m4-3×FLAG or NLS-RIPK2m4-3×FLAG (1.0 μg per plasmid) for 48 h. Cells were then fixed and permeabilized in methanol/acetone (1:1, v/v) for 20 min at −20° C., washed by PBS twice, and blocked in 2% BSA for 1 h at 37° C. The primary antibody against FLAG (1:500, Sigma Aldrich #F1804) was diluted in 2% BSA and incubated at 4° C. overnight.

Following 3×PBS washes, fluorochrome-conjugated secondary antibody (1:1,000, Cell Signaling Technology #4408) was diluted in 2% BSA and incubated with the samples for 1 h at 37° C. in the dark. After 3×PBS washes, the coverslips were transferred to slides mounted in Mounting Medium with DAPI (Millipore, #DU082040), and the cells were viewed under an All-in-one fluorescence microscope (BZ-X700, Keyence). For fluorescence colocalization imaging of RIPK2 and MKK7, 2 mL (1.25×105/mL) of HEK293T cells with the knockout of both RIPK2 and MKK7 genes were plated and grown as mentioned above. Cells were co-transfected with 1) mCherry and eGFP, 2) MKK7-mCherry and eGFP, 3) mCherry and RIPK2-eGFP, or 4) MKK7-mCherry and RIPK2-eGFP (0.5 µg per plasmid) for 48 h. Cells were fixed and visualized as described in the immunofluorescence imaging. For immunofluorescence colocalization imaging of MKK7 and c-Myc, 2 mL (1.25×105/mL) of HEK293T cells with RIPK2- and MKK7-double knockout were plated and grown as mentioned above. Cells were transfected with RIPK2m4, MYC, and MKK7-His plasmids (0.5 µg per plasmid) for 48 h, fixed, permeabilized, washed, and blocked as described above. The primary antibody against MKK7 (1:200, Santa Cruz, sc-25288) or c-Myc (1:200, Abcam, ab32072) was diluted in 2% BSA and incubated at 4° C. overnight. Cells were incubated with fluorochrome-conjugated secondary antibodies and visualized as described above.

Proximity Ligation Assay (PLA)

PLA was performed according to the manufacturer's instruction (Duolink, #DU092101, Sigma). Primary antibodies were diluted in Duolink antibody diluent as follows: rabbit anti-RIPK2 (Cell Signaling Technology, #4142) at 1:500, mouse anti-MKK7 (Santa Cruz Biotechnology, #sc-25288) at 1:100, and mouse anti-PRKDC (Santa Cruz Biotechnology, #sc-5282) at 1:100. Imaging was performed with an All-in-one fluorescence microscope (BZ-X700, Keyence) under TexasRed and DAPI filters. The numbers of PLA signals (shown in red) and cells (nuclei, shown in blue) from four to five random fields were quantified for each sample with Image J (v1.52p). For quantitative comparison, the numbers under control conditions are the sum of dots per cell detected using each of the two target-specific antibodies.

In Vitro Kinase Assay

For the analysis of RIPK2 phosphorylation of MKK7, kinase-dead MKK7 was cloned into a TAT-HA vector (a gift from Steven Dowdy at UCSD) at BamHI and EcoR1 sites. The 6×His-tagged recombinant protein was expressed in E. coli (BL21-DE3) and purified using Ni-NTA affinity chromatography and eluted using imidazole-based competition. 3×Flag-tagged RIPK2 was expressed in HeLa cells and immunoprecipitated on Protein A Agarose beads using an anti-Flag antibody. Kinase reaction was performed for 30 min using 0.5 µCi of [γ-32P]ATP per reaction, and reaction mixtures were subjected to SDS-PAGE followed by exposure for autoradiography according to our published procedure (Nikhil et al., 2021). For the analysis of MKK7 phosphorylation of c-Myc, in a 20 µL reaction system, 250 ng 6×His-c-Myc and 500 ng GST-MKK7 were incubated in 1× kinase buffer supplemented with 500 µM ATP for 30 min at 30° C. For negative control, MKK7-GST was not added. Afterward, 10 µL of 4×Laemmli sample buffer containing 5% β-mercaptoethanol was added to each sample, followed by heating at 95° C. for 5 min. Proteins were resolved by SDS-PAGE and analyzed by immunoblotting.

Structural Modeling

The structural model of the RIPK2-MKK7 complex was generated from available structures in the RCSB Protein Data Bank (PDB). Briefly, the 3D structure of the RIPK2 kinase domain was used from an available structure (PDB code 6ES0), and that of the MKK7 kinase domain was generated by homology modelling, using the structure of MEK1 (PDB code 1S9I) as a template. Putative dimerization models of kinase domains were generated with Rosetta (Moretti et al., 2018) and ZDOCK. Top 10 models from each program were further subjected to molecular minimization and 1.2 ns short molecular dynamics using Desmond), in order to optimize molecular interaction and estimate energetics of the complex. Finally, the energetically stable protein complex was selected.

Correlation Analysis

To perform correlation analysis, we analyzed the PCTA prostate cancer (n=2,113), TCGA Firehose Legacy prostate cancer (n=499), and TCGA PanCancer Atlas (32 studies) cohort data. For gene expression abundance, PCTA provides median-centered and quantile normalized expression values. For the TCGA Firehose Legacy prostate cancer cohort, median-centered log 2(FPKM+1) values were computed for each gene. For the TCGA PanCancer Atlas, RSEM (RNA-Seq by Expectation Maximization) values were log-transformed using log 2(RSEM value+1) and median centered by genes. Given these expression values, gene-set activation score was computed by using weighted Z-score method (Levine et al., 2006). Spearman's method was used to compute correlation coefficients between genes and/or gene-sets, using the PCTA portal (thepcta.org) or R (v3.6.2).

Kaplan-Meier Survival Analysis

Kaplan-Meier survival analyses were performed using the TCGA PanCancer Atlas cohort and the Jain cohort (GSE116918). The log-rank test was performed to compute hazard ratios and statistical significance of survival difference between groups. The graphs were generated using R (v3.6.2).

Statistical Analysis

Statistical analyses were performed in R (v3.6.2) (R Core Team, 2019). Unless specified, all statistical tests were two-sided with a significance level of P<0.05. All statistics and reproducibility information are reported in the figure legends. For animal studies, sample sizes were defined on the basis of past experience to achieve 80% power. For ethical reasons, the minimum number of animals necessary to achieve the scientific objectives was used.

RIPK2 is a Top Candidate Druggable Target for PC Metastasis

Figure 16:
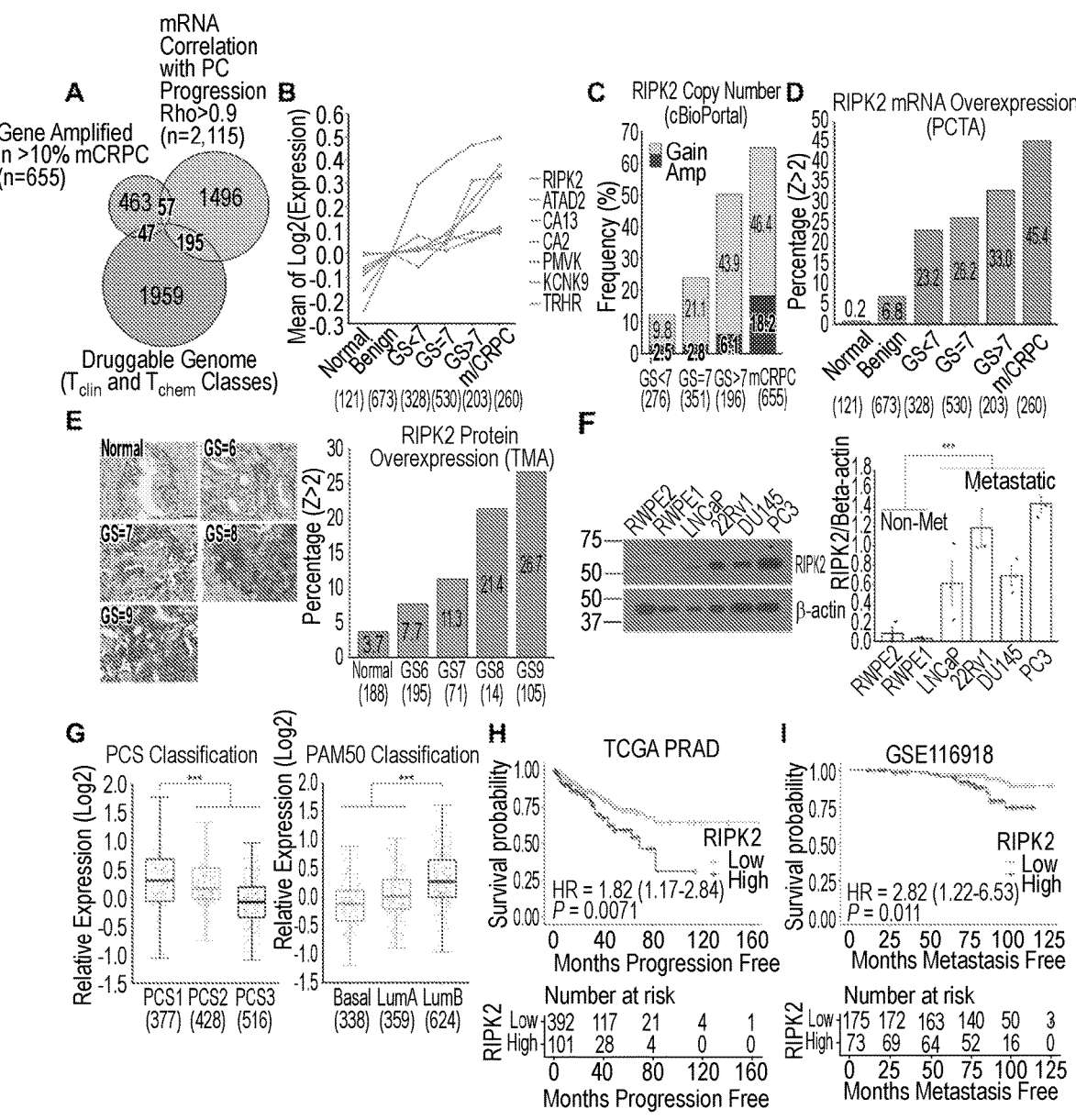
FIG. 16 (panels A-I) shows that RIPK2 is a Top Candidate Druggable Target for Prostate Cancer (PC) Metastasis. (A) Venn diagram of human genes meeting the three indicated criteria. (B) mRNA level changes of the seven overlapping genes along with PC progression. GS: Gleason score; m/CRPC: metastatic or castration-resistant PC. (C) Frequencies of RIPK2 copy number amplification and gain along with PC progression. (D) Frequencies of RIPK2 mRNA overexpression (Z>2 relative to tumor-adjacent normal tissue) along with PC progression. PCTA: Prostate Cancer Transcriptome Atlas. (E) Comparison of RIPK2 protein expression levels in primary PC. Left panel: representative IHC images (scale bar=25 μm). Right panel: Frequencies of RIPK2 protein overexpression (Z>2 relative to tumor-adjacent normal tissue) along with PC progression. TMA: Tissue microarray. (F) Comparison of RIPK2 protein levels in six commonly used prostate cell line models. Left panel: representative immunoblotting images. Right panel: bar plot of relative RIPK2 protein abundance normalized against β-actin. (G) Boxplots of RIPK2 mRNA levels in three PCS (left) and PAM50 (right) subtypes of prostate tumors in the PCTA cohort. PCS1 and LumB are aggressive PC subtypes. (H) Kaplan-Meier progression-free survival analysis of PC patients in the TCGA PanCancer Atlas cohort stratified by RIPK2 mRNA abundance. HR: hazard ratio (95% confidence interval). (I) Kaplan-Meier metastasis-free survival analysis of PC patients in the Jain cohort (GSE116918) stratified by RIPK2 mRNA abundance. The numbers in parentheses represent sample sizes. P values were determined by unpaired two-tailed Student's t-test (panel F), rank sum test (G), or two-sided log-rank test (H and I) (***p<0.001). Data are mean±standard error of the mean (SEM) of three biological replicates (F).

To identify therapeutically viable protein targets for metastasis in a significant subset of PC patients, we applied three stringent criteria to filter large-scale clinical omics databases: the cBioPortal for Cancer Genomics, the Prostate Cancer Transcriptome Atlas (PCTA), and the Pharos for human druggable genome. These criteria include: 1) genes are recurrently (>10%) amplified in lethal mCRPC (n=655), 2) mRNA levels have a high correlation (rho>0.9) with Gleason score and the natural history of PC progression, which are associated with increased metastatic risk (n=2, 115), and 3) proteins can be readily targeted by Tclin- or Tchem-grade inhibitors, which are FDA approved or have an activity cutoff of <30 nM. A total of 574, 1,755, and 2,208 human genes meet the three criteria, respectively, with an overlap of seven genes, whose encoded proteins represent candidate druggable targets of PC metastasis (FIG. 16A). Among the seven genes, RIPK2 has the highest mRNA level increase along with PC progression from benign to lethal disease (FIG. 16B). Currently, very little is known about the functions and mechanisms of RIPK2 in PC progression and metastasis.

To determine whether RIPK2 is associated with PC progression and metastasis at different molecular levels (i.e., DNA, RNA, and protein), we analyzed publicly accessible PC genomics and transcriptomics datasets and performed immunohistochemical (IHC) analysis of PC tissue microarrays. At the DNA level, the frequency of RIPK2 copy number amplification or gain increases along with PC progression, ranging from 12.3% in low-grade, low risk PC to 64.6% in mCRPC (FIG. 16C). RIPK2 copy numbers are strongly associated with RIPK2 mRNA expression levels in PC tissue specimens (rho=0.68, p=2.2E-16) (Correlation of RIPK2 copy numbers and mRNA abundance (both log 2-transformed) in the TCGA (The Cancer Genome Atlas) prostate cancer (PC) cohort was done; figure not shown). As expected, the frequency of RIPK2 mRNA overexpression (Z>2 relative to tumor-adjacent normal tissue) also increases along with the natural history of PC progression, rising from 0.8% in tumor-adjacent normal tissue to 45.4% in metastatic or castration-resistant PC (FIG. 16D. Swarm plot of RIPK2 mRNA abundance was done, which was Z-transformed relative to tumor-adjacent normal tissue, in the indicated groups of tissue specimens contained in the PCTA (Prostate Cancer Transcriptome Atlas). Furthermore, RIPK2 mRNA abundance is strongly associated with RIPK2 protein abundance in various human cancer cell lines (rho=0.66, p=2.2E-16) (Correlation of RIPK2 mRNA abundance and protein abundance (both log 2-transformed) in cancer cells contained in the CCLE (Cancer Cell Line Encyclopedia) was performed, figure not shown). Consistently, the frequency of RIPK2 protein overexpression (Z>2 relative to tumor-adjacent normal tissue) is positively associated with Gleason scores (a predictor of PC recurrence), ranging from 3.7% in tumor-adjacent normal tissue to 26.7% in tumors with the Gleason score of 9 (FIG. 16E. Swarm plot of RIPK2 protein abundance was done, which was Z-transformed relative to tumor-adjacent normal tissue, in the indicated groups of tissue specimens contained in a tissue microarray. Representative images of immunohistochemistry (IHC) staining of RIPK2 in control or RIPK2-KO HEK293T cells were obtained (figure not shown)). Consistent with the clinical findings, RIPK2 protein abundance is substantially higher in metastatic than non-metastatic prostate cell line models (FIG. 16F). Collectively, the findings suggest that the genetic alteration and overexpression of RIPK2 are strongly associated with PC progression and metastasis and are frequent events in lethal or high-risk PCs.

To investigate whether RIPK2 is associated with PC aggressiveness, we compared RIPK2 mRNA levels in PC subtypes with different levels of aggressiveness. RIPK2 mRNA levels are significantly higher in aggressive PC subtypes such as Prostate Cancer Subtype 1 (PCS1) and Luminal B (LumB), compared with the other two less aggressive PCS or PAM50 (prediction analysis of microarray 50) subtypes, in both PCTA and The Cancer Genome Atlas (TCGA) cohorts (FIG. 16G. Boxplots of RIPK2 mRNA Levels in the PCS and PAM50 subtypes of PC tumors in the TCGA Firehose Legacy Cohort (n=499) were made). Of note, PCS1 tumors progress more rapidly to metastatic disease than PCS2 and PCS3 tumors (hazard ratio=4.8), and LumB tumors exhibit poorer clinical prognosis than LumA and Basal tumors.

To determine whether RIPK2 is associated with poor prognosis, we performed Kaplan-Meier survival analyses. The high mRNA abundance of RIPK2 is significantly associated with worse progression-free and metastasis-free survival of PC patients (FIGS. 16H and 16I). In addition to PC, RIPK2 is frequently amplified and/or overexpressed in several other cancer types such as melanoma and breast cancer (FIG. 23), and its mRNA overexpression is associated with significantly shorter overall survival in nine cancer types, including three kidney cancer subtypes, thyroid carcinoma, and esophageal adenocarcinoma (FIG. 24). Thus, RIPK2 overexpression is associated with poor prognosis in PC and many other cancers.

RIPK2 is Necessary for PC Metastasis

Figure 17:
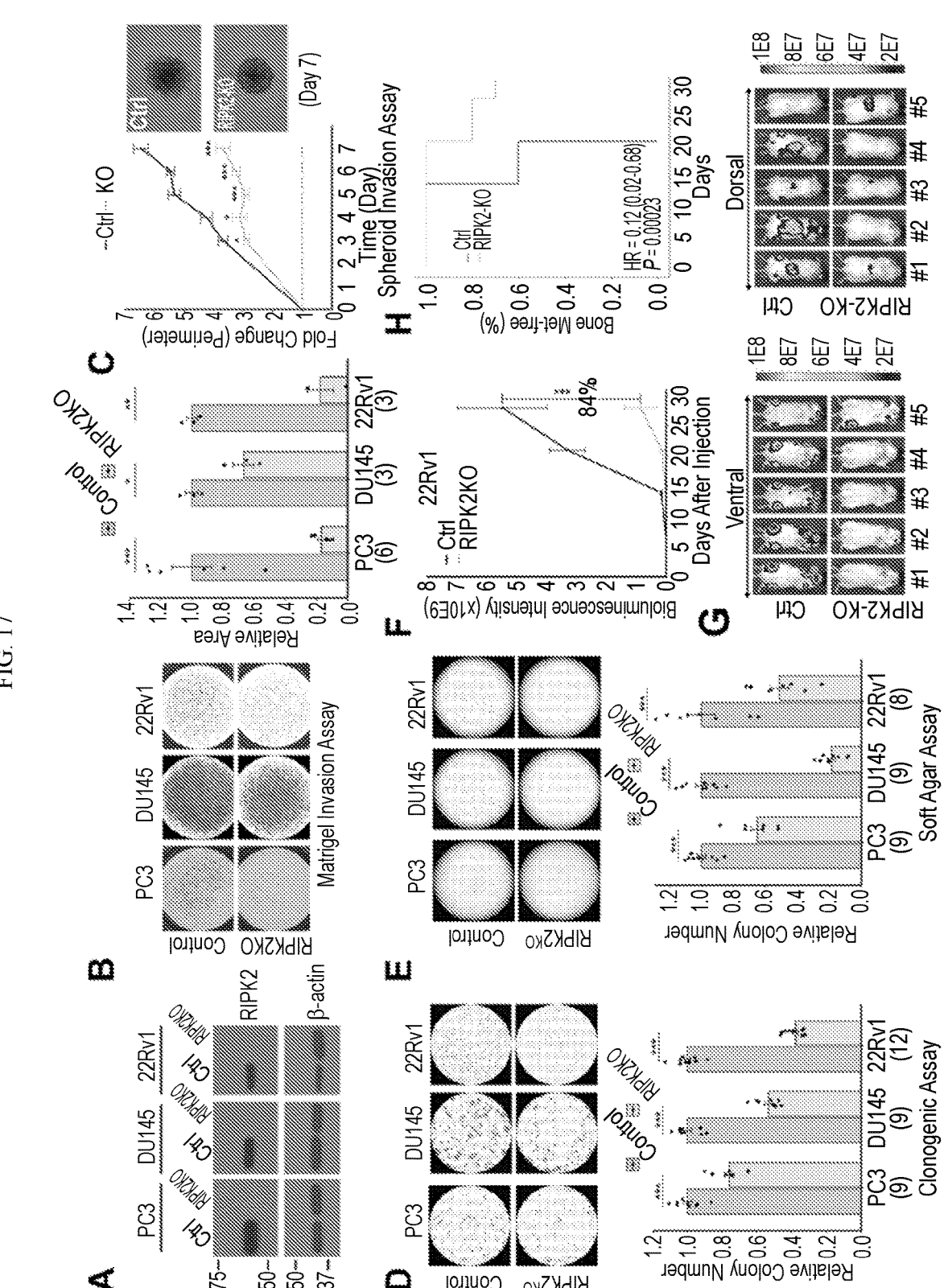
FIG. 17 (panels A-H) shows that RIPK2 is Necessary for PC Metastasis. (A) Representative immunoblots of RIPK2 in total lysates derived from control PC cells and cells with RIPK2 knockout by CRISPR/Cas9 using gRNA 10. (B) Representative images (left) and quantification (right) of Matrigel invasion assay of control or RIPK2-KO PC cells. (C) Quantification and representative images of 3D spheroid invasion assay of control or RIPK2-KO PC3 cells (n=6 per group). (D) Representative images (upper) and quantification (lower) of anchorage-dependent colony formation assay of control or RIPK2-KO PC cells. (E) Representative images (upper) and quantification (lower) of anchorage-independent soft agar colony formation assay of control or RIPK2-KO PC cells. (F-H) Luciferase-tagged control or RIPK2-KO 22Rv1 cells were intracardially injected into male SCID/beige mice (n=5 per group), which were monitored every week for 4 weeks by in vivo bioluminescence imaging (BLI). (F) Total BLI intensities over time. (G) BLI images taken 4 weeks after the intracardiac injection from the ventral (left) and dorsal (right) sides. (H) Percentage of knee joints free of metastasis (n=10 joints per group). P values were determined by unpaired two-tailed Student's t-test (B, C, D, and E), two-way ANOVA (F), or two-sided log-rank test (H) (*p<0.05, p<0.01, and *p<0.001). Data are shown as Mean±SEM and biological replicate numbers are shown in parentheses (B, D, and E).

To investigate whether targeting RIPK2 suppresses CRPC progression and metastasis, we stably knocked out RIPK2 from three androgen-independent PC cell lines: androgen receptor (AR)-negative PC3 and DU145 as well as AR-positive 22Rv1, using the CRISPR/Cas9 system (FIG. 17A). Of note, PC3 has RIPK2 gene amplification (5-6 copies/cell), and DU145 and 22Rv1 have RIPK2 gain (~3 copies/cell). All the three cell lines have much higher RIPK2 protein levels than non-metastatic prostate cell lines (FIG. 16F).

To determine whether RIPK2-knockout (RIPK2-KO) suppresses PC progression in vitro, we performed cell proliferation, transwell migration, matrigel invasion, 3D spheroid invasion, colony formation, and soft agar assays. RIPK2-KO only had a negligible effect on cell proliferation or migration in 2D culture (FIGS. 25A and 25B). Nevertheless, using two independent guide RNAs (gRNAs), RIPK2-KO significantly reduced the matrigel invasion of PC cells (FIGS. 17B and 25C). Moreover, RIPK2-KO significantly suppressed spheroid invasion (FIGS. 17C and 25D), anchorage-dependent colony formation (FIG. 17D), and anchorage-independent soft agar colony formation (FIG. 17E). Together, RIPK2 is required for PC cell invasion and colony formation, key biological processes in cancer metastasis.

To investigate whether RIPK2-KO suppresses PC metastasis in vivo, we conducted intracardiac injection of luciferase-labeled control and RIPK2-KO 22Rv1 cells into male SCID/Beige mice. Of note, 22Rv1 cells express both full-length and constitutively active truncated variants of AR, recapitulating aggressive mCRPC tumors. Compared with the control group, mice harboring RIPK2-KO 22Rv1 cells showed substantially lower metastatic burden (84% reduction at week 4) (FIGS. 17F, 17G and 26A-C), longer bone metastasis-free survival (FIG. 17H), and less weight loss (FIG. 26D), suggesting that RIPK2 is essential for PC metastasis. In addition, to determine whether RIPK2-KO affects tumor growth in vivo, we performed subcutaneous injection of control and RIPK2-KO 22Rv1 cells in male SCID/Beige mice. Consistent with the in vitro cell proliferation results (FIG. 23A), RIPK2-KO 22Rv1 xenografts had a significant but modest reduction in tumor growth rate, weight, and size, compared with control tumors (FIG. 27). Collectively, the results suggest that RIPK2 is mainly required for PC metastasis rather than tumor growth.

Label-Free Proteomics Reveals RIPK2 as a Potent Activator of c-Myc

In the canonical RIPK2 signaling pathway, the inflammatory RIPK2 activity is largely mediated by the activation of NF-κB, a central mediator of pro-inflammatory gene induction. However, RIPK2-KO did not inhibit NF-κB signaling in PC3 or 22Rv1 cells (immunoblot of p-p65 (a surrogate for NF-κB p65 activity), NF-κB p65, and IκBa (an endogenous inhibitor of NF-κB) in total lysates of control or RIPK2-KO PC3 and 22Rv1 cells show that RIPK2 Knockout Does Not Inhibit the Canonical RIPK2-downstream NF-κB Pathway, figure not shown) suggesting that RIPK2 may function via a novel non-canonical signaling pathway in PC. To map the non-canonical RIPK2 pathway, we performed an unbiased label-free proteomic analysis to comprehensively identify RIPK2 downstream effectors, followed by bioinformatic analysis to identify key mediators of RIPK2 signaling. Here, we chose the control and RIPK2-KO PC3 cells for comparison, because PC3 has the highest RIPK2 protein expression level among all the cell lines screened (FIG. 16F). To identify consistent changes across different clones, we analyzed three PC3 single-cell clones (#4, #12, and #16) with stable RIPK2-KO, in comparison with control PC3 cells.

Figure 18:
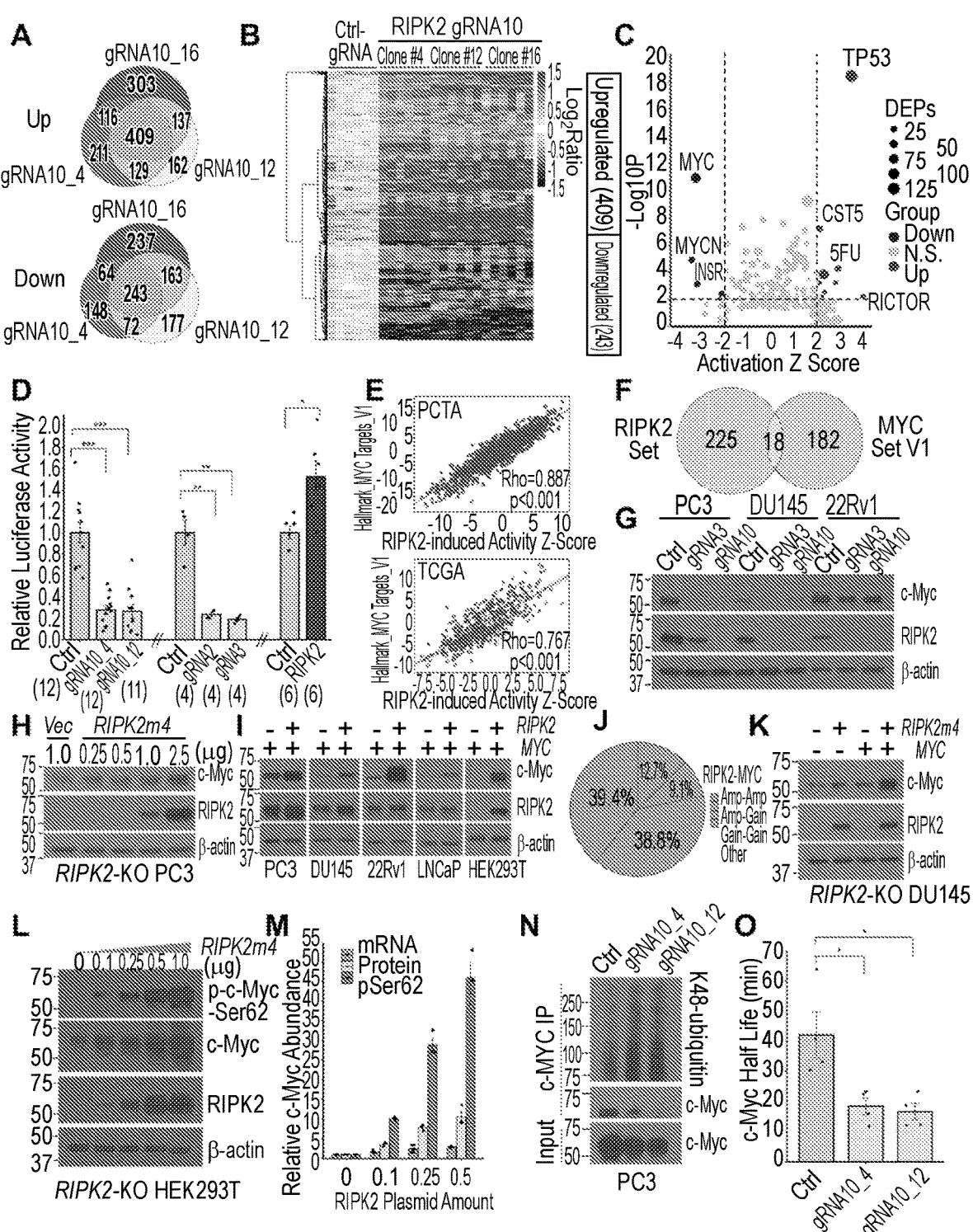

Comprehensive proteomic analysis identified 5,237 protein groups with a false discovery rate (FDR) of <1%. After quality assessment (PC3/Ctrl-gRNA: PC3 were cells stably transfected with a non-targeting control gRNA. PC3/gRNA10-4: PC3 cells were stably transfected with RIPK2-targeting gRNA #10, single clone #4. PC3/gRNA10-12: PC3/gRNA10, single clone #12. PC3/gRNA10-16: PC3/gRNA10, single clone #16) and statistical analysis (Differentially Expressed Proteins (DEPs) by RIPK2-KO in PC3 cells were identified. Volcano plots of all protein groups quantified by label-free proteomics comparison of control PC3 cells and RIPK2-KO PC3 single-cell clones #4, #12, or #16 were made. Volcano plot comprising the 652 DEPs consistently identified from all the three single-cell clones, compared with control PC3 cells were also made), we found that 243 and 409 protein groups are consistently downregulated or upregulated in all the three RIPK2-KO PC3 clones, compared with control PC3 cells, respectively (q<0.005) (FIGS. 18A and 18B). It remains unclear why RIPK2-KO induced many more upregulated proteins than downregulated proteins. Nonetheless, the difference is not due to inappropriate data normalization, because the label-free proteomics data were already normalized by MaxQuant (a widely used proteomics software program) and the log 2-transformed ratios were centered around 0 (Density plots of log 2-transformed protein ratios between RIPK2-KO PC3 single-cell clones and control PC3 cells were done). ToppFun gene ontology enrichment analysis showed that the downregulated protein set is the most significantly associated with ribosome biogenesis and mitochondria, whereas the upregulated protein set is the most significantly associated with cytoskeleton organization and focal adhesion (Top 10 Significantly Enriched Gene Ontology (GO) Terms were Identified by ToppFun Analysis). Using the downregulated and upregulated protein sets, we computed the Z scores of RIPK2-induced and RIPK2-repressed activities, respectively, in each sample of the PCTA and TCGA cohorts. In line with the aforementioned RIPK2 mRNA findings (FIGS. 16B and 16G), the RIPK2-induced activity scores are positively—whereas the RIPK2-repressed activity scores are negatively-associated with PC progression and aggressiveness in both cohorts (Line Plots of the Mean Z Scores of the Protein-set Downregulated or Upregulated by RIPK2-KO in PC Tissue Specimens were made, figure not shown. P values were determined by one-way ANOVA test. RIPK2KO_Dn stands for the 243 proteins downregulated by RIPK2-KO, from which RIPK2-induced activity scores were calculated. RIPK2KO_Up represents the 409 proteins upregulated by RIPK2-KO, from which RIPK2-repressed activity scores were computed).

To identify key mediators of RIPK2 signaling in PC, we conducted an upstream regulator analysis of the 652 (243 downregulated and 409 upregulated) differentially expressed protein groups (DEPs), using Ingenuity Pathway Analysis (IPA). The in-silico procedure showed that, among all putative upstream regulators, c-Myc was the most significantly suppressed by RIPK2-KO (FIG. 18C). Consistently, gene set enrichment analysis (GSEA) of all quantified proteins identified MYC_Targets_V1 and V2 as the most strongly downregulated hallmark gene signatures in RIPK2-KO PC3 clones, compared with control cells (it was found that MYC Gene Signatures (V1 and V2) are the Most Strongly Downregulated Hallmark Signatures by RIPK2-KO. Bar graph of normalized enrichment scores calculated by Gene Set Enrichment Analysis (GSEA) for the top 8 enriched hallmark signatures from the Molecular Signature Database (MSigDB). Red, orange, and blue dots represent the scores derived from RIPK2-KO PC3 clones #4, #12, and #16, compared with control PC3 cells. Q values indicate combined q values computed by MetaP in R. GSEA plots showing the downregulation of MYC target gene sets V1 and V2 in RIPK2-KO PC3 clones, compared with control PC3 cells. Figure not shown). As mentioned above, ribosome biogenesis—a key biological process regulated by c-Myc—is the most significantly downregulated biological process by RIPK2-KO. Thus, c-Myc is potentially a central mediator of RIPK2 signaling. To confirm that RIPK2 activates c-Myc signaling, we performed c-Myc luciferase reporter assays in RIPK2-manipulated PC3 cells. RIPK2-KO by three different gRNAs substantially decreased—whereas RIPK2 overexpression significantly increased—c-Myc activity in PC3 cells, compared with their respective controls (FIG. 18D).

To evaluate the clinical relevance of our finding that RIPK2 activates c-Myc, we performed correlation analyses in PC tissue specimens. Strikingly, in both PCTA and TCGA cohorts, RIPK2-induced activity scores are highly correlated with MYC activity scores (FIG. 18E. Scatter plots of RIPK2-induced activity Z scores against Hallmark_MYC_Targets_V2 gene set activity Z scores in the PCTA and TCGA cohorts were made), even though the overlap between the RIPK2 and MYC signature genes is modest (FIG. 18F. Venn diagrams of the genes contained in the RIPK2-induced protein signature (i.e., the 243 protein groups downregulated by RIPK2-KO) and those in the Hallmark_MYC_Targets_V2 gene signature were made). In comparison, RIPK2 mRNA levels have lower correlations with MYC activity scores, but still at levels comparable to those between MYC mRNA levels and MYC activity scores. Interestingly, among all the human kinases, RIPK2 mRNA levels have the strongest correlation with MYC activity scores in the PCTA and TCGA cohorts on average. Out of the 50 Hallmark gene sets in the Molecular Signatures Database (MSigDB) (Liberzon et al., 2015), the MYC_Targets gene sets (V1 and V2) are among the most strongly associated with RIPK2 mRNA and activity levels in both cohorts. In addition, our pan-cancer analysis showed that RIPK2-induced activity scores are strongly (rho=0.88 on average) correlated with MYC activity scores across all the 32 cancer types. Together, the findings suggest that RIPK2 is a potent activator of c-Myc in PC and potentially in various cancers.

RIPK2 Upregulates the c-Myc Protein

Various studies have shown that the c-Myc oncoprotein is a crucial component of metastasis of many cancers (including PC) and that MYC knockdown substantially reduces PC metastasis in vivo. Thus, we investigated whether RIPK2-KO suppresses PC metastasis via modulating the c-Myc protein. Our results showed that stable RIPK2-KO by two independent gRNAs substantially downregulated c-Myc protein levels in PC3, DU145, and 22Rv1 cells (FIG. 18G). Ectopic expression of RIPK2m4, whose gRNA10-targeting spacer region was silently mutated to disable Cas9 recognition, increased the protein abundance of endogenous c-Myc in a dose-dependent fashion in RIPK2-KO PC3 cells (FIG. 18H) and of exogenous c-Myc in five different cell lines (FIG. 18I). Together, RIPK2 positively regulates the c-Myc protein independent of cell type.

The RIPK2 and MYC genes are located about 38 megabases apart on chromosome 8q (FIG. 28A), whose gains are among the most frequent cytogenetic alterations in PC.

Our analysis of three large-scale genomic profiling studies of mCRPC tissue specimens (n=655) showed that RIPK2 and MYC are co-amplified/gained in 60.6% of all specimens (FIG. 18J). Frequent RIPK2 and MYC co-amplification/gain also occurs in several other cancer types, such as uterine, breast, liver, and bladder cancers (FIG. 28B). Interestingly, compared with the forced expression of RIPK2 or MYC alone, the co-transfection of both RIPK2 and MYC—a mimic of RIPK2 and MYC co-amplification/gain—resulted in much higher c-Myc protein levels in RIPK2-KO DU145, 22Rv1, and HEK293T cells (FIGS. 18K and 28C). Thus, the co-amplification/gain of RIPK2 and MYC, a highly frequent event in PC and several other cancer types, synergistically contributes to c-Myc protein abundance independent of the cellular context.

RIPK2 Phosphorylates and Stabilizes the c-Myc Protein

To determine how RIPK2 upregulates the c-Myc protein, we first examined whether RIPK2 regulates the transcription of the MYC gene. Using quantitative real-time polymerase chain reaction (RT-PCR), we found that either transient RIPK2 overexpression or inhibition by GSK583 (a RIPK2-selective inhibitor) at different doses and time only modestly (~10%) regulated MYC mRNA abundance (the Regulation of c-Myc by RIPK2 is Mainly not at the Transcriptional Level). Thus, the regulation of c-Myc protein abundance by RIPK2 is mainly via a post-transcriptional mechanism.

In human cells, the c-Myc protein can be rapidly stabilized through Ser62 phosphorylation, which prevents the targeted degradation of c-Myc by the ubiquitin-proteasome system (Farrell and Sears, 2014). Therefore, we investigated whether RIPK2 phosphorylates and stabilizes the c-Myc protein. Ectopic overexpression of RIPK2 increased the abundance of phospho-c-Myc-Ser62 (p-c-Myc-Ser62) and total c-Myc in a dose-dependent fashion (FIG. 18L). Moreover, the abundance of p-c-Myc-Ser62 increased much faster than the mRNA and protein abundance of c-Myc (FIG. 18M), suggesting that RIPK2 regulates c-Myc largely (if not exclusively) by phosphorylating and stabilizing c-Myc. Consistently, RIPK2-KO significantly increased the K48-linked ubiquitination of c-Myc, a signal for proteasomal degradation (FIG. 18N). In addition, RIPK2-KO reduced the half-life of the c-Myc protein, whose degradation can be blocked by the proteasome inhibitor MG132 (FIG. 18O. immunoblots and quantification of Myc protein levels in total lysates of RIPK2-KO PC3 single-cell clones #4 and #12, compared with control PC3 cells, in response to cyclo-heximide (CHX) treatment (n=4), and immunoblots and quantification of c-Myc protein levels in total lysates of PC3 cells treated with DMSO or MG132, in the presence of CHX treatment, show Genetic Knockout of RIPK2 Destabilizes the c-Myc Protein by Promoting its Proteasomal Degradation; figures not shown). Of note, RIPK2 is more frequently amplified or gained in mCRPC or overexpressed in primary PC than all known direct c-Myc-Ser62 kinases (FIG. 29). This raises a possibility that RIPK2 can more efficiently stabilize and activate c-Myc, and thus its overexpression is more favored by PC cells than the known direct c-Myc-Ser62 kinases. Collectively, RIPK2 stabilizes the c-Myc protein by phosphorylating its Ser62 residue and preventing it from proteasomal degradation, and RIPK2 is potentially a major stabilizer of the c-Myc protein in PC cells.

Integrative Proteomics Analysis Identifies Candidate Kinase Pathways Mediating RIPK2 Phosphorylation of c-Myc-Ser62

To determine whether RIPK2 directly phosphorylates c-Myc under physiological conditions, we investigated whether the two proteins bind to each other—a prerequisite for direct RIPK2 phosphorylation of c-Myc—by performing proximity ligation assay (PLA) and immunoprecipitation (IP). Of note, PLA detects proteins in close proximity (<40 nm) and thus is particularly useful for detecting transient protein-protein interactions. In comparison, IP is more commonly used in detecting stable protein-protein interactions. Nevertheless, both failed to detect the protein-protein association between endogenous RIPK2 and c-Myc (PLA (proximity ligation assay) images and quantification of endogenous RIPK2 and c-Myc proteins in parental HEK293T cells, and immunoblots of RIPK2 and c-Myc in RIPK2 protein complexes immunoprecipitated from parental PC3 cells or in PC3 total lysates show that RIPK2 Does not Bind to c-Myc Under a Physiological Condition), suggesting that RIPK2 phosphorylates c-Myc-Ser62 via intermediary kinase(s).

To identify the intermediary kinase(s), we firstly mapped the subcellular location and functional domain of RIPK2 that are critical for RIPK2 regulation of c-Myc. The RIPK2 protein is predominantly localized in the cytoplasm but was also detected in nuclei under certain conditions. RIPK2 contains two functional domains: an N-terminal kinase domain and a C-terminal CARD domain. To determine which subcellular localization and functional domain(s) of RIPK2 are critical for its regulation of c-Myc, we generated five C-terminally 3×FLAG-tagged RIPK2 constructs: 1) wild-type, 2) N-terminally tagged with a nuclear localization signal (NLS), 3) N-terminally tagged with a nuclear export signal (NES), 4) with the deletion of the kinase domain (ΔKinase), and 5) with the deletion of the CARD domain (ΔCARD). Our immunofluorescence results confirmed that the NLS and NES targeted RIPK2 into the nuclei and the cytoplasm, respectively (RIPK2-KO HEK293T cells were transiently transfected with N-terminally NLS-tagged (upper) or NES-tagged (lower) RIPK2m4, both of which were C-terminally tagged with a 3×FLAG tag. An anti-FLAG antibody was used for immunofluorescence imaging). Ectopic expression of NES-RIPK2 and not NLS-RIPK2, as well as of ΔCARD-RIPK2 but not ΔKinase-RIPK2, significantly increased c-Myc protein abundance (FIG. 19A). These suggest that both the cytoplasmic localization and the kinase domain of RIPK2 are critical for RIPK2 regulation of c-Myc.

Thus, we postulated that certain protein(s) binding to the kinase domain, but not other regions, of cytoplasmic RIPK2 are critical for mediating RIPK2's indirect phosphorylation of c-Myc-Ser62. To identify such protein(s), we performed a rigorously controlled interactome analysis by immunoprecipitation-mass spectrometry (IP-MS), including two experimental (G5 and G3) and three control (G1, G2, and G4) conditions (FIG. 19B. RIPK2 Complexes and Predicted Immunoprecipitation Products; proteins specifically bound to the kinase domain and no other regions of RIPK2). The analysis identified 1,189 proteins with an FDR of <1%. After quality assessment (Immunoblots of the indicated proteins in the four IP biological replicates. RIPK2-KO HEK293T cells were transiently transfected with the indicated forms plasmids, and total lysates were subjected to IP using antibodies against the indicated baits. IP products and total lysates (input) were analyzed by immunoblots to probe the indicated proteins. Unsupervised clustering of the log 2(LFQ)

values to detect outlier samples (labeled with x) in the five IP groups (G1-G5). IP products were analyzed by in-gel digestion coupled with mass spectrometric analysis (GeLC-MS/MS). The label-free quantification (LFQ) values were log 2-transformed and clustered. Outlier samples were detected by visually inspecting the hierarchical cluster heatmaps) and statistical comparison (Volcano plots showed the log 2-transformed protein ratios versus the –log 10(P) values following quantitative comparison of (A) G3 vs. G1, (B) G3 vs. G2, (C) G3 vs. G4, (D) G5 vs. G1, (E) G5 vs. G2, (F) G5 vs. G4, (G) G4 vs. G1, and (H) G4 vs. G2), we identified 219 protein candidates that associate with the kinase domain and no other regions of cytoplasmic RIPK2 (FIG. 19C. Also, unsupervised clustering of protein groups in each of the eight comparisons identify candidate proteins associated with the kinase domain and no other regions of cytoplasmic RIPK2). These candidates include two known RIPK2-binding partners, XIAP and RPL38 (Swarm plot of log 2(LFQ) values of XIAP and RPL38, two known RIPK2-interacting proteins, in the five IP-MS groups were made, figure not shown). The candidate interacting proteins also include six kinases yet none of these kinases was previously reported to be direct c-Myc-Ser62 kinases.

To identify kinase(s) that link RIPK2 to c-Myc-Ser62, we then performed a phosphoproteomic comparison of two RIPK2-KO PC3 clones with control PC3 cells (FIG. 19D). The analysis identified 6,749 phosphosites, which correspond to 2,716 phosphoproteins, with an FDR of <1% and a localization probability of >0.75 (A Pie chart of the 6,749 identified phosphoserine (pS), phosphothreonine (pT), and phosphotyrosine (pY) sites (FDR<1% and localization probability >0.75)). Following quality assessment (FIG. 27B) and statistical analysis (Volcano plots of the phosphorylation levels of all quantified phosphosites in control PC3 cells relative to RIPK2-KO PC3 clone #4 or clone #12 were made, figure not shown), we analyzed relative kinase activities using the kinase-substrate enrichment analysis (KSEA). The relative activities of 50 and 58 kinases were quantified based on ≥5 substrate phosphosites per kinase in the two RIPK2-KO PC3 clones, respectively (Bar plots of the inferred activities of candidate kinases downstream of RIPK2 in control PC3 cells relative to RIPK2-KO PC3 clone #4 or clone #12, with an overlap of 47 kinases (Venn diagram was made of candidate RIPK2-regulated kinases identified from control PC3 cells in comparison to the two RIPK2-KO PC3 single-cell clones). RIPK2 appeared to activate 36 kinases (FIG. 19E), of which nine were reported as direct c-Myc-Ser62 kinases but not as direct RIPK2 substrates.

The interactome and phosphoproteomics findings raised a possibility that RIPK2 binds to and activates a protein, which in turn activates a direct c-Myc-Ser62 kinase. Thus, we applied IPA to connect the 219 RIPK2-interacting proteins with the nine direct c-Myc-Ser62 kinases, based on whether the former can directly activate the latter. Interestingly, seven RIPK2-interacting proteins were found to be able to directly activate seven direct c-Myc-Ser62 kinases (FIG. 19F). Among the latter, c-Jun N-terminal kinases (JNKs) downstream of MAP2K7 (also known as MKK7) appeared to be most activated by RIPK2 (FIG. 19F). Of note, studies have shown that JNKs can directly phosphorylate c-Myc-Ser62 and that targeting JNKs reduces c-Myc protein abundance. Together, RIPK2 may indirectly phosphorylate c-Myc-Ser62 via multiple kinase pathways, among which the MKK7/JNK signaling axis is potentially the central pathway.

MKK7 is a Major Mediator of RIPK2 Regulation of c-Myc

Our network model suggested that RIPK2 may bind to and activate MKK7 and that MKK7 is potentially a major mediator of RIPK2's indirect phosphorylation and stabilization of c-Myc (FIG. 19F). To confirm the protein-protein association between RIPK2 and MKK7, we performed PLA, fluorescence colocalization, and co-IP analyses. PLA assays confirmed that endogenous RIPK2 and MKK7 are in close proximity in HEK293T as well as PC3, DU145, and 22Rv1 cells under normal culture conditions, predominantly if not exclusively in the cytoplasm (FIG. 20A, 20B. RIPK2 Binds to and Activates MKK7, a Major Mediator of RIPK2 Regulation of c-Myc; PLA images of endogenous RIPK2 and MKK7 proteins in parental PC cells were obtained). Fluorescence colocalization and co-IP analyses further confirmed the colocalization and association of RIPK2 and MKK7 (FIGS. 20C and 20D). Structural modeling suggested that the N-terminal kinase domain of RIPK2 may directly bind to the C-terminal kinase domain of MKK7 (FIG. 20E). To determine whether RIPK2 directly phosphorylates MKK7, we performed radioactive in vitro kinase assays. The result showed that RIPK2 can directly phosphorylate MKK7 (K149A), a kinase-dead form of MKK7 (FIG. 20F). In addition, immunoblotting analysis showed that forced expression of RIPK2 activated MKK7 and JNK in a dose-dependent fashion (FIG. 20G. Scatter plot of the pMKK7-5271 levels in RIPK2-KO HEK293T cells transiently transfected with different doses of the RIPK2m4 plasmid (n=3) were done. Representative immunoblots and scatter plot of the pJNK-T183/Y185 levels in RIPK2-KO HEK293T cells transiently transfected with different doses of the RIPK2m4 plasmid (n=3) were obtained) and that RIPK2-KO decreased the JNK phosphorylation level (a surrogate for MKK7 activity) and c-Myc protein abundance (FIG. 20H). Collectively, the results suggest that RIPK2 binds to MKK7 and activates the MKK7/JNK pathway.

To validate that MKK7 is a major mediator of RIPK2 regulation of c-Myc, we knocked out MKK7 from RIPK2-KO HEK293T cells with two different gRNAs by CRISPR/Cas9. Immunoblotting analysis showed that MKK7-KO decreased RIPK2-induced c-Myc overexpression by ~58% (FIG. 20I. Bar plot of the relative c-Myc protein abundance in HEK293T cells under the indicated conditions were done. Unpaired two-tailed Student's t-test (*p<0.05, ***p<0.001). Data are mean±SEM (n=3)), suggesting that MKK7 is a major (albeit not the only) mediator of RIPK2 regulation of c-Myc. In comparison, the knockout of PRKDC did not significantly affect RIPK2 regulation of c-Myc (FIG. 20I). Of note, the PRKDC gene encodes the DNA-dependent protein kinase catalytic subunit (DNA-PKcs), which we discovered as a RIPK2-interacting protein by IP-MS and confirmed the interaction by immunoblotting and PLA (Swarm plot of log 2(LFQ) values of PRKDC in the five IP-MS groups (n=3), and western blots of PRKDC in immunoprecipitated RIPK2 protein complexes or in total lysates corresponding to the five IP-MS groups, as well as cellular images and quantification of the PLA detecting the association of endogenous RIPK2 and PRKDC in parental HEK293T cells (n=4) showed that PRKDC is a RIPK2-interacting Protein; (Unpaired two-tailed Student's t-test (*p<0.05). Data are mean±SEM)). Moreover, MKK7-KO substantially abrogated RIPK2-induced c-Myc and JNK phosphorylation (FIG. 20J and MKK7 Mediates RIPK2-induced c-Myc and JNK Phosphorylation; Bar graph of relative protein abundance of in HEK293T cells under indicated conditions (n=3) were made), and the effects could be rescued by ectopic expression of MKK7 (FIG. 20K. Bar graph of relative protein abundance or phosphorylation levels in HEK293T cells with RIPK2- and MKK7-double knockout (RIPK2/MKK7-DKO), which were transiently transfected with the RIPK2m4 plasmid and vector or MKK7 (n=3) were made). Together, MKK7 is a major mediator of RIPK2 phosphorylation of c-Myc-Ser62 and regulation of c-Myc. MKK7 is a Direct c-Myc-Ser62 Kinase Consistent with the MKK7-KO result (FIG. 20I), the inhibition of MKK7 kinase activity by MKK7-COV-3, a MKK7-selective inhibitor, significantly decreased RIPK2-induced c-Myc-Ser62 phosphorylation by 45% (FIG. 21A. JNK Only Mediates a Subset of RIPK2/MKK7 Phosphorylation of c-Myc-Ser62; RIPK2/MKK7-DKO HEK293T cells were transiently transfected with 0.5 μg RIPK2m4, 0.5 μg MYC, and 0.1 μg MAP2K7 or vector plasmids. The cells were then treated with the MKK7 inhibitor MKK7-COV-3, the JNK inhibitor JNK-IN-8, or vehicle control. Bar graph of relative p-c-Myc-Ser62 abundance under the indicated conditions were made. MKK7-COV-3, 25 μM; JNK-IN-8, 1 μM; 2-h treatment). In comparison, the inhibition of JNK kinase activity by JNK-IN-8, a potent JNK-selective inhibitor, only reduced RIPK2-induced c-Myc-Ser62 phosphorylation by 16% (FIGS. 21A and S31A), even though it completed abolished RIPK2-induced c-Jun phosphorylation, a surrogate for JNK activity (FIG. 21A. Bar graph of relative p-c-Jun abundance under the indicated conditions were made. MKK7-COV-3: 25 μM; JNK-IN-8: 1 μM; 2-h treatment. Data are Mean±SEM (n=4); unpaired two-tailed Student's t-test;  P<0.01, * P<0.001). In addition, higher concentrations (up to 25 μM) of JNK-IN-8 could not enhance its inhibition of RIPK2-induced c-Myc-Ser62 phosphorylation (representative immunoblots of the indicated proteins under the indicated conditions). Thus, the findings raised a possibility that MKK7 may directly phosphorylate c-Myc-Ser62 and is more potent than JNK in phosphorylating c-Myc-Ser62.

In support of the hypothesis, PLA and immunofluorescence analyses showed that MKK7 colocalizes with c-Myc, predominantly (if not exclusively) in the nuclei (FIG. 21B-C). In vitro kinase assay showed that recombinant MKK7 could directly phosphorylate c-Myc-Ser62 (FIG. 21D). Moreover, in the absence of RIPK2, forced expression of constitutively active MKK7 increased c-Myc and p-c-Myc-Ser62 levels, compared with wild-type and kinase-dead MKK7 (FIG. 21E). Together, active MKK7 can directly phosphorylate c-Myc in the nuclei. To the best of our knowledge, this is the first report that MKK7 is a direct c-Myc-Ser62 kinase.

Subcellular fractionation analysis showed that active and total MKK7 as well as c-Myc and c-Myc-Ser62 were primarily localized in the nuclei, whereas active and total JNK were primarily localized in the cytoplasm (FIG. 21F). PLA analysis showed that forced expression of RIPK2 increased the amount of the MKK7-c-Myc complex in the nuclei (FIG. 21G). Given that RIPK2 binds to and activates MKK7 in the cytoplasm (FIG. 20) and that the activation of certain kinases may stimulate their nuclear translocation, the results support a model that RIPK2 activation of MKK7 in the cytoplasm stimulates the translocation of MKK7 into the nuclei, where MKK7 phosphorylates and stabilizes c-Myc mainly directly and only partially via JNK.

Pharmacological Inhibition of RIPK2 Attenuates RIPK2/MKK7/c-Myc Signaling and Suppresses PC Metastasis According to cell-free biochemical assays, RIPK2 can be potently inhibited by multiple small-molecule inhibitors such as GSK583 and Ponatinib. GSK583 is the first commercially available potent RIPK2-selective inhibitor, with an IC50 of 5 nM based on a fluorescence polarization assay.

Ponatinib is a multi-kinase inhibitor approved by the FDA for the treatment of leukemia. According to an ADP-Glo kinase assay, Ponatinib inhibits RIPK2 with an IC50 of 6.7 nM, a potency comparable to that against Abl (IC50 of 1.6 nM), the primary target of Ponatinib. However, the cellular potency of a compound can be significantly lower than the biochemical potency to varying degree (up to several orders of magnitude). This is because the intracellular unbound drug concentration is affected by non-specific binding to cell culture medium proteins and cellular components and by drug-transporting proteins and metabolizing enzymes. Our cell-based assay showed that, under a regular cell culture condition containing 10% fetal bovine serum, 2 h treatment with 10 μM GSK583 and 5 μM Ponatinib substantially decreased MKK7 phosphorylation levels (a surrogate for RIPK2 activity) to a similar extent (FIG. 22A). This suggests that the cellular potency of GSK583 and Ponatinib is much lower than their biochemical potency, and that Ponatinib is a more potent inhibitor of RIPK2 activity than GSK583 in cells. Moreover, 5 μM Ponatinib is more potent than 10 μM GSK583 in inhibiting RIPK2-induced JNK activation (FIG. 22B. Pharmacological Inhibition of RIPK2 Reduces p-JNK, p-c-Myc-Ser62, and c-Myc Levels, Bar plot of the relative phosphorylation levels of JNK in RIPK2-KO HEK293T cells under the indicated conditions were made) and in decreasing endogenous p-JNK, p-c-Myc-S62, and c-Myc levels in parental PC cells (FIG. 22. Representative immunoblots of the indicated proteins in total lysates of PC3 or DU145 cells, which were treated with vehicle control, 10 μM GSK583, or 5 μM Ponatinib in 10% FBS-containing medium for 2 h. were obtained). Together, both GSK583 and Ponatinib can inhibit RIPK2/MKK7(/JNK)/c-Myc signaling, and Ponatinib is more potent than GSK583 in this aspect.

To determine whether pharmacological inhibition of RIPK2 reduces the metastatic potential of PC cells, we performed in vitro 3D spheroid invasion and colony formation assays. Both GSK583 and Ponatinib significantly inhibited the spheroid invasion of PC3 cells, and Ponatinib is more potent than GSK583 (FIG. 22D. Pharmacological Inhibition of RIPK2 Suppresses PC Cell Invasion and Colony Formation, representative images of 3D spheroid invasion assays of parental PC3 cells treated with vehicle control, GSK583 (10 μM), or Ponatinib (5 μM) (n=6) were obtained). GSK583 significantly inhibited the colony formation of PC3, DU145, and 22Rv1 cells by ≥40% at a high dose (10 μM) but not at low doses (≤1 μM) (FIG. 22E. Representative images of colony formation assays of parental PC cells treated with vehicle control or GSK583 (10 μM) (n=6) were obtained; bar plot of colony formation assays of parental PC3, DU145, and 22Rv1 cells treated with different concentrations of GSK583 (0-1 μM) (n=6) were made). In comparison, Ponatinib more potently inhibited the colony formation of PC cells, with IC50 values of <1 μM (FIG. 22F. Representative images of colony formation assays of parental PC3, DU145, and 22Rv1 cells treated with different concentrations of Ponatinib (0-5 μM) (n=6) were obtained). Of note, 10 μM GSK583 and 1 μM Ponatinib only had marginal effects on PC cell viability (bar plot of relative viability of PC3 and 22Rv1 cells treated with the indicated concentrations of GSK583 in 10% FBS-containing cell culture medium (n=3 per group), and bar plot of relative viability of PC3 and 22Rv1 cells treated with the indicated concentrations of Ponatinib in 10% FBS-containing cell culture medium (n=2 per group) showed that GSK583 or Ponatinib Only Has Modest Effects on PC Cell Viability When Used at ≤10 or ≤1 μM, Respectively; P values were determined by unpaired two-tailed Student's t-test (n.s.: not significant, *p<0.05, p<0.01, *p<0.001). Data are Mean±SD). Collectively, the in vitro assays suggested that pharmacological inhibition of RIPK2 can effectively attenuate the metastatic potential of PC cells.

In the clinical scenario, patients with nmCRPC have no detectable metastases by conventional radiographic imaging. Nevertheless, using more sensitive prostate-specific membrane antigen ligand positron emission tomography (PSMA-PET), it was found that most high-risk patients with nmCRPC have micrometastases. To investigate whether pharmacological inhibition of RIPK2 can suppress PC metastasis in a setting that mimics the clinical scenario, we injected the aforementioned luciferase-tagged control 22Rv1 cells intracardially into male SCID/Beige mice, and waited for 9 days to allow for the formation of early metastatic lesions, prior to drug treatment (FIG. 22G). To determine whether GSK583 impairs metastatic outgrowth, we randomized the mice into two groups (FIG. 31A), followed by treatment with vehicle control or GSK583 (10 mg/kg) administered by oral gavage every day (po qd). Phenocopying the RIPK2-KO result (FIG. 17F), GSK583 significantly suppressed the metastatic progression of 22Rv1 cells in vivo (50% reduction at week 4) (FIGS. 22H, 22I, S35B, and S35C), without significant effect on mouse weight (FIG. 31D), lethargy, or loss of appetite. Of interest, compared with the whole body, GSK583 more significantly decreased the bioluminescence imaging (BLI) intensities (by 67% at week 4) in the ventral-side mid-body (FIGS. 22J, 32A, and 32B), which largely (if not exclusively) correspond to liver metastasis as supported by histopathological analysis (FIGS. 22K and 32C). Notably, studies have shown that, among common visceral metastases, PC patients with liver metastases exhibited the worst median overall survival. It remains unknown why GSK583 has a higher efficacy on PC liver metastasis than overall metastasis. One possibility is that GSK583 has a better distribution in the liver, similar to nutlin-3a. Taken together, these data show that pharmacologically targeting RIPK2 is a viable strategy to inhibit PC metastasis.

Because our study showed that a higher dose (30 mg/kg po qd) of GSK583 was toxic to mice, we then asked whether the FDA-approved Ponatinib, a more potent RIPK2 inhibitor than GSK583, can more effectively inhibit metastatic outgrowth. Nine days after the intracardiac injection of luciferase-tagged 22Rv1 cells, mice were randomized into three groups, followed by treatment with vehicle control, low-dose Ponatinib (6 mg/kg po qd), or high-dose Ponatinib (30 mg/kg po qd). Of note, the daily dose of 6 mg/kg Ponatinib in mice is estimated to be equivalent of 30 mg for a 60 kg patient (e.g., about 0.5 mg/kg for a patient treatment), a commonly used and well tolerated dose for clinical treatment. As expected, low-dose Ponatinib did not cause any significant effect on mouse weight (FIG. 33A), lethargy, or loss of appetite. However, high-dose Ponatinib caused weight loss and killed one mouse at day 10 after treatment (FIG. 33A). Thus, the dose was reduced from 30 to 15 mg/kg po qd afterwards. BLI analysis showed that Ponatinib significantly impaired 22Rv1 metastatic outgrowth in a dose-dependent fashion (FIGS. 22L, 33B, and 33C). At week 4, low-dose and high-dose Ponatinib reduced total BLI intensities by 74% and 92%, respectively (FIGS. 22L and 22M).

Collectively, the FDA-approved Ponatinib, a more potent RIPK2/MKK7/c-Myc signaling inhibitor than GSK583, can effectively inhibit the outgrowth of PC metastases and thus holds great potential for being repurposed for anti-metastatic therapy.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

What is claimed is:

1. A method of treating prostate cancer or inhibiting metastasis of prostate cancer in a subject in need thereof, comprising:

administering a receptor-interacting protein kinase 2 (RIPK2) inhibitor to the subject, wherein the RIPK2 inhibitor is ponatinib, GSK-583, ODS-101, or a combination thereof, and wherein if the RIPK2 inhibitor is ponatinib, the cancer is not chronic myeloid leukemia (CML), or Philadelphia chromosome-positive (PH+) acute lymphoblastic leukemia (ALL).

2. The method of claim 1, wherein the RIPK2 inhibitor is ponatinib, and the cancer is not chronic myeloid leukemia (CML), or Philadelphia chromosome-positive (PH+) acute lymphoblastic leukemia (ALL).

3. The method of claim 1, wherein the RIPK2 inhibitor is ponatinib.

4. A method of claim 1, wherein the prostate cancer is advanced prostate cancer.

5. A method of claim 1, wherein the subject has been determined to have an increased expression of RIPK2 in cancer cells, as compared to non-cancerous cells, OR wherein the subject has been determined to have a RIPK2 copy number gain, a MYC copy number gain, or a RIPK2/MYC copy number co-gain in cancer cells as compared to non-cancerous cells, OR wherein the subject has been determined to have a RIPK2 copy number amplification, a MYC copy number amplification, or a RIPK2/MYC copy number co-amplification in cancer cells as compared to non-cancerous cells.

6. A method of claim 1, comprising treating the prostate cancer.

7. A method of claim 1, comprising inhibiting prostate cancer metastasis.

8. A method of claim 1, wherein the subject has been determined to have a RIPK2 copy number gain, a MYC copy number gain, or a RIPK2/MYC copy number co-gain in cancer cells as compared to non-cancerous cells, or wherein the subject has been determined to have a RIPK2 copy number amplification, a MYC copy number amplification, or a RIPK2/MYC copy number co-amplification in cancer cells as compared to non-cancerous cells.

* * * * *